United States Patent
Ammann et al.

(10) Patent No.: US 9,707,023 B2
(45) Date of Patent: Jul. 18, 2017

(54) APPARATUS FOR PERFORMING AN OPEN WEDGE, HIGH TIBIAL OSTEOTOMY

(71) Applicant: Arthrex, Inc., Naples, FL (US)

(72) Inventors: Kelly Ammann, Boulder, CO (US); Vincent P. Novak, Longmont, CO (US); Robert E. Schneider, Erie, CO (US); Justin R. Taber, Boulder, CO (US)

(73) Assignee: ARTHREX, INC., Naples, FL (US)

( * ) Notice: Subject to any disclaimer, the term of this patent is extended or adjusted under 35 U.S.C. 154(b) by 203 days.

(21) Appl. No.: 14/530,139

(22) Filed: Oct. 31, 2014

(65) Prior Publication Data

US 2015/0112394 A1    Apr. 23, 2015

Related U.S. Application Data

(63) Continuation of application No. 11/890,129, filed on Aug. 3, 2007, now Pat. No. 8,906,026, which is a (Continued)

(51) Int. Cl.
*A61F 5/00* (2006.01)
*A61B 17/80* (2006.01)
(Continued)

(52) U.S. Cl.
CPC .......... *A61B 17/8095* (2013.01); *A61B 17/15* (2013.01); *A61B 17/152* (2013.01); (Continued)

(58) Field of Classification Search
CPC ... A61B 17/151; A61B 17/152; A61B 17/155; A61B 17/157; A61B 17/8095; A61B 17/809
See application file for complete search history.

(56) References Cited

U.S. PATENT DOCUMENTS 2,737,724 A    3/1956   Herz
3,579,777 A    5/1971   Milewski
(Continued)

FOREIGN PATENT DOCUMENTS

EP    1669033    6/2006
FR    2 741 525  5/1997
(Continued)

OTHER PUBLICATIONS

Oliver C. Kessler et al., Avoidance of Medical Cortical Fracture in High Tibial Osteotomy: Improved Technique, Clinical Orthopaedics and Related Research, Feb. 2002, pp. 180-185, No. 395.

*Primary Examiner* — Jan Christopher Merene
*Assistant Examiner* — Atiya Mahmud
(74) *Attorney, Agent, or Firm* — Karish & Bjorgum, PC

(57) ABSTRACT

An osteotomy plate for maintaining the spacing of a wedge-like opening in bone, the osteotomy plate comprising: a body having a front side and a back side; a key extending out of the back side of the body for disposition in a keyhole formed in the bone along the wedge-like opening; and a plurality of mounting holes for receiving fixation screws therein, the mounting holes being formed in the body such that when the key is disposed in the keyhole, the mounting holes direct the fixation screws into bone on either side of the wedge-like opening.

6 Claims, 72 Drawing Sheets

Related U.S. Application Data continuation-in-part of application No. 11/047,159, filed on Jan. 31, 2005, now abandoned, and a continuation-in-part of application No. 11/047,551, filed on Jan. 31, 2005, now Pat. No. 8,083,746, and a continuation-in-part of application No. 11/352,103, filed on Feb. 9, 2006, now Pat. No. 8,211,112, and a continuation-in-part of application No. 11/350,333, filed on Feb. 8, 2006, now Pat. No. 8,496,662, and a continuation-in-part of application No. 11/396,490, filed on Apr. 3, 2006, now Pat. No. 8,888,785, and a continuation-in-part of application No. 11/607,321, filed on Dec. 1, 2006, now Pat. No. 7,967,823, and a continuation-in-part of application No. 11/644,218, filed on Dec. 22, 2006, now Pat. No. 7,935,119.

(60) Provisional application No. 60/835,269, filed on Aug. 3, 2006, provisional application No. 60/835,292, filed on Aug. 3, 2006, provisional application No. 60/835,268, filed on Aug. 3, 2006, provisional application No. 60/847,527, filed on Sep. 27, 2006, provisional application No. 60/860,595, filed on Nov. 22, 2006.

(51) Int. Cl.
*A61B 17/15* (2006.01)
*A61B 17/16* (2006.01)
*A61B 17/17* (2006.01)
*A61F 2/30* (2006.01)
*A61B 90/00* (2016.01)

(52) U.S. Cl.
CPC ...... *A61B 17/1615* (2013.01); *A61B 17/1675* (2013.01); *A61B 17/1732* (2013.01); *A61B 17/1764* (2013.01); *A61B 2017/1602* (2013.01); *A61B 2090/034* (2016.02); *A61F 2002/30736* (2013.01)

(56) References Cited

U.S. PATENT DOCUMENTS

| | | |
|---|---|---|
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |
| 4,852,558 A | 8/1989 | Outerbridge |
| 4,936,844 A | 6/1990 | Chandler et al. |
| 5,053,039 A | 10/1991 | Hofmann et al. |
| 5,254,119 A | 10/1993 | Schreiber |
| 5,275,603 A | 1/1994 | Ferrante et al. |
| 5,297,538 A | 3/1994 | Daniel |
| 5,306,276 A | 4/1994 | Johnson et al. |
| 5,352,229 A | 10/1994 | Goble et al. |
| 5,413,579 A | 5/1995 | Du Toit |
| 5,445,640 A | 8/1995 | Johnson et al. |
| 5,451,228 A | 9/1995 | Johnson et al. |
| 5,540,695 A | 7/1996 | Levy |
| 5,569,250 A | 10/1996 | Sarver et al. |
| 5,601,565 A | 2/1997 | Huebner |
| 5,609,635 A | 3/1997 | Michelson |
| 5,609,644 A | 3/1997 | Ashby et al. |
| 5,613,969 A | 3/1997 | Jenkins, Jr. |
| 5,620,448 A | 4/1997 | Puddu |
| 5,640,813 A | 6/1997 | Glazik et al. |
| 5,662,655 A | 9/1997 | Laboureau et al. |
| 5,669,909 A | 9/1997 | Zdeblick et al. |
| 5,674,296 A | 10/1997 | Bryan et al. |
| 5,681,316 A | 10/1997 | DeOrio et al. |
| 5,722,978 A | 3/1998 | Jenkins, Jr. |
| 5,733,290 A | 3/1998 | McCue et al. |
| 5,749,875 A | 5/1998 | Puddu |
| 5,766,251 A | 6/1998 | Koshino |
| 5,843,085 A | 12/1998 | Graser |
| 5,888,223 A | 3/1999 | Bray, Jr. |
| 5,911,724 A | 6/1999 | Wehrli |
| 5,980,526 A | 11/1999 | Johnson et al. |
| 6,008,433 A | 12/1999 | Stone |
| 6,027,504 A | 2/2000 | McGuire |
| 6,039,761 A | 3/2000 | Li et al. |
| 6,086,593 A | 7/2000 | Bonutti |
| 6,099,531 A | 8/2000 | Bonutti |
| 6,102,950 A | 8/2000 | Vaccaro |
| 6,190,390 B1 | 2/2001 | McAllister |
| 6,200,347 B1 | 3/2001 | Anderson et al. |
| 6,203,546 B1 | 3/2001 | MacMahon |
| 6,224,599 B1 | 5/2001 | Baynham et al. |
| 6,277,149 B1 | 8/2001 | Boyle et al. |
| 6,287,308 B1 | 9/2001 | Betz et al. |
| 6,379,361 B1 | 4/2002 | Beck, Jr. et al. |
| 6,423,063 B1 | 7/2002 | Bonutti |
| 6,461,359 B1 | 10/2002 | Tribus et al. |
| 6,478,800 B1 | 11/2002 | Fraser et al. |
| 6,544,266 B1 | 4/2003 | Roger et al. |
| 6,565,570 B2 | 5/2003 | Sterett et al. |
| 6,575,982 B1 | 6/2003 | Bonutti |
| 6,755,841 B2 | 6/2004 | Fraser et al. |
| 6,780,186 B2 | 8/2004 | Errico et al. |
| 6,796,986 B2 | 9/2004 | Duffner |
| 6,823,871 B2 | 11/2004 | Schmieding |
| 2002/0010513 A1 | 1/2002 | Schmieding |
| 2002/0029084 A1 | 3/2002 | Paul et al. |
| 2002/0095156 A1 | 7/2002 | Kuras et al. |
| 2003/0028197 A1 | 2/2003 | Hanson et al. |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0195632 A1 | 10/2003 | Foley et al. |
| 2003/0199875 A1* | 10/2003 | Mingozzi ........... A61B 17/8095 606/297 |
| 2003/0199881 A1 | 10/2003 | Bonutti |
| 2004/0039387 A1 | 2/2004 | Gause et al. |
| 2004/0249377 A1 | 12/2004 | Kaes et al. |
| 2005/0075641 A1 | 4/2005 | Singhatat et al. |
| 2005/0216090 A1 | 9/2005 | O'Driscoll et al. |
| 2005/0228498 A1 | 10/2005 | Andres |
| 2005/0251147 A1 | 11/2005 | Novak |
| 2005/0273114 A1 | 12/2005 | Novak |
| 2005/0273115 A1 | 12/2005 | Coon et al. |
| 2006/0106396 A1 | 5/2006 | Justin et al. |
| 2006/0122617 A1 | 6/2006 | Lavallee et al. |
| 2006/0129163 A1 | 6/2006 | McGuire |
| 2006/0149274 A1 | 7/2006 | Justin et al. |
| 2006/0149275 A1 | 7/2006 | Cadmus |
| 2006/0235403 A1 | 10/2006 | Blain |
| 2006/0241636 A1 | 10/2006 | Novak et al. |
| 2007/0191850 A1* | 8/2007 | Kim .................. A61B 17/0642 606/75 |

FOREIGN PATENT DOCUMENTS

| | | |
|---|---|---|
| WO | WO 2005/048888 | 6/2005 |
| WO | WO 2006/107800 | 10/2006 |

* cited by examiner

TOP VIEW

LATERAL VIEW UNDER FLUOROSCOPY, WITH GUIDE ELEMENT NOT VERTICALLY ALIGNED WITH FLUOROSCOPE

LATERAL VIEW UNDER FLUOROSCOPY, WITH GUIDE ELEMENT VERTICALLY ALIGNED WITH FLUOROSCOPE

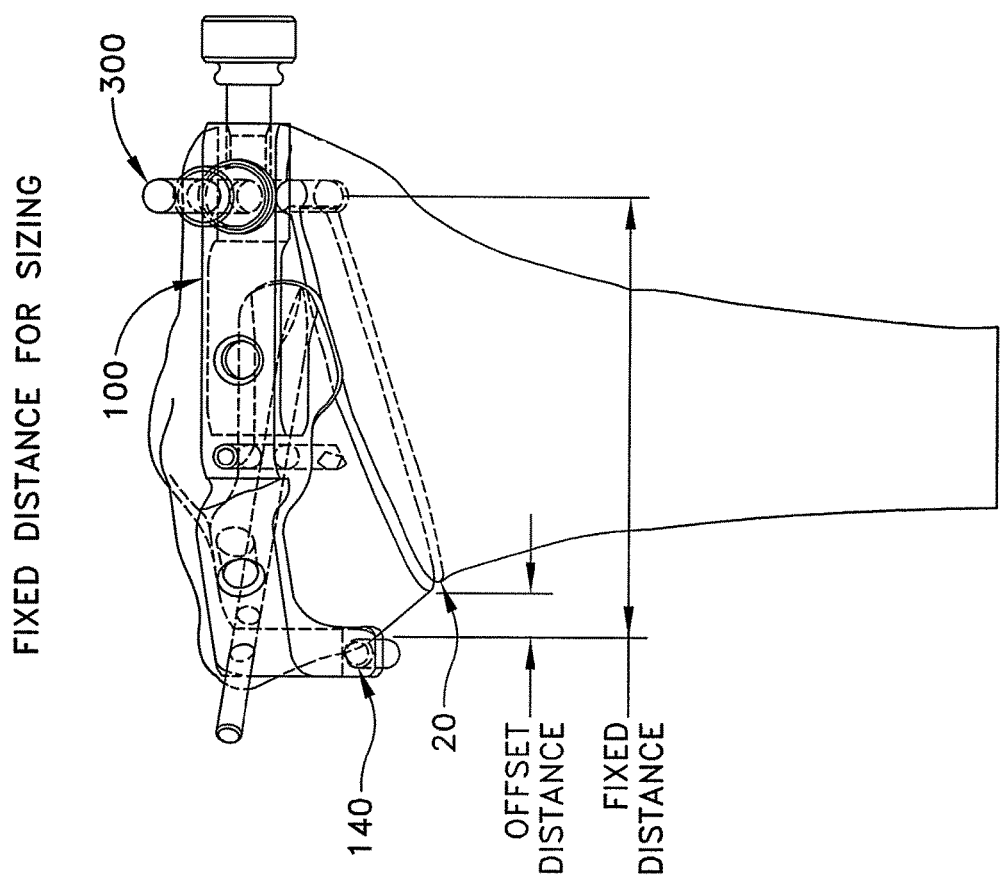

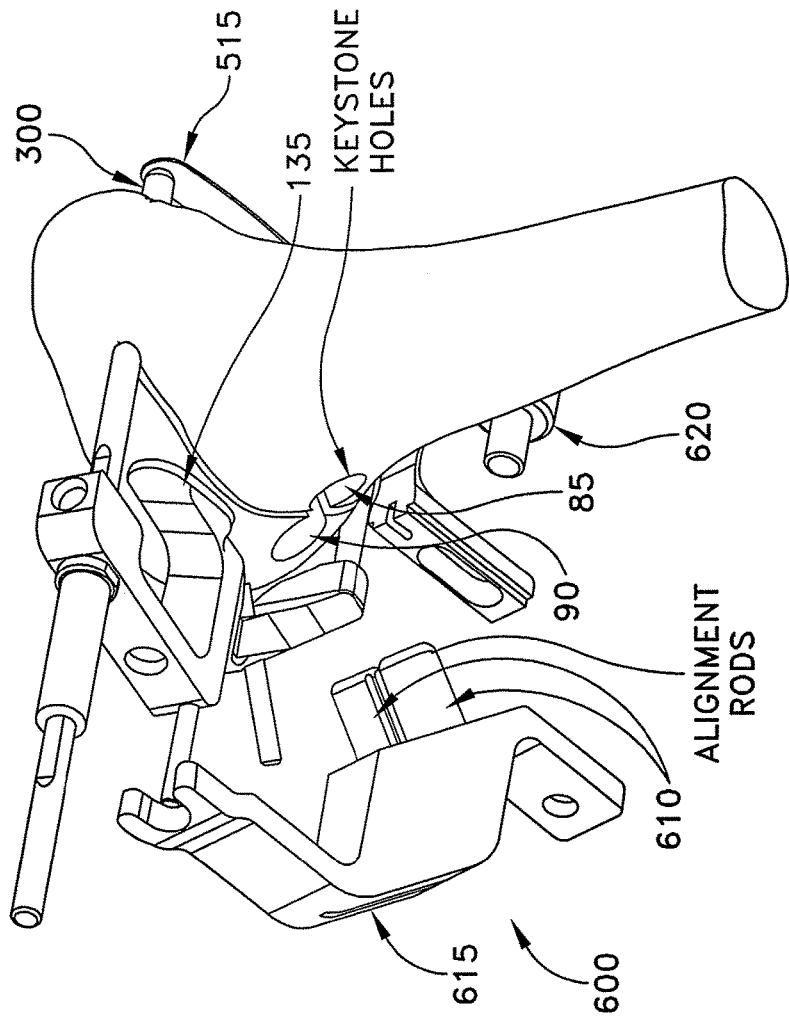
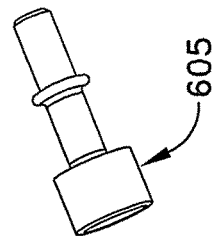
FIG. 21

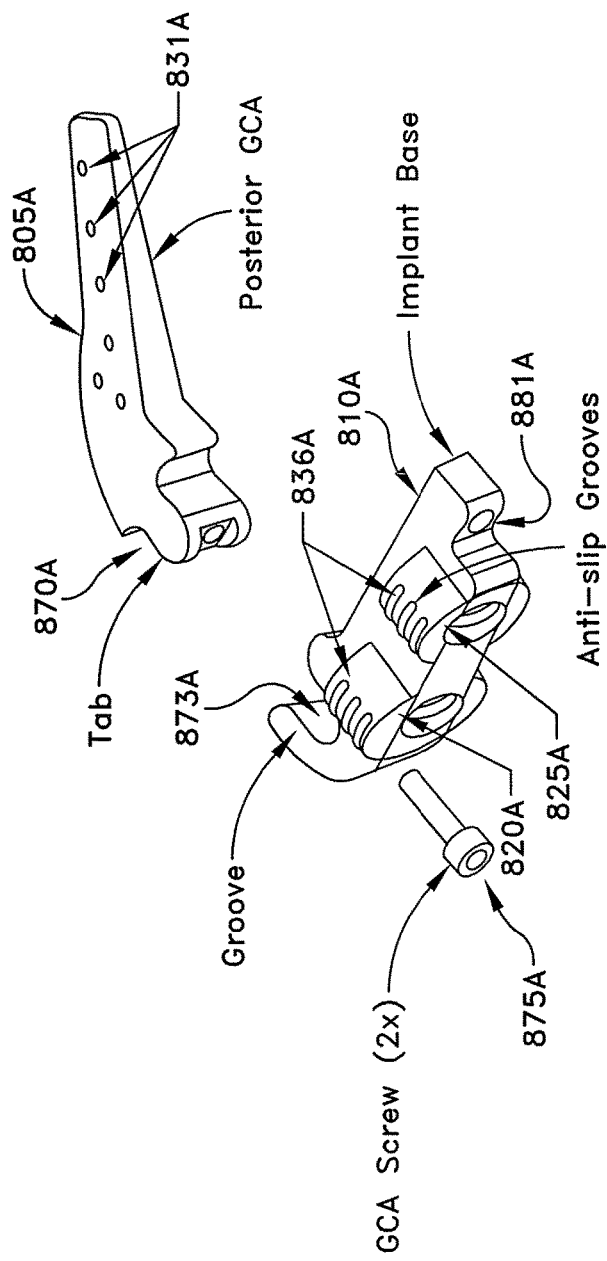
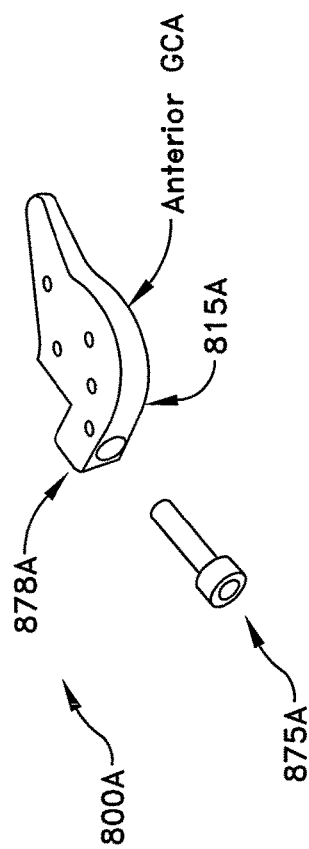
FIG. 32

APPARATUS FOR PERFORMING AN OPEN WEDGE, HIGH TIBIAL OSTEOTOMY

REFERENCE TO PENDING PRIOR PATENT APPLICATIONS

This patent application is a continuation of U.S. patent application Ser. No. 11/890,129, filed Aug. 3, 2007, which:

(i) is a continuation-in-part of U.S. patent application Ser. No. 11/047,159, filed Jan. 31, 2005;

(ii) is a continuation-in-part of U.S. patent application Ser. No. 11/047,551, filed Jan. 31, 2005, now U.S. Pat. No. 8,083,746;

(iii) is a continuation-in-part of U.S. patent application Ser. No. 11/352,103, filed Feb. 9, 2006, now U.S. Pat. No. 8,211,112;

(iv) is a continuation-in-part of U.S. patent application Ser. No. 11/350,333, filed Feb. 8, 2006, now U.S. Pat. No. 8,496,662;

(v) is a continuation-in-part of U.S. patent application Ser. No. 11/396,490, filed Apr. 3, 2006, now allowed;

(vi) is a continuation-in-part of U.S. patent application Ser. No. 11/607,321, filed Dec. 1, 2006, now U.S. Pat. No. 7,967,823;

(vii) is a continuation-in-part of U.S. patent application Ser. No. 11/644,218, filed Dec. 22, 2006, now U.S. Pat. No. 7,935,119;

(viii) is a continuation-in-part of U.S. patent application Ser. No. 11/888,719, filed Aug. 2, 2007, now abandoned;

(ix) claims the benefit of U.S. Provisional Patent Application Ser. No. 60/835,269, filed Aug. 3, 2006;

(x) claims the benefit of U.S. Provisional Patent Application Ser. No. 60/835,292, filed Aug. 3, 2006;

(xi) claims the benefit of U.S. Provisional Patent Application Ser. No. 60/835,268, filed Aug. 3, 2006;

(xii) claims the benefit of U.S. Provisional Patent Application Ser. No. 60/847,527, filed Sep. 27, 2006; and (xiii) claims the benefit of U.S. Provisional Patent Application Ser. No. 60/860,595, filed Nov. 22, 2006.

The above-identified patent applications are hereby incorporated herein by reference in their entireties.

FIELD OF THE INVENTION

This invention relates to surgical methods and apparatus in general, and more particularly to surgical methods and apparatus for performing open wedge, high tibial osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are essentially two ways in which to adjust the orientation of the tibia: (i) the closed wedge technique; and (ii) the open wedge technique.

With the closed wedge technique, a wedge of bone is removed from the upper portion of the tibia, and then the tibia is manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon. Among other things, with respect to open wedge osteotomies, it can be difficult to create the wedge-like opening in the bone with the necessary precision and with a minimum of trauma to the surrounding tissue (e.g., the neurological and vascular structures at the back of the knee). Furthermore, with open wedge osteotomies, it can be difficult to stabilize the upper and lower portions of the tibia relative to one another and to maintain them in this position while healing occurs.

The present invention is directed to open wedge, high tibial osteotomies of the knee, and is intended to provide increased precision and reduced trauma when creating the wedge-shaped opening in the bone, and to provide increased stability to the upper and lower portions of the tibia while healing occurs.

SUMMARY OF THE INVENTION

The present invention comprises a novel method and apparatus for performing an open wedge, high tibial osteotomy. More particularly, the present invention comprises the provision and use of a novel method and apparatus for forming an appropriate osteotomy cut into the upper portion of the tibia, manipulating the tibia so as to open an appropriate wedge-like opening in the tibia, and then mounting an appropriately-shaped implant at the wedge-like opening in the tibia, so as to stabilize the tibia with the desired orientation, whereby to reorient the lower portion of the tibia relative to the tibial plateau and hence adjust the manner in which load is transferred from the femur to the tibia.

In one form of the present invention, there is provided an osteotomy plate for maintaining the spacing of a wedge-like opening in bone, the osteotomy plate comprising:

a body having a front side and a back side;

a key extending out of the back side of the body for disposition in a keyhole formed in the bone along the wedge-like opening; and a plurality of mounting holes for receiving fixation screws therein, the mounting holes being formed in the body such that when the key is disposed in the keyhole, the mounting holes direct the fixation screws into bone on either side of the wedge-like opening.

In another form of the present invention, there is provided a method for performing an osteotomy, the method comprising:

forming a keyhole in a bone;

forming an osteotomy cut in the bone through the keyhole;

opening the bone so as to form a wedge-like opening;

providing an osteotomy plate, wherein the osteotomy plate comprises:

a body having a front side and a back side;
a key extending out of the back side of the body for disposition in the keyhole formed in the bone; and
a plurality of mounting holes for receiving fixation screws therein, the mounting holes being formed in the body such that when the key is disposed in the keyhole, the mounting holes direct fixation screws into the bone on either side of the wedge-like opening;
positioning the osteotomy plate so that the back side of the osteotomy plate is positioned against the bone and the key is disposed in the keyhole formed in the bone; and
passing fixation screws through the mounting holes formed in the osteotomy plate and into the bone so as to secure the osteotomy plate to the bone.

In yet another form of the present invention, there is provided an osteotomy plate for maintaining the spacing of a wedge-like opening in bone, the osteotomy plate comprising:
a body having a front side and a back side;
a plurality of mounting holes for receiving fixation screws therein, the mounting holes being formed in the body such that when the osteotomy plate is positioned against the bone, the mounting holes direct fixation screws into the bone on either side of the wedge-like opening; and
a plurality of bosses extending out of the back side of the body.

In still another form of the present invention, there is provided a method for performing an osteotomy, the method comprising:
forming a plurality of boss holes in a bone;
forming an osteotomy cut in the bone between the boss holes;
opening the bone so as to form a wedge-like opening;
providing an osteotomy plate, wherein the osteotomy plate comprises:
a body having a front side and a back side;
a plurality of mounting holes for receiving fixation screws therein, the mounting holes being formed in the body such that when the osteotomy plate is positioned against the bone, the mounting holes direct fixation screws into the bone on either side of the wedge-like opening; and
a plurality of bosses extending out of the back side of the body;
positioning the osteotomy plate so that the back side of the osteotomy plate is positioned against the bone and the bosses are disposed in the boss holes formed in the bone; and
passing fixation screws through the mounting holes formed in the osteotomy plate and into the bone so as to secure the osteotomy plate to the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 10-30 are schematic views showing a preferred method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia;

FIGS. 31-33 are schematic views showing an alternative wedge-shaped implant also formed in accordance with the present invention;

DETAILED DESCRIPTION OF THE PREFERRED EMBODIMENTS

Overview of an Open Wedge, High Tibial Osteotomy

Figure 1:
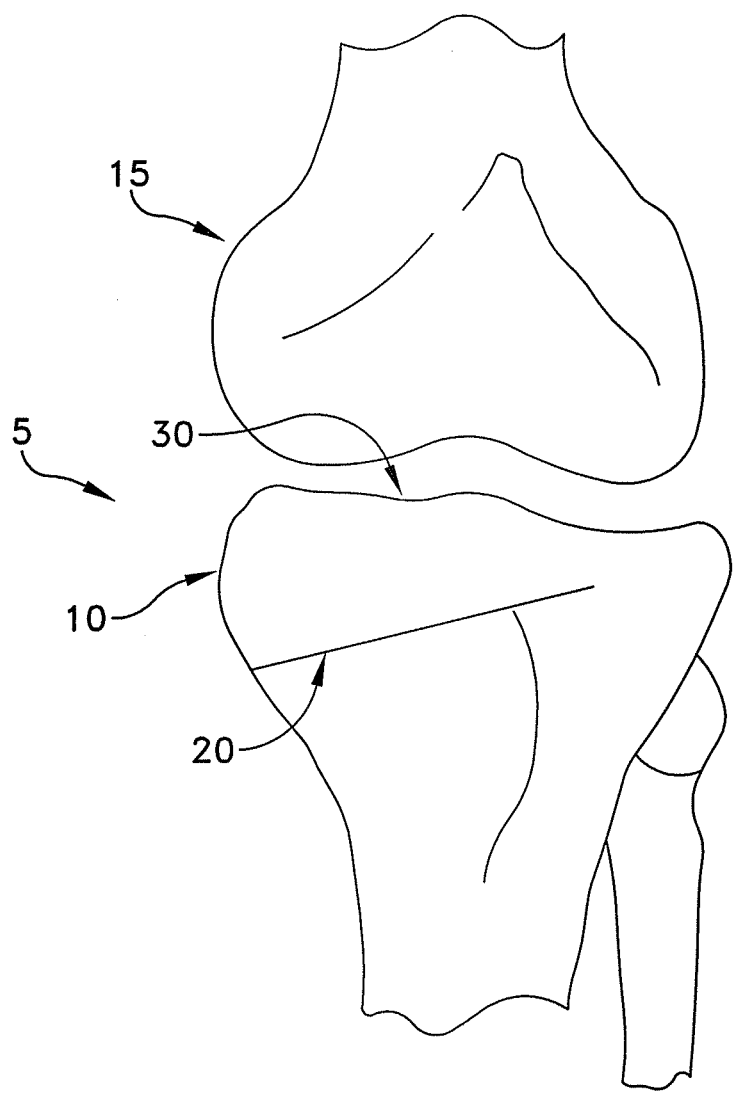
FIGS. 1-3 are schematic views showing the formation of a wedge-like opening in the tibia for an open wedge, high tibial osteotomy, and positioning of a wedge-shaped implant into the wedge-like opening in the tibia.
Figure 2:
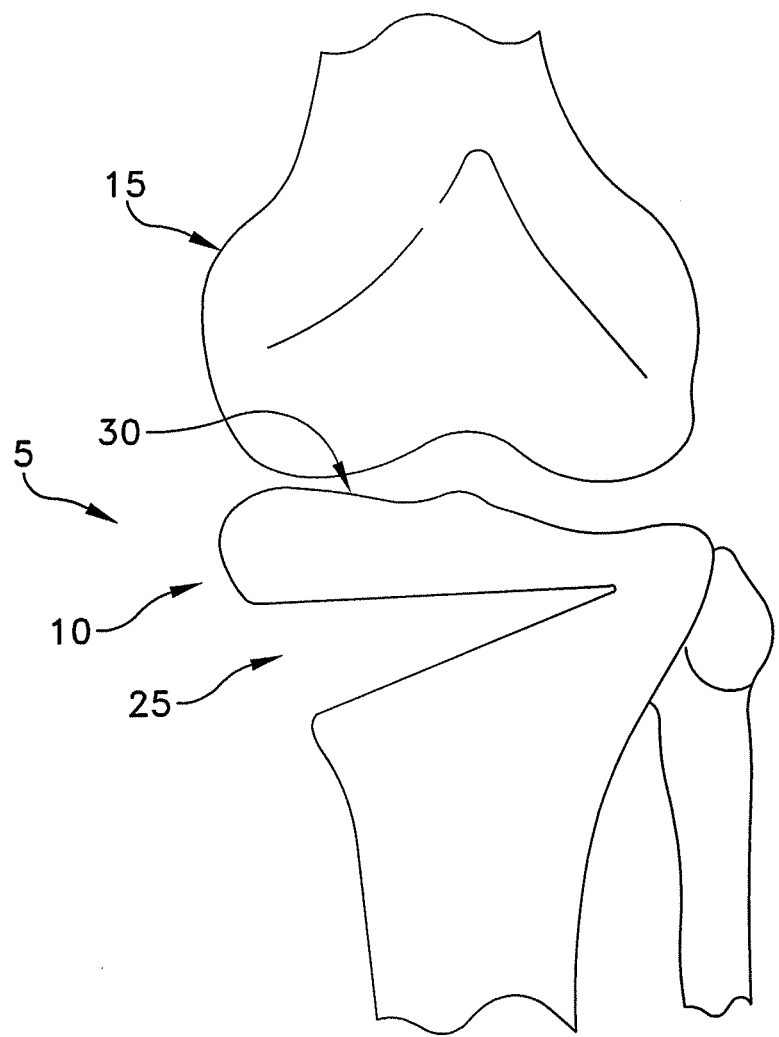
Figure 3:
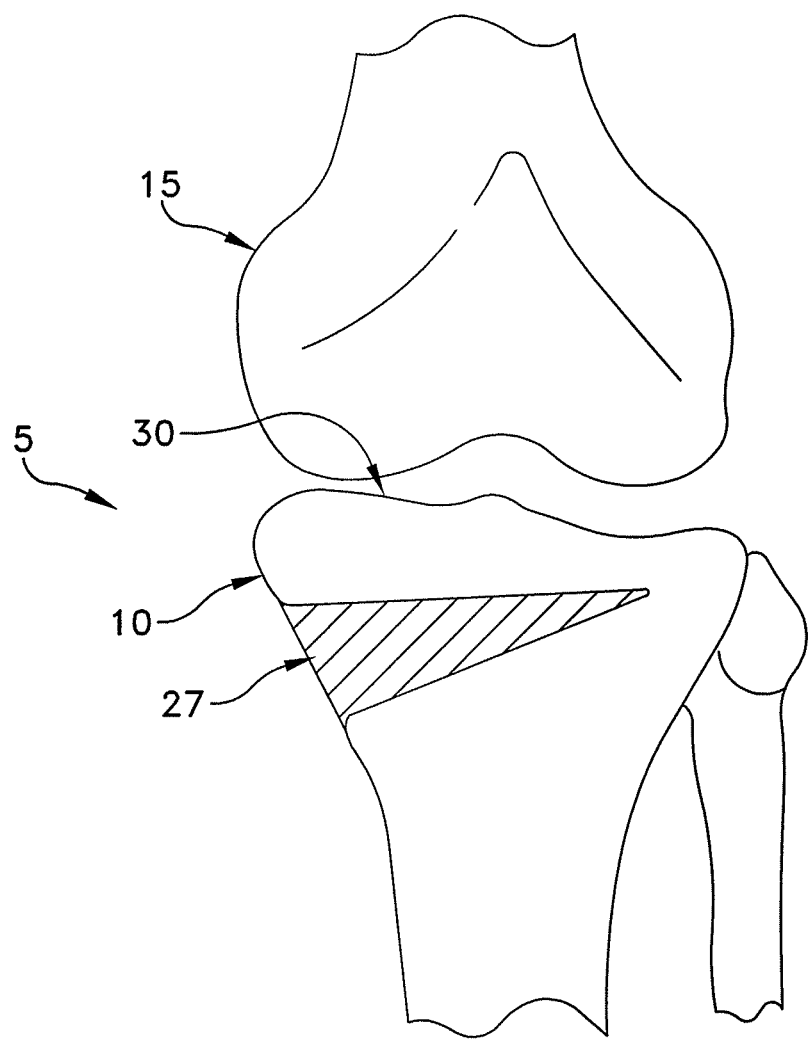

Looking first at FIGS. 1-3, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then manipulating the lower portion of the tibia so as to open a wedge-like opening 25 (FIG. 2) in the bone, with the wedge-like opening 25 being configured so as to adjust the manner in which load is transferred from the femur to the tibia. In this respect, it should be appreciated that a variety of methods are well known in the art for determining the degree of correction necessary to correctly re-align the weight-bearing axis of the knee. Furthermore, cut 20 and wedge-like opening 25 may be formed in a variety of ways well known in the art.

Among other things, the present invention provides a new and improved method and apparatus for forming cut 20 and wedge-like opening 25, as will be discussed in detail below.

Once the desired wedge-like opening 25 has been formed in tibia 10 so as to reconfigure tibia 10 to the desired geometry, the bone may be secured in position in a variety of ways well known in the art (e.g., by screwing metal plates to the bone or by inserting a wedge-shaped implant into the opening in the bone), whereby to adjust the manner in which the load is transferred from the femur to the tibia. By way of example, FIG. 3 shows a wedge-shaped implant 27 inserted into the wedge-like opening 25 formed in the tibia, whereby to stabilize the tibia in its reconfigured geometry.

Among other things, the present invention also provides a new and improved implant, and an associated method and apparatus for deploying the same at the wedge-shaped opening in the tibia, as will be discussed in detail below.

Figure 3A:
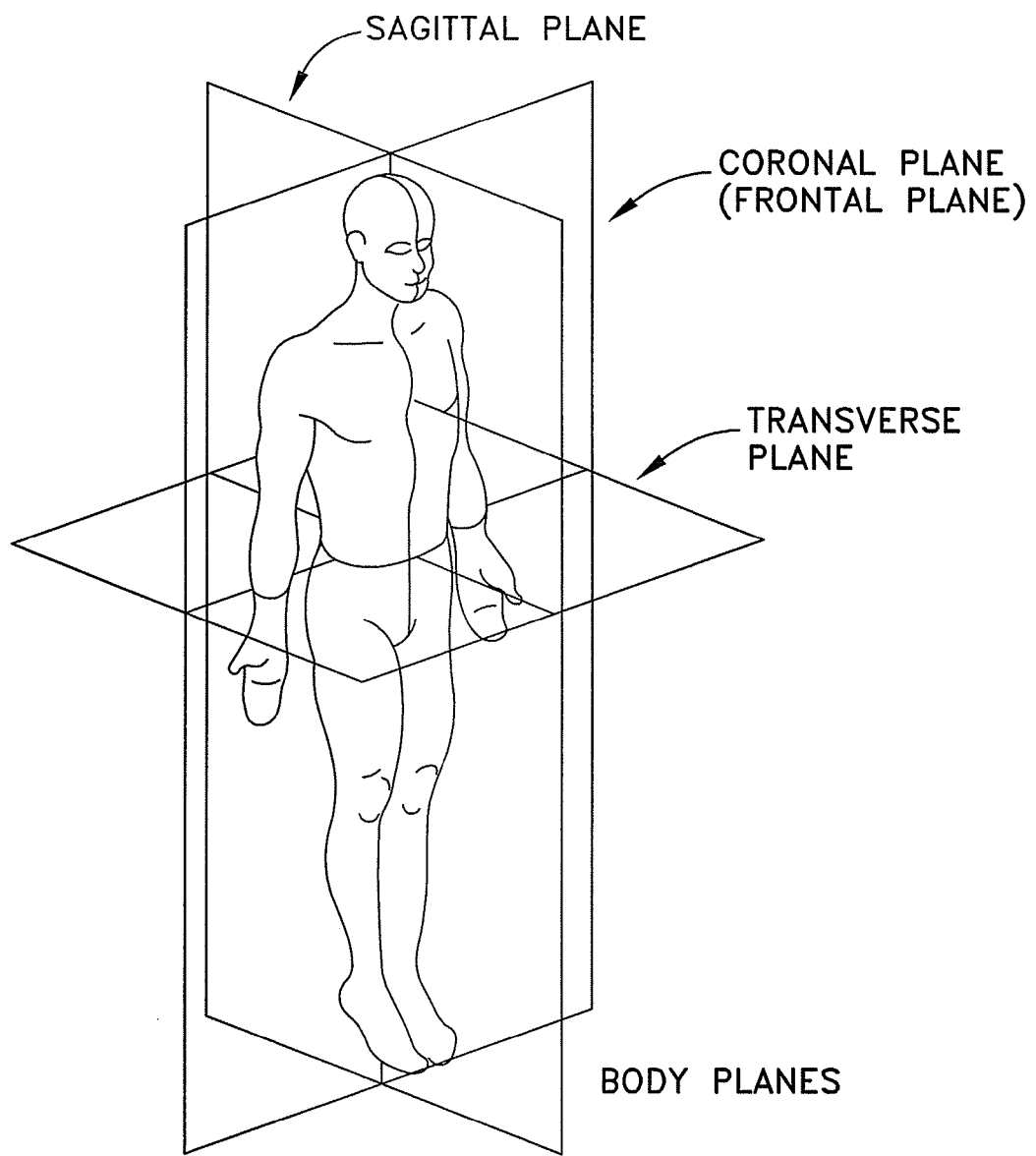
FIG. 3A is a schematic view showing selected anatomical planes.

Discussion of the Relevant Planar Surfaces in the Open Wedge, High Tibial Osteotomy of the Present Invention In order to appreciate certain aspects of the present invention, it is helpful to have a thorough understanding of the planar surfaces of the tibia that are relevant in performing the open wedge, high tibial osteotomy of the present invention. Thus, the following discussion presents a geometric description of the planar surfaces that are relevant to the open wedge, high tibial osteotomy of the present invention. For the purposes of the present discussion, it can sometimes be helpful to make reference to selected anatomical planes, e.g., the coronal plane, the sagittal plane and the transverse plane (FIG. 3A).

Figure 4:
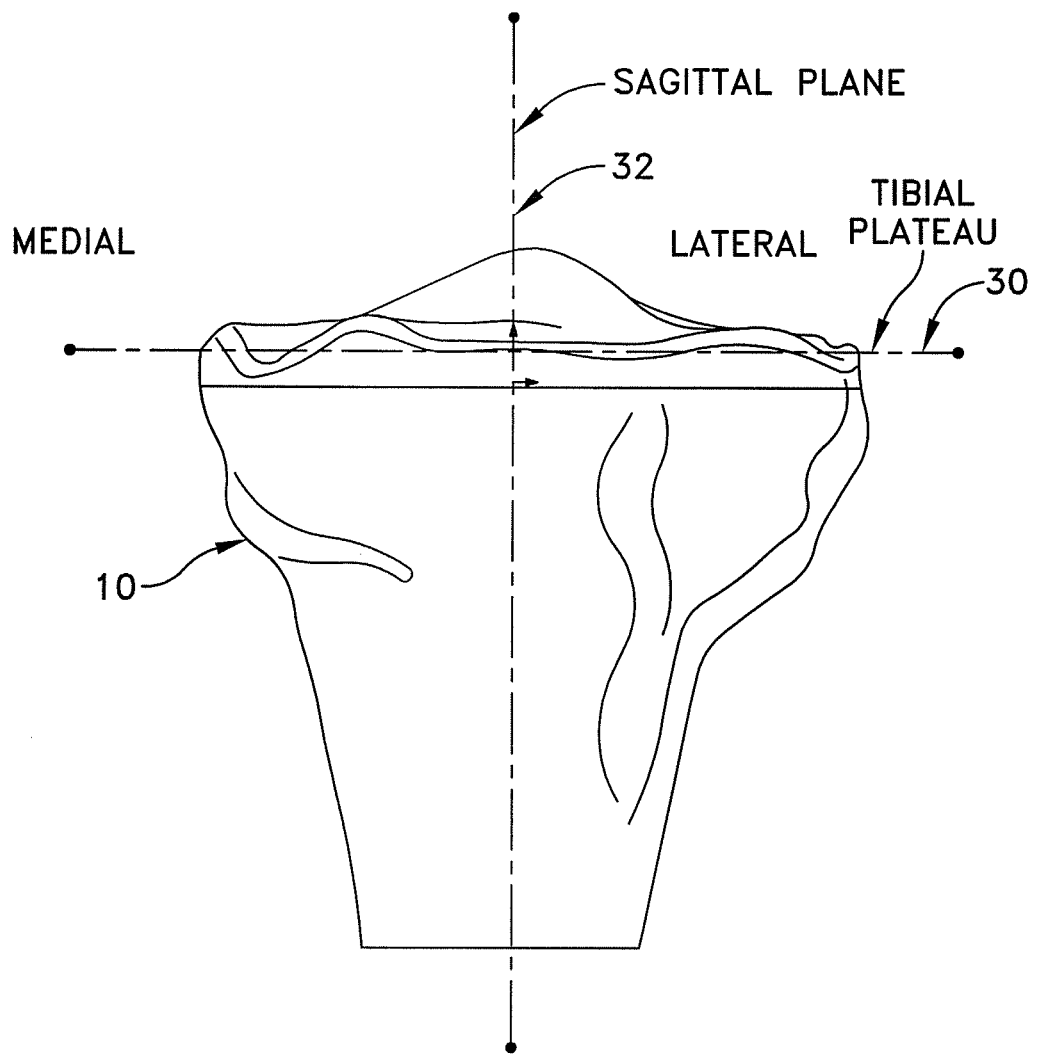
FIGS. 4-9 show the relevant planar surfaces in an open wedge, high tibial osteotomy conducted in accordance with the present invention.
Figure 5:
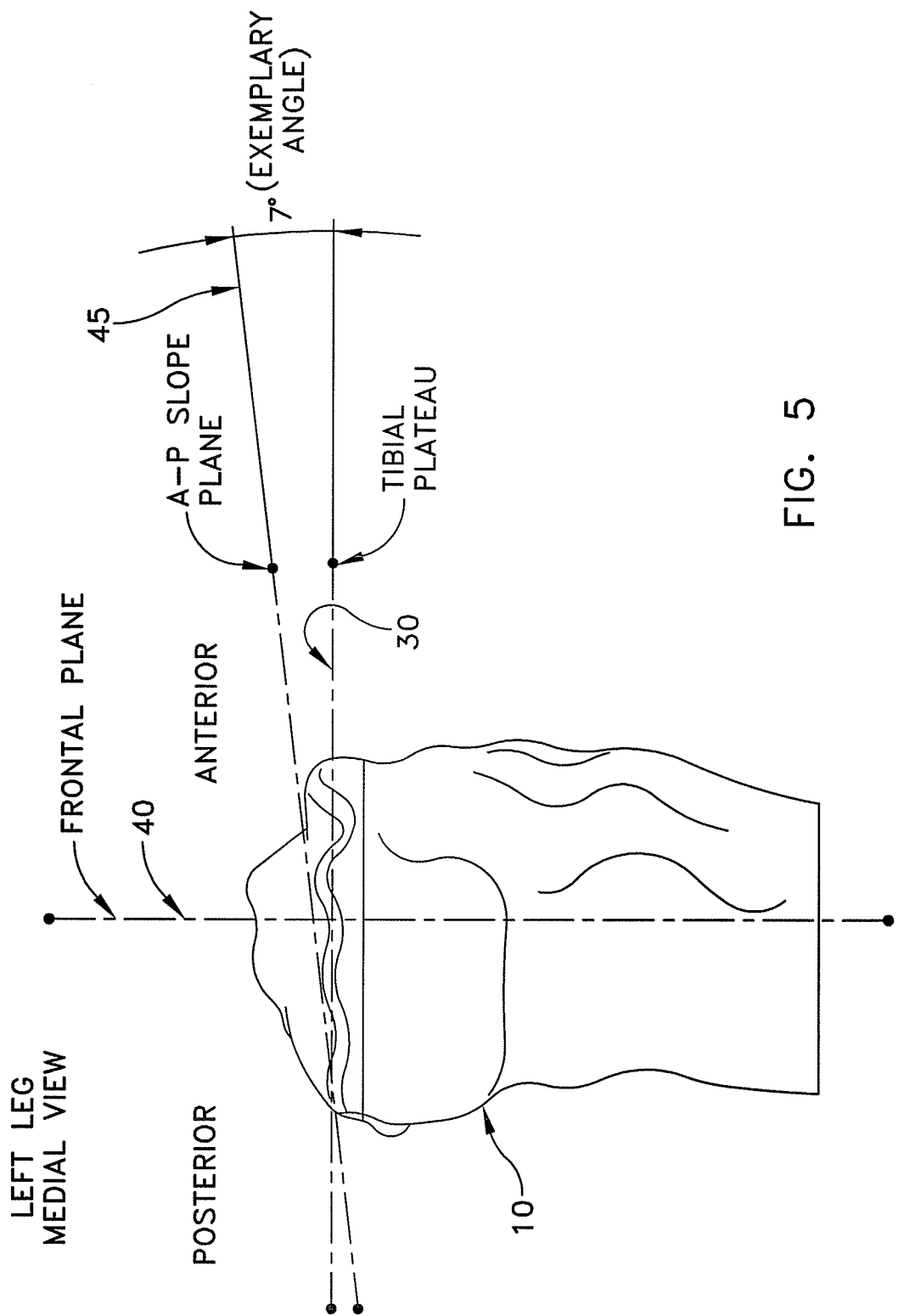

Looking now at FIGS. 1-4, for the purposes of the present invention, the tibial plateau 30 may be described as a horizontal (or transverse) plane that extends along the top surface of tibia 10. For reference, the sagittal plane 32 is also shown in FIG. 4. As seen in FIG. 5, tibial plateau 30 is also perpendicular to the frontal (or coronal) plane 40. The anterior-posterior (A-P) slope is defined by an anterior-posterior (A-P) slope plane 45 that extends along the sloping top surface of the tibia, from anterior-to-posterior. Published research has demonstrated that the anterior-posterior (A-P) slope typically extends at an angle of approximately 7.degree. to 11.degree. to the tibial plateau 30; however, the specific angle may vary from individual to individual.

Figure 6:
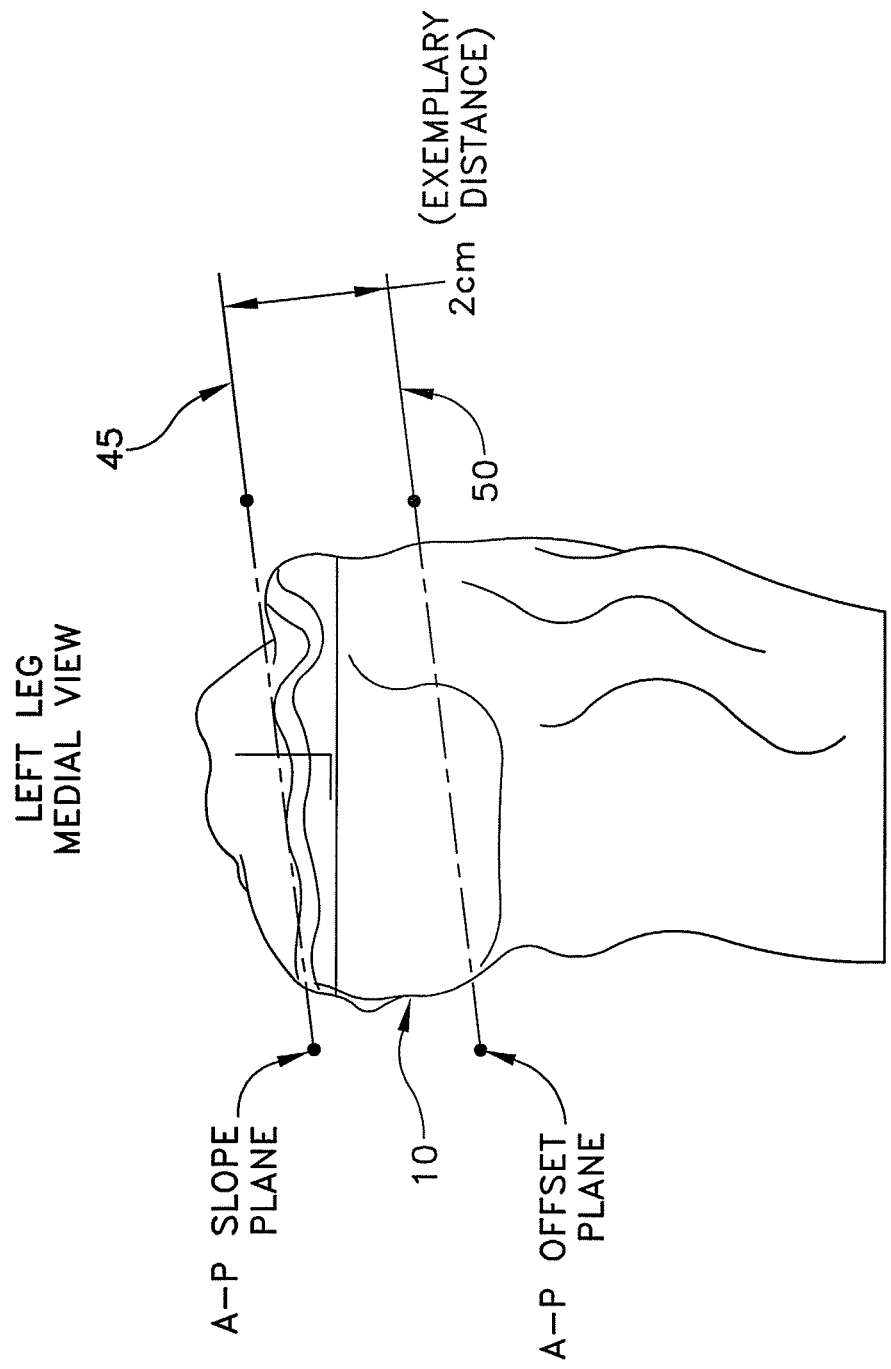

Looking next at FIG. 6, for the open wedge, high tibial osteotomy of the present invention, it is generally desirable to stay about 2 cm inferior to the A-P slope plane 45. This offset can be referred to as the A-P offset plane 50.

Figure 7:
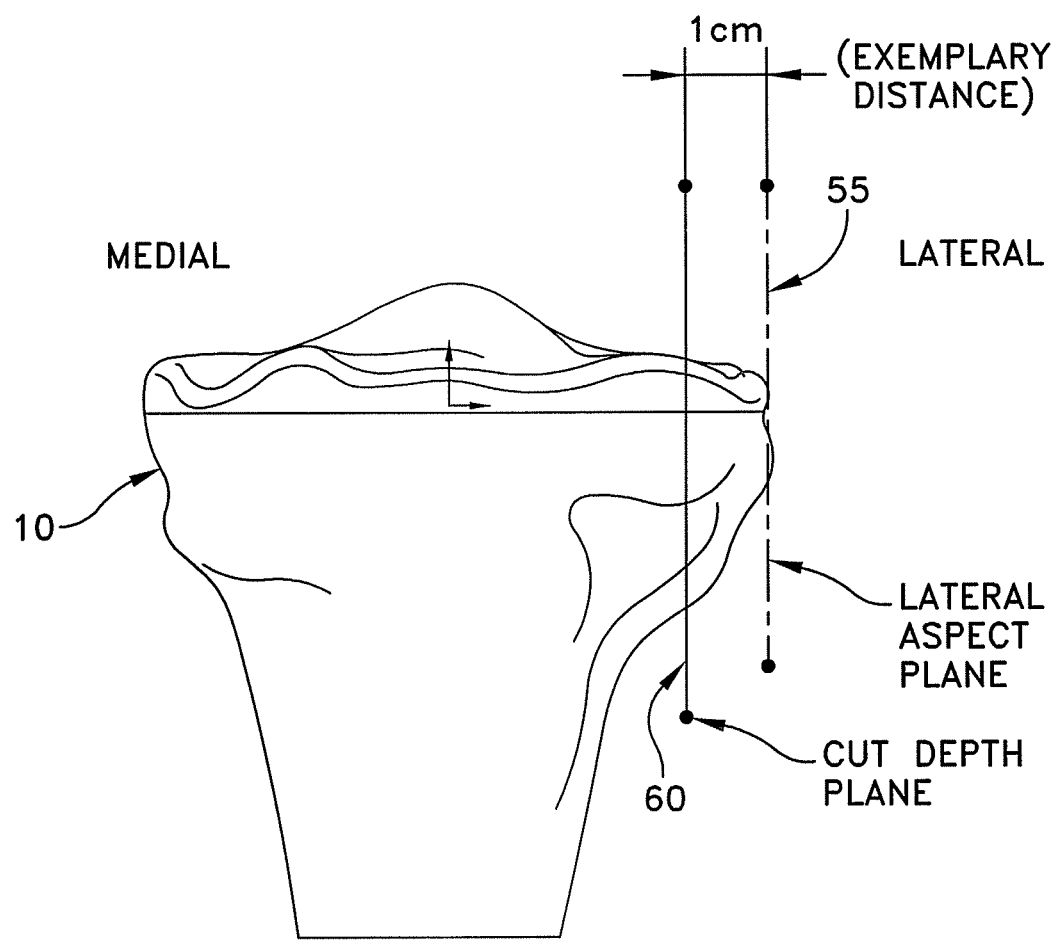

As seen in FIG. 7, the lateral aspect and cut depth of the cut 20 may be defined by a lateral aspect plane 55 and a cut depth plane 60, with the cut depth being about 1 cm medial to the lateral aspect of the tibia.

Figure 8:
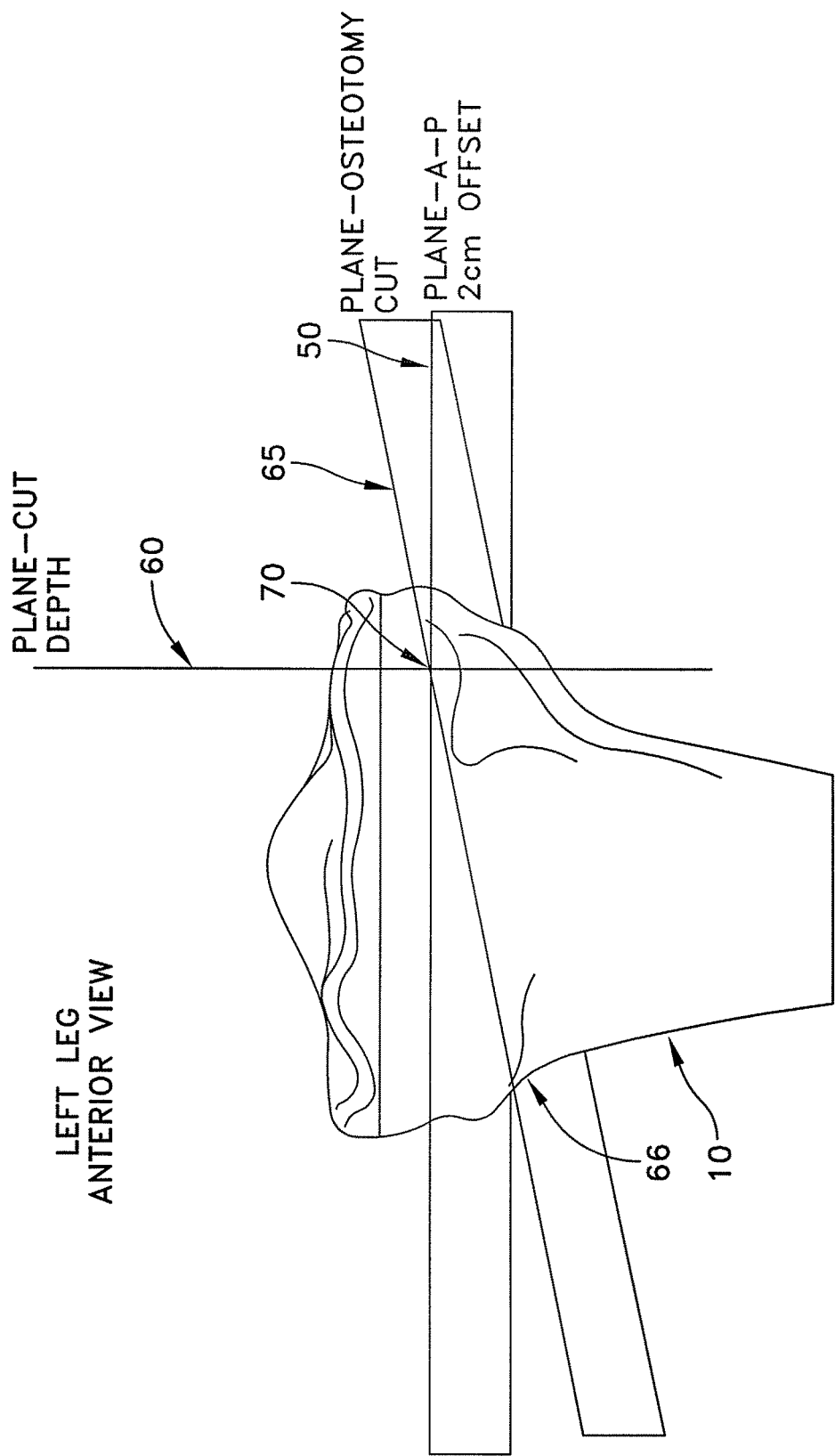

Looking next at FIG. 8, the osteotomy cut plane 65 (when seen from the direct frontal view of FIG. 8) is formed by a plane that is rotated away from the A-P offset plane 50 through an axis which is formed by the intersection of the cut depth plane 60 and the A-P offset plane 50. The degree of rotation is selected so as to be sufficient to place the entry of the osteotomy cut plane 65 at the medial neck 66 (FIG. 8) of the tibia. It should be noted that the A-P offset plane 50 and the osteotomy cut plane 65 are "tilted" slightly from anterior to posterior (but not seen in the direct frontal view of FIG. 8), since the A-P offset plane 50 and the osteotomy cut plane 65 follow the tilt of the A-P slope plane 45 (FIG. 6). The intersection of the A-P offset plane 50 and the cut depth plane 60 forms an axis 70 which, in accordance with the present invention, defines the lateral limit of the osteotomy cut 20. In other words, axis 70 defines a line through the tibia which is (i) parallel to A-P slope plane 45, and (ii) contained within osteotomy cut plane 65. Furthermore, in accordance with the present invention, axis 70 is used to define the lateral limit of the osteotomy cut 20 which is to be made into the tibia.

Figure 9:
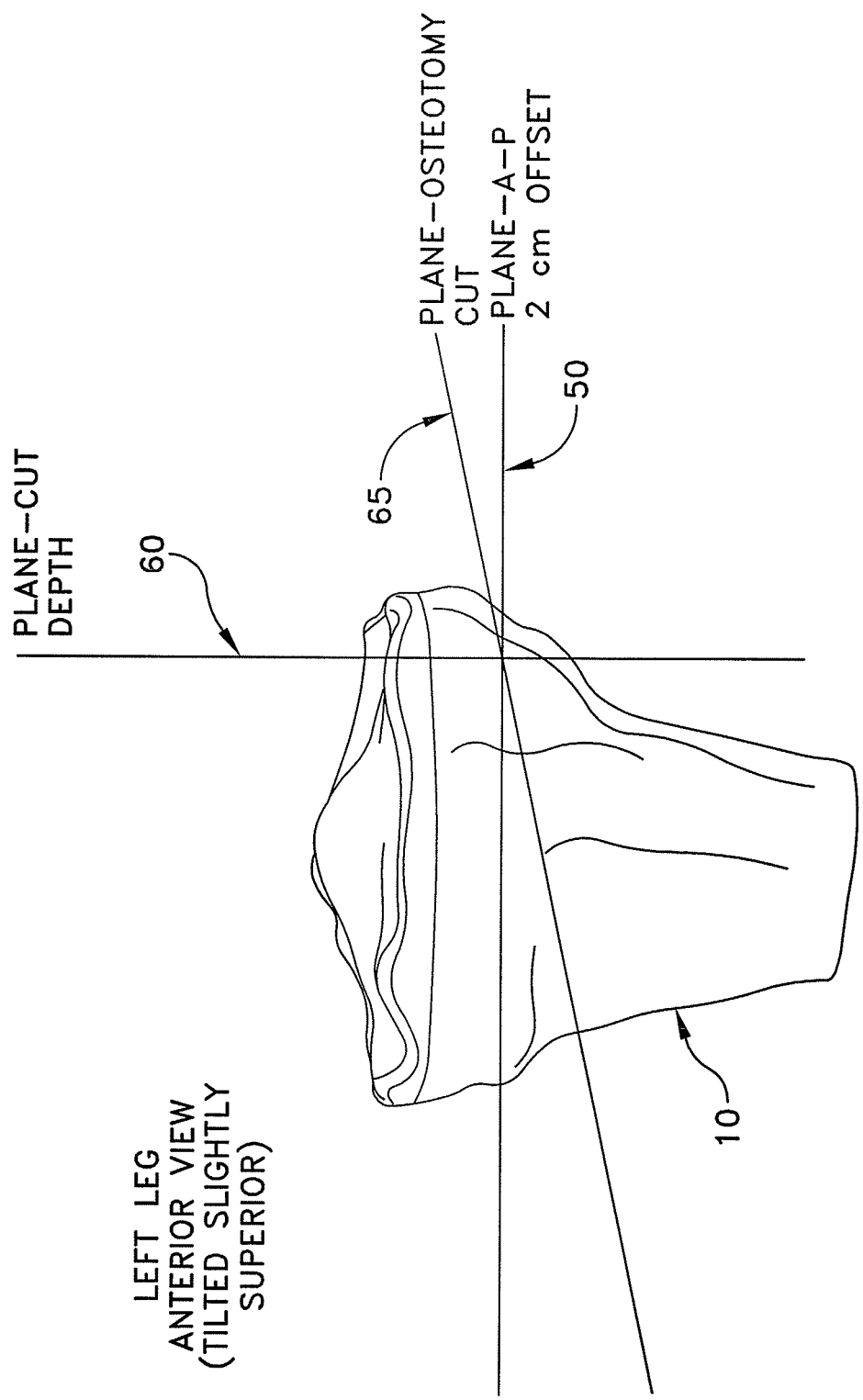

FIG. 9 is a direct view taken along the osteotomy cut plane. This view is tilted downward (e.g., at an angle of approximately 7.degree.) from the direct frontal view of FIG. 8. Again, the angle of tilt downward is equal to the A-P slope. In other words, with the present invention, the osteotomy cut plane 65 extends parallel to the A-P slope plane 45 (in the anterior-to-posterior direction, although not in the medial-to-lateral direction), and typically slopes downward (e.g., at an angle of approximately 7-11.degree.) when viewed in the anterior-to-posterior direction. Furthermore, with the present invention, the axis 70 (which defines the lateral limit to the osteotomy cut 20) is contained within the osteotomy cut plane 65.

Figure 16:
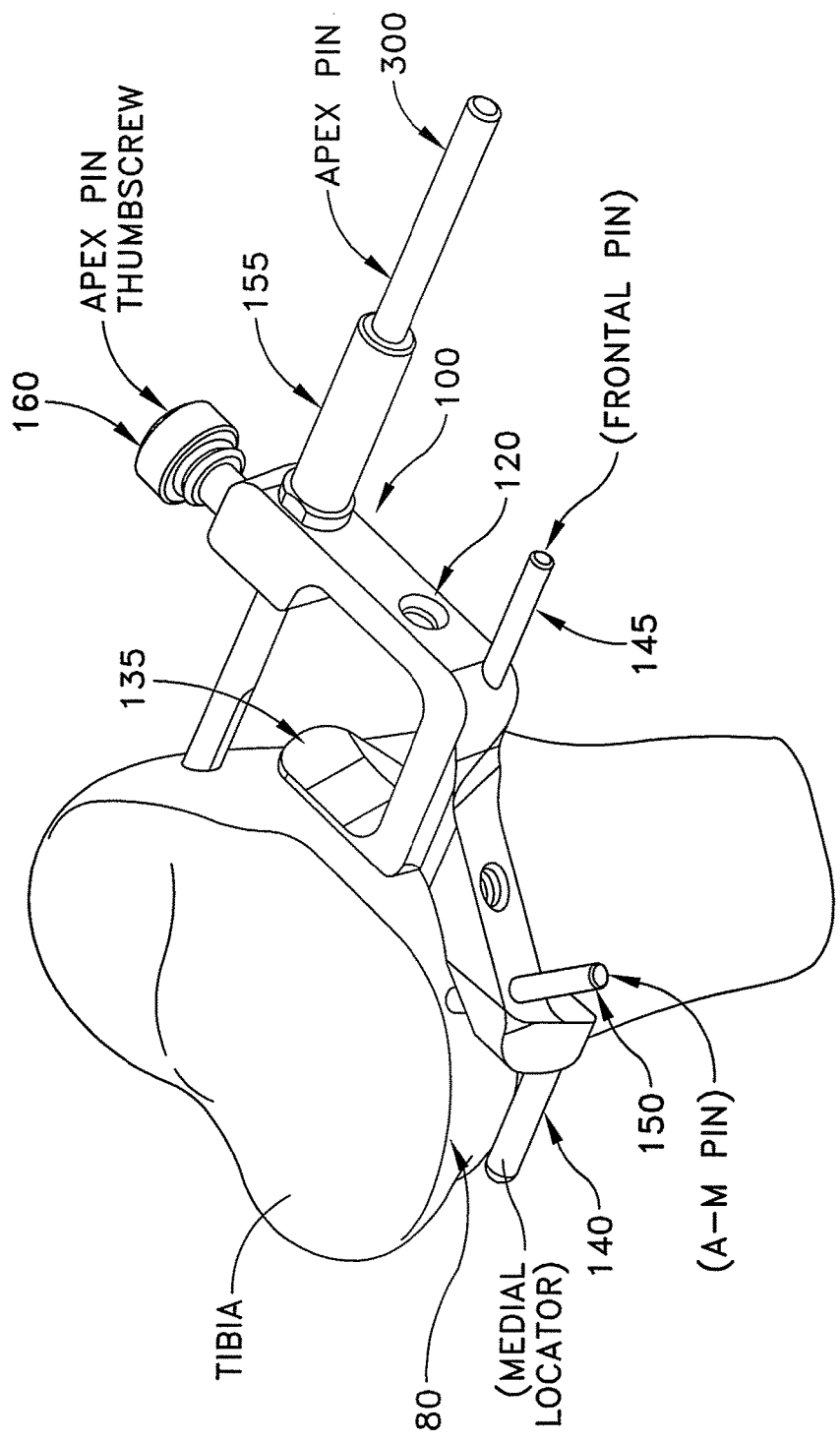
Figure 18:
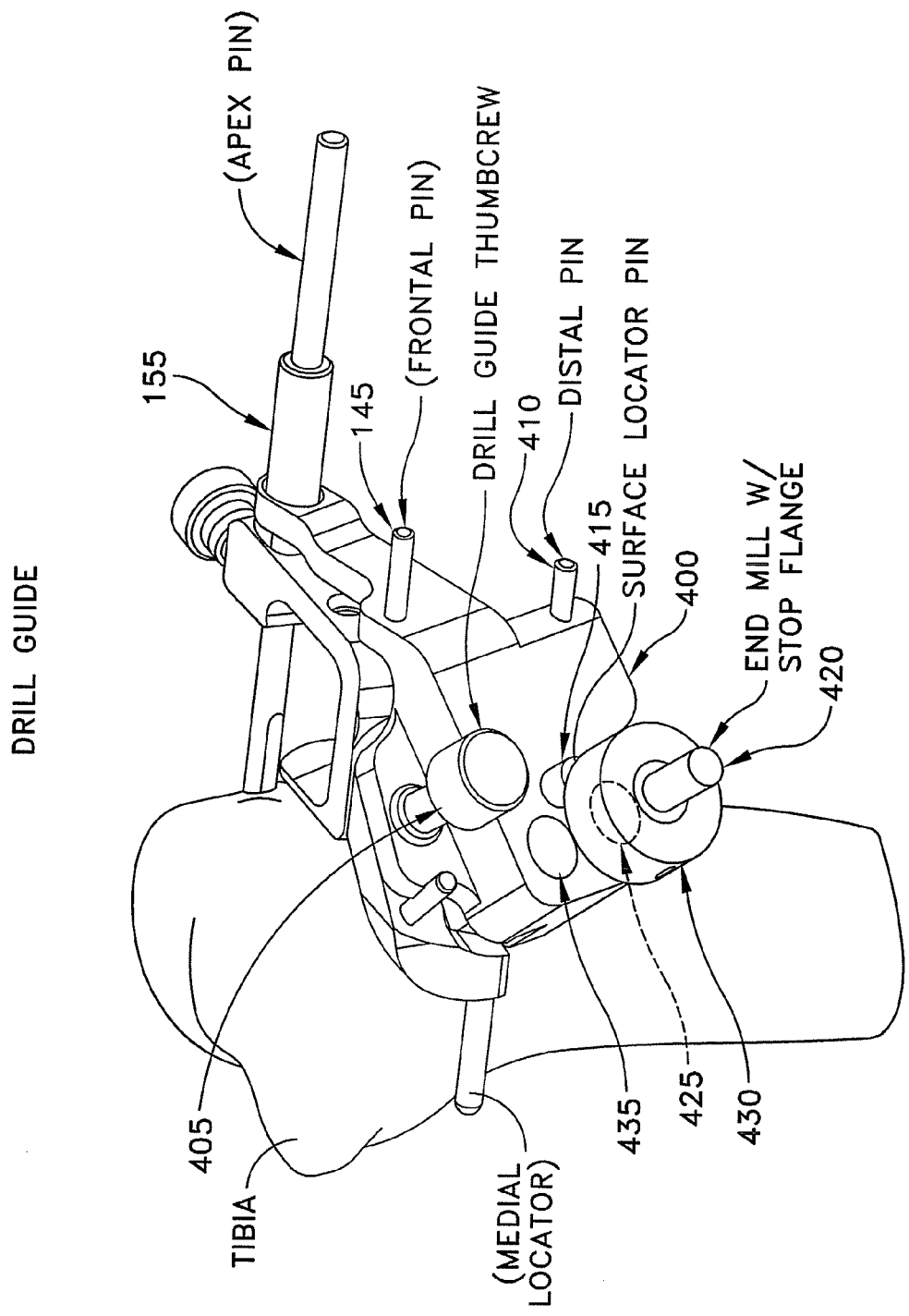
Figure 19:
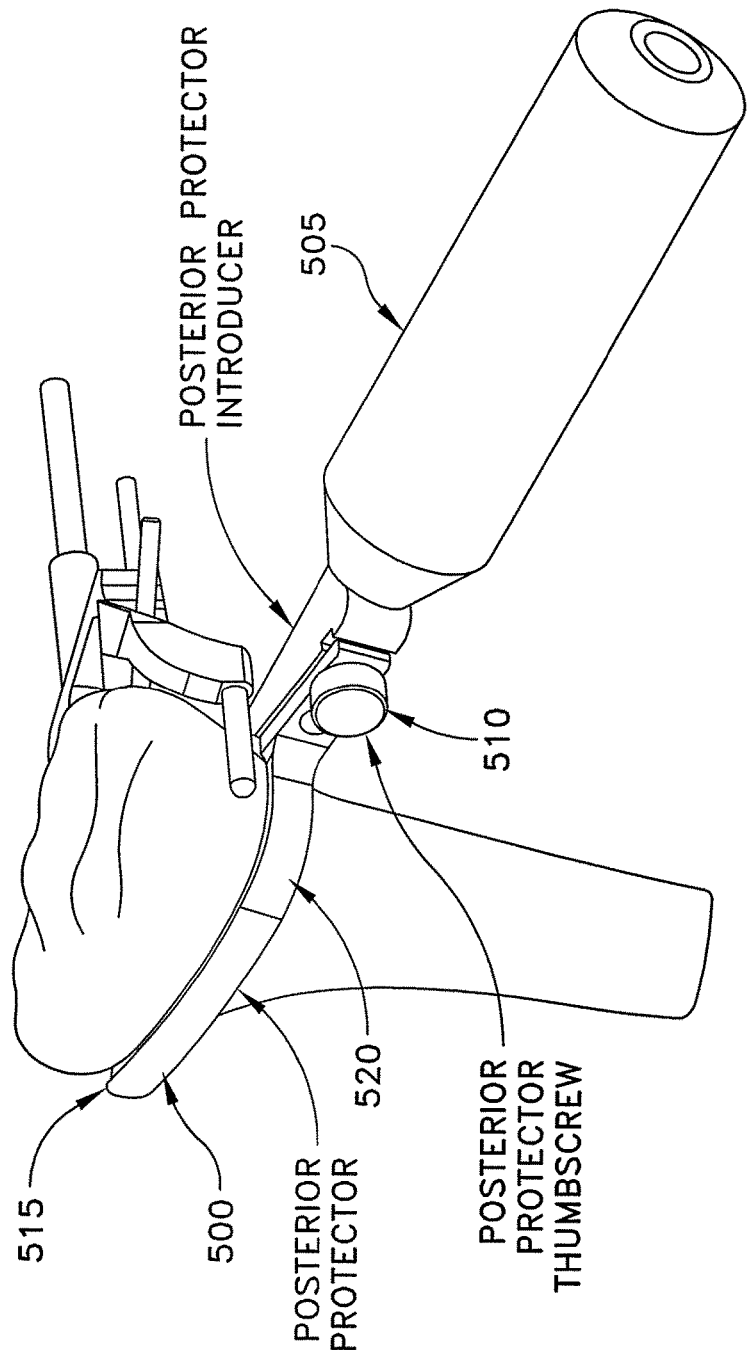

Novel Method and Apparatus for Performing the Open Wedge, High Tibial Osteotomy of the Present Invention In one preferred embodiment of the present invention, there is provided a novel osteotomy system which comprises instrumentation for use in making precise and repeatable osteotomy cuts for use in open wedge, high tibial osteotomies, preferably using an antero-medial approach. The novel osteotomy system generally comprises a positioning guide 100 (FIG. 16), a slope guide 200 (FIG. 11), an apex pin 300 (FIG. 16), a keyhole drill guide 400 (FIG. 18), a posterior protector 500 (FIG. 20), and a cutting guide 600 (FIG. 20), as will hereinafter be discussed in further detail.

Figure 22:
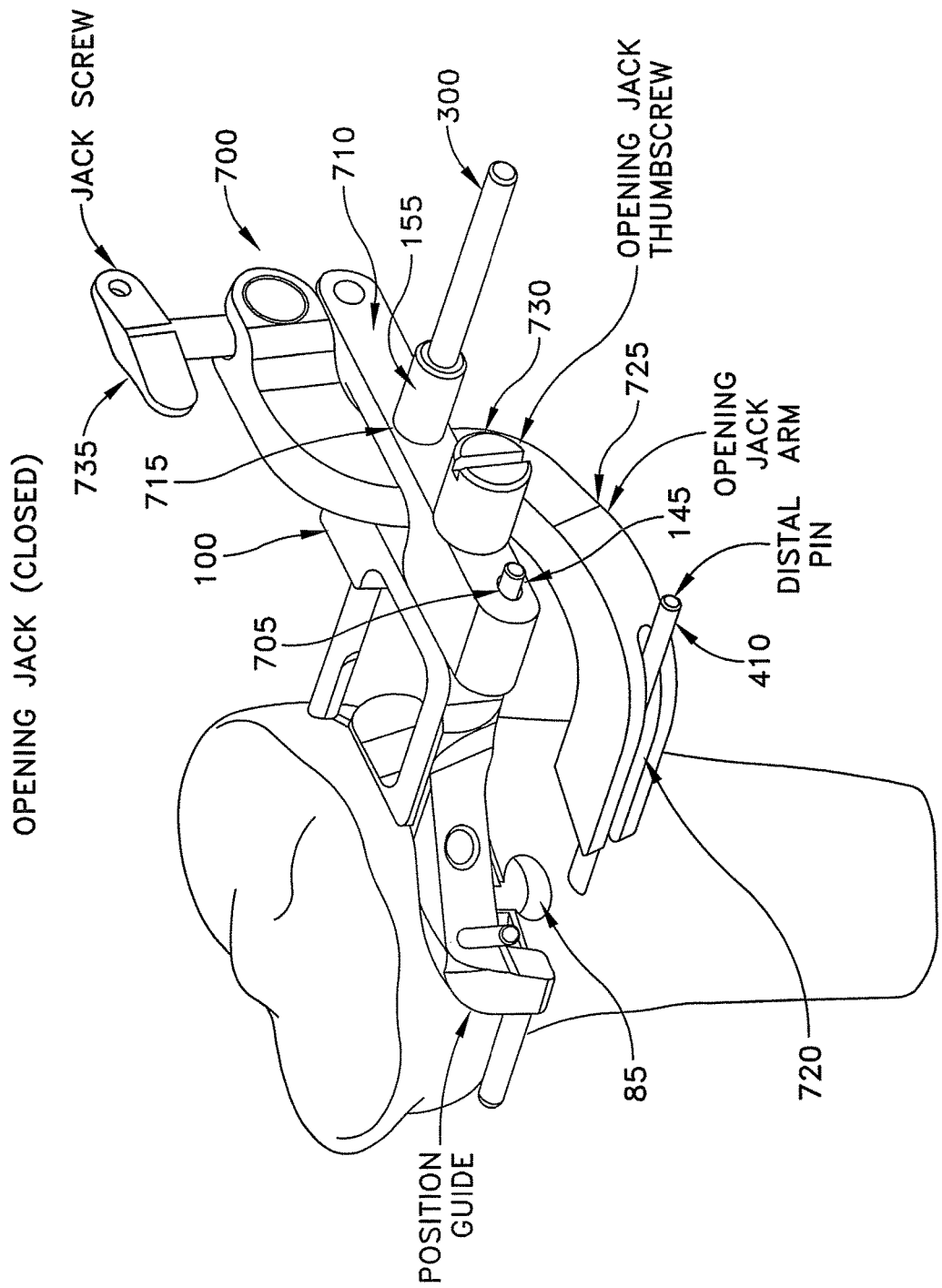

The novel osteotomy system preferably also comprises a novel opening jack 700 (FIG. 22) for opening the cut 20 in the tibia so as to form the wedge-like opening 25 in the tibia, as will also hereinafter be discussed in further detail.

And the novel osteotomy system preferably also includes a novel implant 800 (FIG. 24) for positioning in the wedge-like opening in the tibia so as to stabilize the tibia in its corrected configuration, as will also hereinafter be discussed in further detail. Furthermore, in some instances, it may be advantageous to use an implant trial base 830 (FIGS. 27 and 28) in the course of preparing the tibia to receive implant 800, and in order to confirm proper fit of implant 800 in its seat, as will also hereinafter be discussed in further detail.

Thus, with the present invention, the surgeon first determines (using methods well known in the art) the degree of correction necessary to correctly re-align the weight-bearing axis of the knee; then the surgeon uses the system to make the appropriate cut 20 into the tibia; then the surgeon opens the bone cut to the extent required so as to form the desired wedge-like opening 25 in the tibia; and then the surgeon stabilizes the tibia in its corrected configuration (e.g., with the novel implant 800) while healing occurs.

In a preferred form of the invention, the novel osteotomy system is configured so that:

(i) the axis 70 (FIG. 8) formed at the lateral limit of the osteotomy cut 20 (which forms the lateral limit of the remaining bony hinge when the osteotomy cut 20 is thereafter opened) is parallel to the A-P tibial slope;

(ii) the axis of the lateral limit of the bony hinge created by the osteotomy cut lies in a plane that is perpendicular to the frontal (i.e., coronal) plane; and (iii) when the osteotomy cut 20 is completed and the wedge is opened, the distal (i.e., lower) tibia is rotated about the bony hinge so as to substantially maintain, in anatomical alignment, the A-P slope and the frontal plane.

In a preferred form of the invention, the novel osteotomy system is also configured so that:

(iv) the osteotomy can be performed less invasively; and (v) the osteotomy can be performed with minimum incising of soft tissue such as the medial collateral ligament, the lateral collateral ligament, and the hamstrings.

In a preferred form of the invention, the novel osteotomy system is also configured so that the delicate neurological and vascular tissues at the back of the knee are fully protected during the osteotomy procedure.

In one preferred form of the present invention, the novel osteotomy system is constructed and used as follows.

1. A vertical incision is first made on the antero-medial portion of the knee, approximately 1 cm from the medial edge of the patellar tendon, with the incision beginning approximately 2.5-3 cm superior to the anterior tibial tubercle, and extending approximately 6-10 cm in length.

2. The soft tissue between the patellar tendon and the proximal surface of the tibia is then dissected in order to make a small tunnel-like opening beneath the patellar tendon, just above the patellar tendon's insertion to the proximal tibia.

3. Looking now at FIG. 10, an assembly comprising positioning guide 100 (FIGS. 10 and 16), slope guide 200 (FIGS. 10 and 11) and an introducer 105 (FIGS. 10 and 11) is advanced to the surgical site. Preferably the assembly of positioning guide 100, slope guide 200 and introducer 105 is pre-assembled prior to opening the skin. This assembly is assembled by first mounting slope guide 200 to positioning guide 100, and then mounting introducer 105 to both slope guide 200 and positioning guide 100 by using a screw 115 (FIG. 10) which passes through slope guide 200 and is received in a threaded bore 120 (FIG. 16) formed in positioning guide 100.

In one preferred form of the invention, slope guide 200 may comprise two separate elements which are secured together, e.g., a base 210 and a guide element 215 which are connected together by pins 205, with base 210 being formed out of a radio-translucent material (e.g., plastic) and guide element 215 being formed out of a radio-opaque material (e.g., stainless steel), whereby guide element 215 will be visible under fluoroscopy and base 210 will be effectively invisible under fluoroscopy, as will hereinafter be discussed.

In one preferred form of the invention, introducer 105 may comprise an arm 125 and a handle 130. Arm 125 and handle 130 may be formed as two separate elements secured together, or arm 125 and handle 130 may be formed as a singular construction.

4. Next, the foregoing assembly (of positioning guide 100, slope guide 200 and introducer 105) is maneuvered so that a tibial tubercle locating tab 135 (FIGS. 10 and 16) of positioning guide 100 is inserted between the patellar tendon (not shown) and the tibia, and so that tibial tubercle locating tab 135 is set against the superior margin of the tibial tubercle. In this way, the tibial tubercle provides a rough alignment guide for aligning positioning guide 100 with the tibia. If desired, the underside of tibial tubercle locating tab 135 may include serrations, ridges, ribs, etc. (FIG. 11E) so as to facilitate stabilization of tibial tubercle locating tab 135 (and hence the instrumentation) against the tibia.

5. Using a lateral fluoroscope view, taken from the medial side at the level of the tibial plateau, the assembly is then aligned so that the underside surface 220 (FIG. 11) of guide element 215 of slope guide 200 is aligned with the top of the medial condyle 75 of the tibia. Alternatively, if the surgeon prefers to shift the osteotomy slightly distally on the tibia, the top edge 225 of guide element 215 of slope guide 200 can be aligned with medial condyle 75, thereby offsetting the osteotomy by a fixed distance distally (e.g., 3 mm).

By forming the guide element 215 of slope guide 200 out of a radio-opaque material and by forming the base 210 of slope guide 200 out of a radio-translucent material, base 210 will be effectively invisible under fluoroscopy and guide element 215 will stand out in clear relief against the bone.

Figure 10:
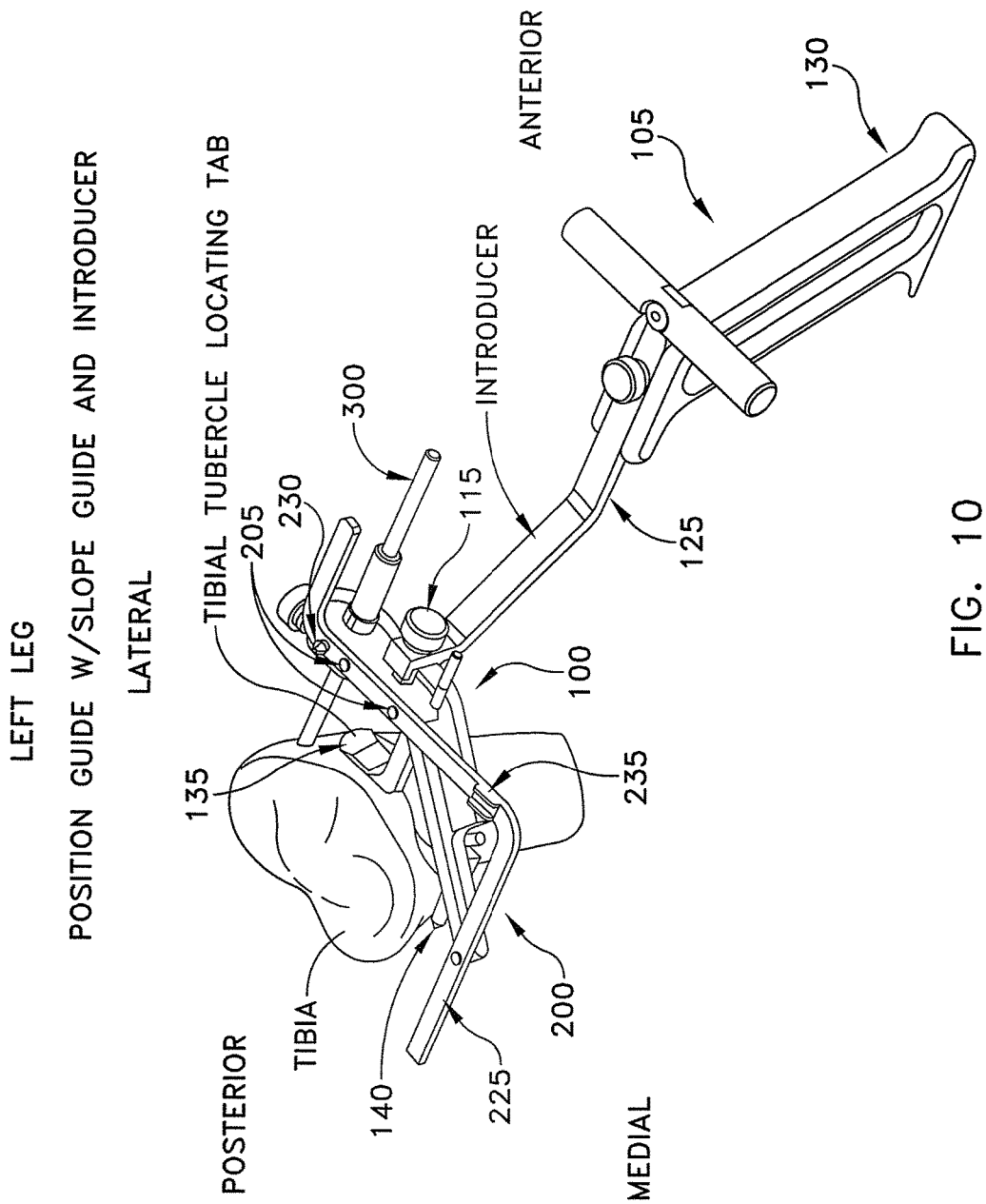
Figure 11:
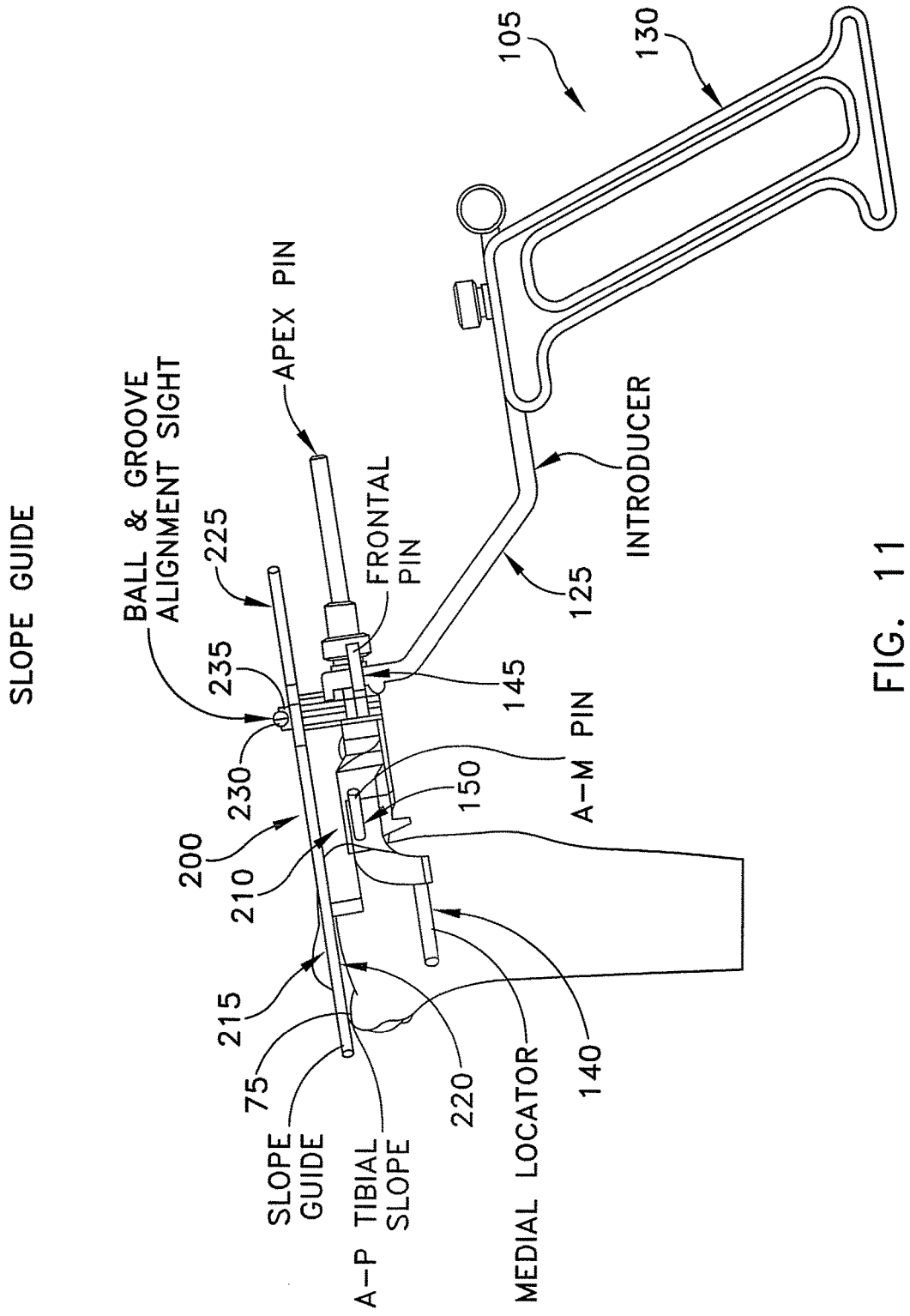
Figure 11A:
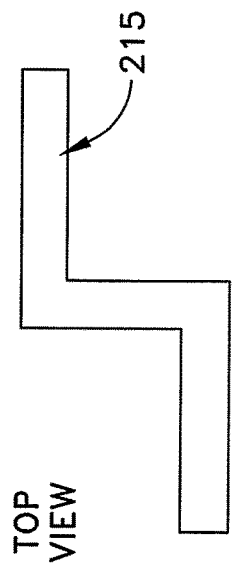
Figure 11B:
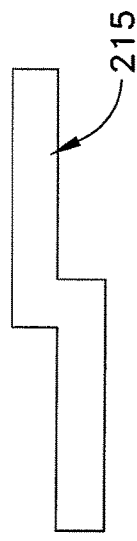
Figure 11C:
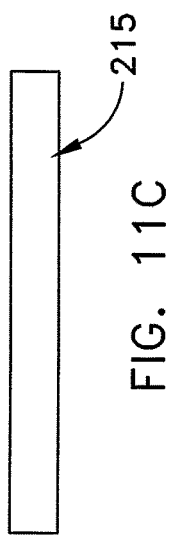

It should be noted that guide element 215 of slope guide 200 is preferably formed with a "Z shape" (FIGS. 10 and 11A) so as to provide additional functionality. More particularly, by forming guide element 215 with a "Z shape", several significant advantages are obtained. First, this construction permits guide element 215 to wrap around the perimeter of the tibia. Second, the "Z shape" of guide element 215 also operates to indicate if the slope guide is not vertically aligned with the level of the fluoroscope. More particularly, if slope guide 200 is not vertically aligned with the level of the fluoroscope, the "Z shape" of guide element 215 will appear as a jagged or zig-zag shape on the fluoroscope (FIG. 11B). However, if guide element 215 is vertically aligned with the level of the fluoroscope, then the guide element will appear as a straight line on the fluoroscope (FIGS. 11 and 11C). This vertical alignment is important, since it enables alignment of slope guide 200 (and hence positioning guide 100) with the medial condyle, i.e., with the A-P slope plane.

Figure 11D:
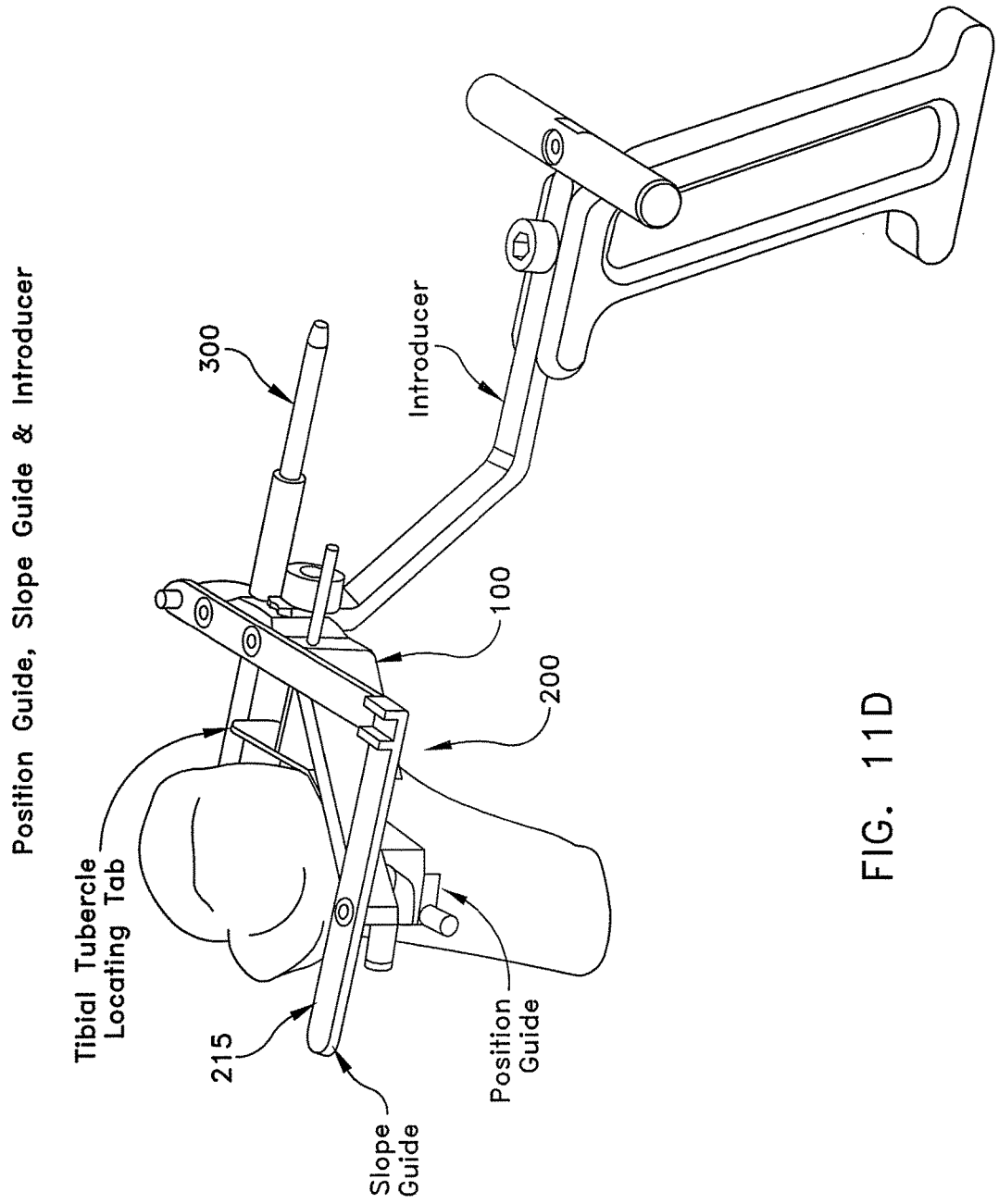
Figure 11E:
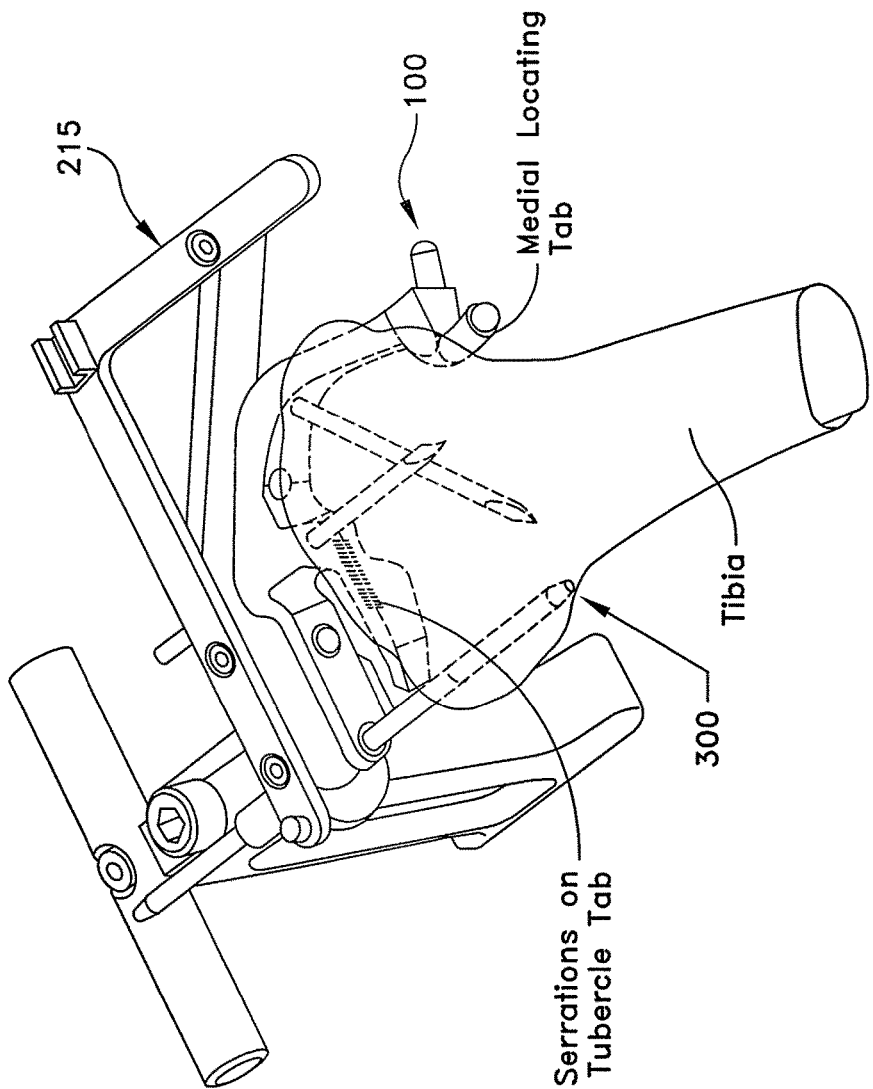
Figure 11F:
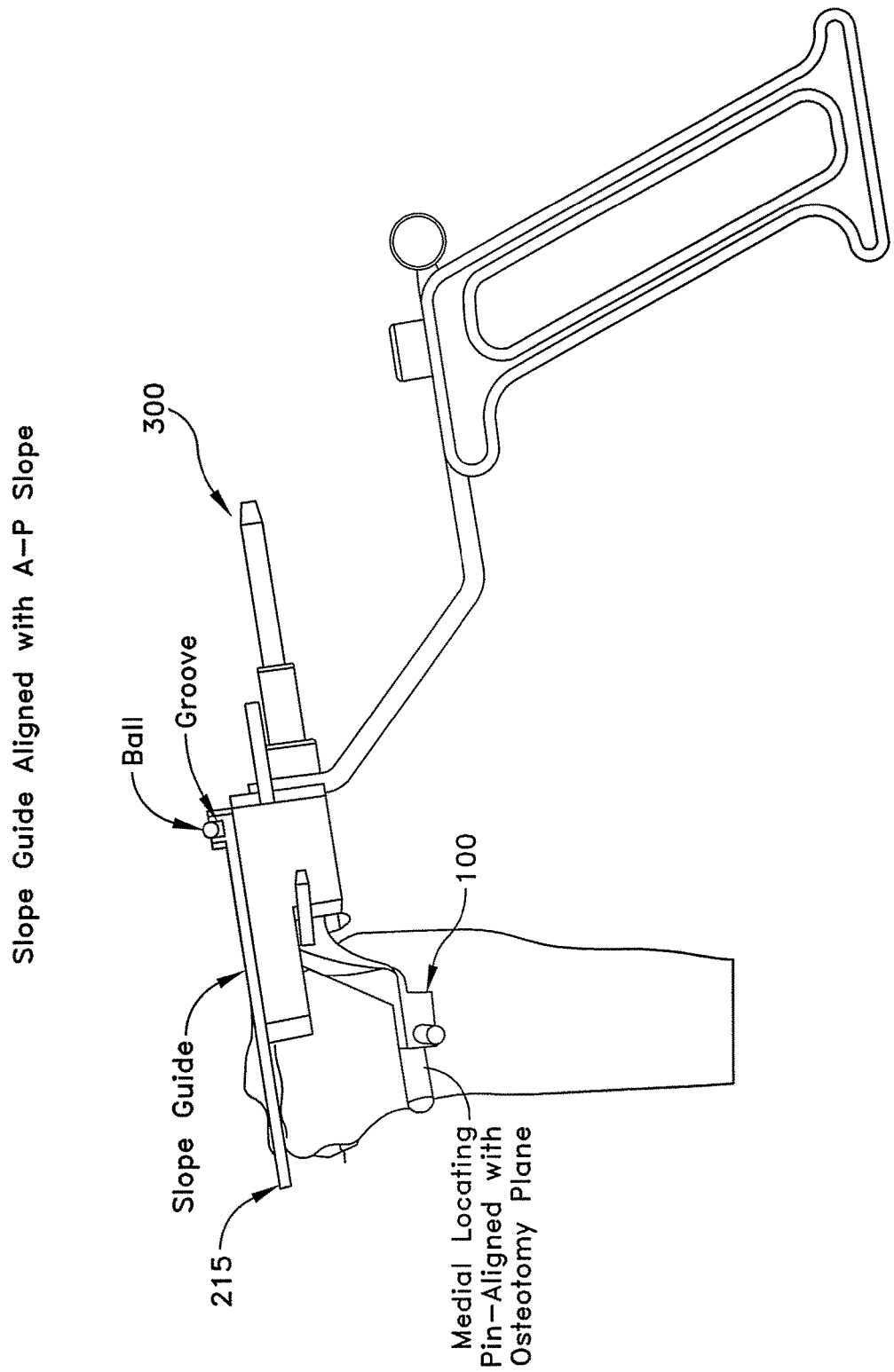

If desired, and looking now at FIGS. 11D, 11E and 11F, it is also possible to provide guide element 215 of slope guide 200 with an "L shape" configuration, rather than the "Z shape" configuration discussed above. Again, this construction provides several benefits. First, the "L shape" configuration permits guide element 215 to wrap around the perimeter of the tibia. Second, the "L shape" of guide element 215 also operates to indicate if the slope guide is not vertically aligned with the level of the fluoroscope. More particularly, if slope guide 200 is not vertically aligned with the level of the fluoroscope, the "L shape" of guide element 215 will appear as an "L shape" on the fluoroscope. However, if guide element 215 is vertically aligned with the level of the fluoroscope, then the guide element will appear as a straight line on the fluoroscope. Again, this vertical alignment is important; since it enables alignment of slope guide 200 (and hence positioning guide 100) with the medial condyle, i.e., with the A-P slope plane.

7. The assembly is then maneuvered so that the medial locating pin 140 (FIGS. 10, 11 and 16), preferably formed as a pin although it could also be formed as a tab, fin, etc., is located against the medial aspect 80 (FIG. 16) of the tibia. As further adjustments in position are made, medial locating pin 140 is held in contact with the medial aspect of the tibia, thereby ensuring proper alignment of the instrumentation. Medial locating pin 140 references the medial aspect of the tibia, thus setting the distance from the medial aspect of the tibia to the apex pin 300 (FIG. 10), and hence the distance from the medial aspect of the tibia to the axis 70 which demarcates the far limit of the osteotomy cut, as will hereinafter be discussed. Where a wedge-shaped osteotomy implant 27 is to be deployed in the wedge-like opening 25 (e.g., such as is shown in the system of FIGS. 10-30), this reference distance is used in conjunction with the sizing of the osteotomy implant 27 (FIG. 3) so as to ensure a proper tibial reconstruction, e.g., the distance from the medial aspect of the tibia to the center of apex pin 300 may correspond to the distance from the medial aspect of the wedge-shaped osteotomy implant 27 to the vertex of the wedge angle of the implant.

In another form of the invention, the reference distance may be the distance from the medial aspect of the tibia to a neutral axis of rotation in the bony hinge, which could be estimated by calculation. In this case, the distance from the medial aspect of the tibia to the neutral axis of the bony hinge may correspond to the distance from the medial aspect of the implant to the vertex of the wedge angle of the implant.

8. The assembly is then rotated around the primary tibial anatomical axis, by sliding introducer handle 130 in a side-to-side motion, such that the instrumentation is aligned perpendicular to the frontal (coronal) plane, i.e., so that introducer 105 and apex pin 300 (see below) extend parallel to the sagittal plane of the patient. To this end, slope guide 200 is provided with a ball 230 and a groove 235 (FIGS. 10 and 11). With the fluoroscope arranged so that it is set in the lateral mode, with the image being taken from the medial side at the level of the tibial plateau (see FIG. 11), the assembly is maneuvered until ball 230 is centered in groove 235 (FIG. 11). When this occurs, the system is aligned with the sagittal plane (i.e., positioning guide 100 is disposed so that apex pin 300 will extend perpendicular to the frontal plane, as will hereinafter be discussed).

9. Thus, when slope guide 200 is aligned with the medial condyle 75, and when ball 230 is aligned with groove 235, the system is aligned with (i) the A-P slope, and (ii) the sagittal plane. In other words, when slope guide 200 is aligned with medial condyle 75, and when ball 230 is aligned with groove 235, the instrumentation is positioned so that apex pin 300 (see below) is aligned with both the A-P slope and the sagittal plane, as will hereinafter be discussed.

10. With all of the previous adjustments established, the positions of (i) tibial tubercle locating tab 135, (ii) slope guide 200, (iii) medial locating pin 140, and (iv) ball and groove sights 230, 235, are verified. With all positions confirmed, the frontal pin 145 (FIG. 16) and the antero-medial (A-M) pin 150 (FIG. 16) are inserted through positioning guide 100 and into the tibia. This secures positioning guide 100 to the tibia with the desired alignment.

11. Next, apex pin 300 is inserted through positioning guide 100 and into the tibia. An apex aimer 155 (FIGS. 14 and 16) serves to guide apex pin 300 into the tibia with the proper orientation, i.e., so that apex pin 300 is positioned along the axis 70 (FIG. 8) which is located at the lateral limit of the intended osteotomy cut, with apex pin 300 extending parallel to the A-P slope and perpendicular to the coronal plane, and with apex pin 300 being coplanar with the intended cutting plane 65. As a result, apex pin 300 can serve as the lateral stop for the osteotomy saw, whereby to clearly define the perimeter of the bony hinge, as will hereinafter be discussed. Apex pin 300 may be tapped or drilled into virgin bone, or it may be received in a pre-drilled hole (e.g., formed using apex aimer 155 and a standard surgical drill). A thumbscrew 160 (FIG. 16) may be used to secure apex pin 300 to positioning guide 100.

Figure 11G:
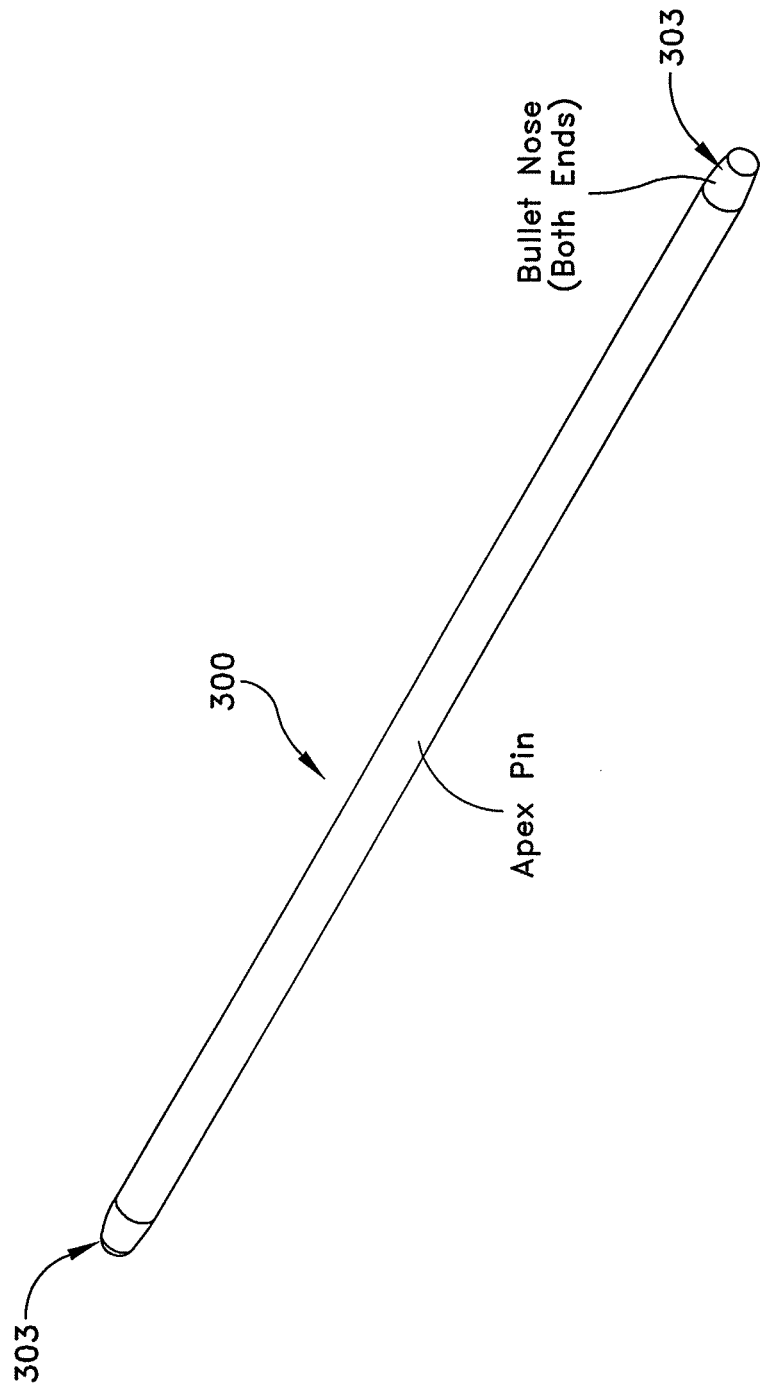
Figure 12:
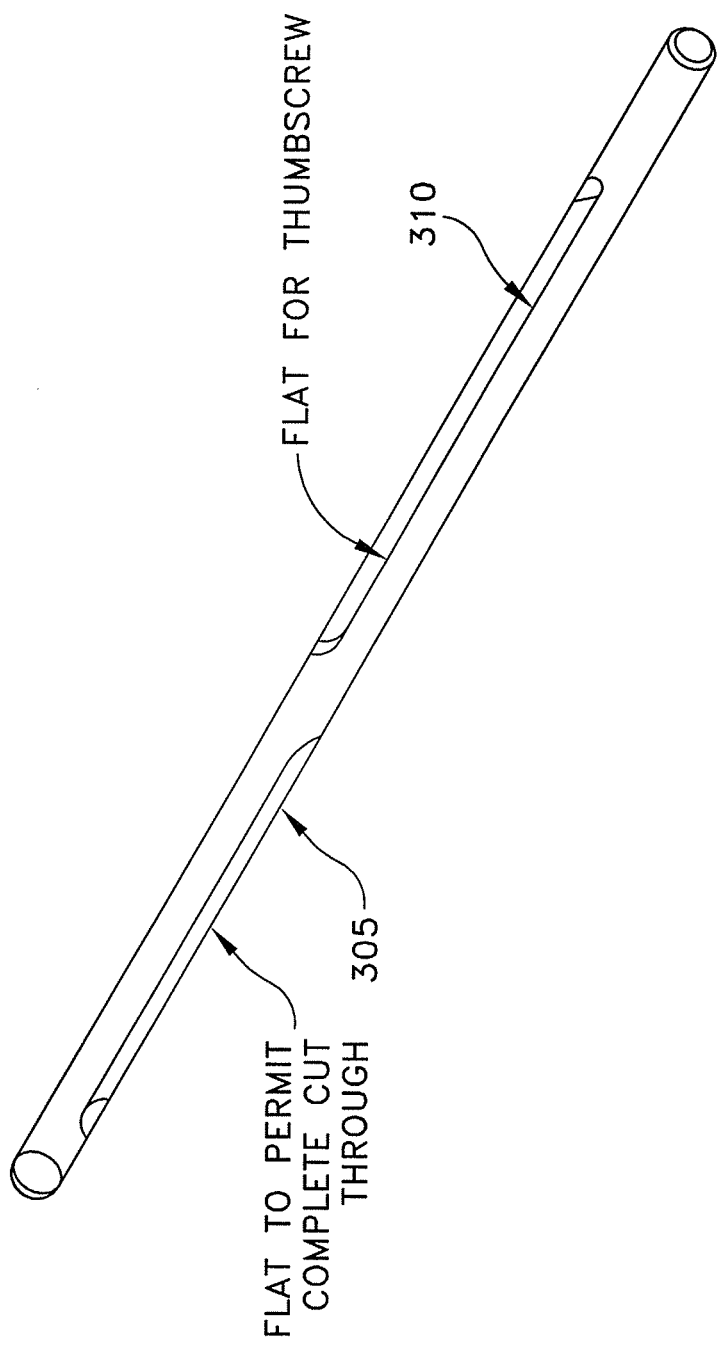
Figure 13:
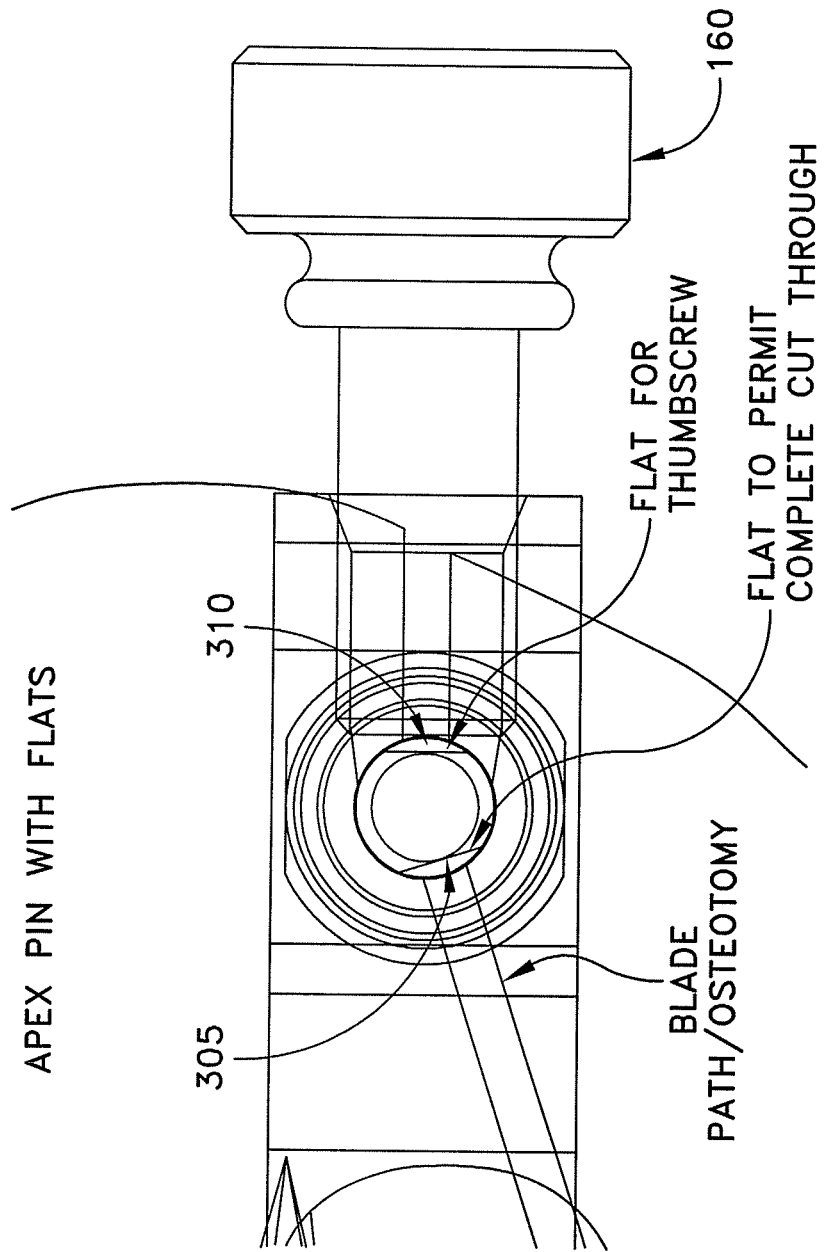
Figure 14:
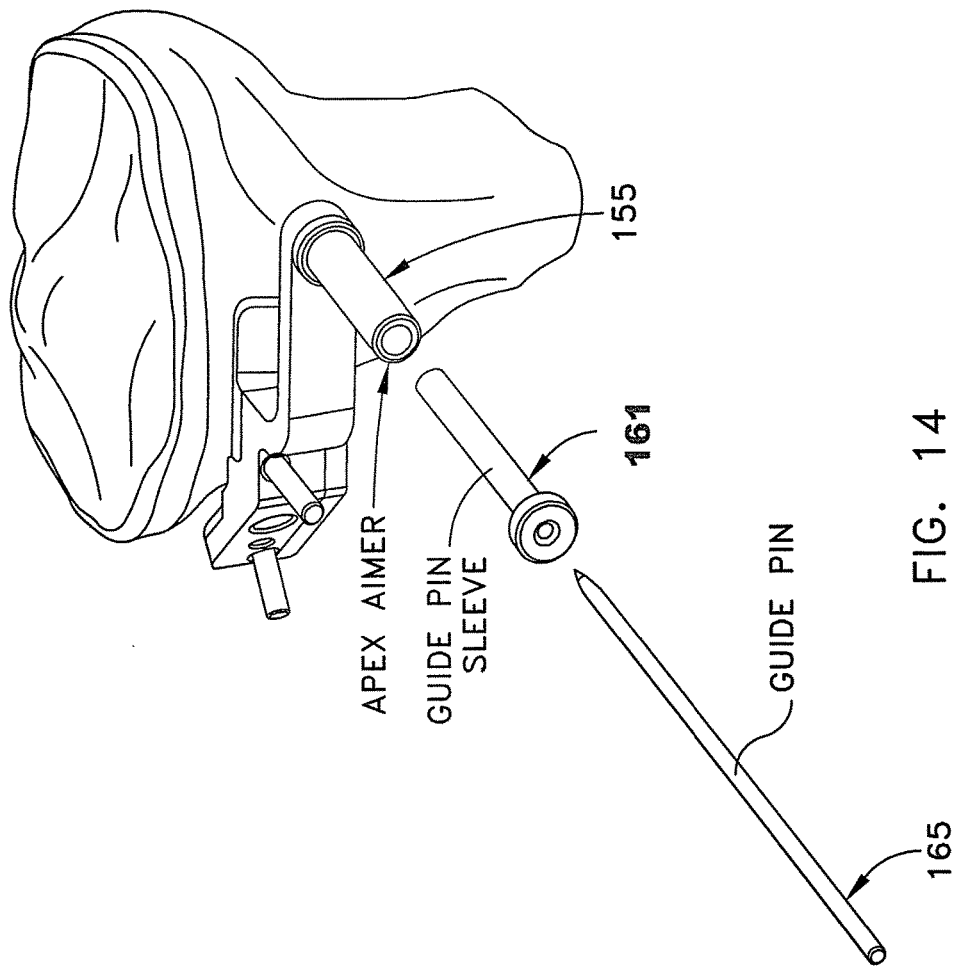

Apex pin 300 may be generally cylindrical in shape and, if desired, apex pin 300 may be provided with a rounded, or "bullet-shaped", nose 303 (FIG. 11G), or other tapered end configuration, so as to facilitate deployment into the tibia.

Furthermore, if desired, apex pin 300 may have a flat 305 (FIGS. 12 and 13) formed thereon to promote a complete cut-through of the osteotomy. Where apex pin 300 is provided with a distinct flat 305, it is preferably provided with a counterpart flat 310 (FIGS. 12 and 13), such that when apex pin 300 is positioned within the tibia and thumbscrew 160 is tightened against flat 310, the aforementioned flat 305 will be aligned with the osteotomy cut, whereby to ensure that the osteotomy blade cuts completely through the bone to reach the apex pin. See FIG. 13.

In another version of this construction (not shown), the flats 305, 310 may be diametrically opposed to one another, with thumbscrew 160 also being aligned with the osteotomy cut, whereby to make insertion of apex pin 300 less prone to error.

And in a preferred embodiment of the present invention, apex pin 300 may be necked down to a smaller diameter in the area of the osteotomy. As a result of this construction, a slight relief area exists to accommodate the saw blade so as to help promote a complete cut-through, but does not require any specific orientation of the apex pin with respect to the osteotomy plane, as is the case where the apex pin is formed with distinct flats.

And in another version of the present invention, apex aimer 155 may be used with a guide sleeve 161 (FIG. 14) and a small-diameter guide pin 165 in order to first check the position of the small-diameter guide pin 165 relative to the desired axis for the apex pin, before thereafter deploying the larger-diameter apex pin 300. In this respect, it will be appreciated that re-positioning a misdirected small-diameter guide pin 165 is easier and less traumatic to the host bone than re-positioning a misdirected larger-diameter apex pin 300.

Figure 15:
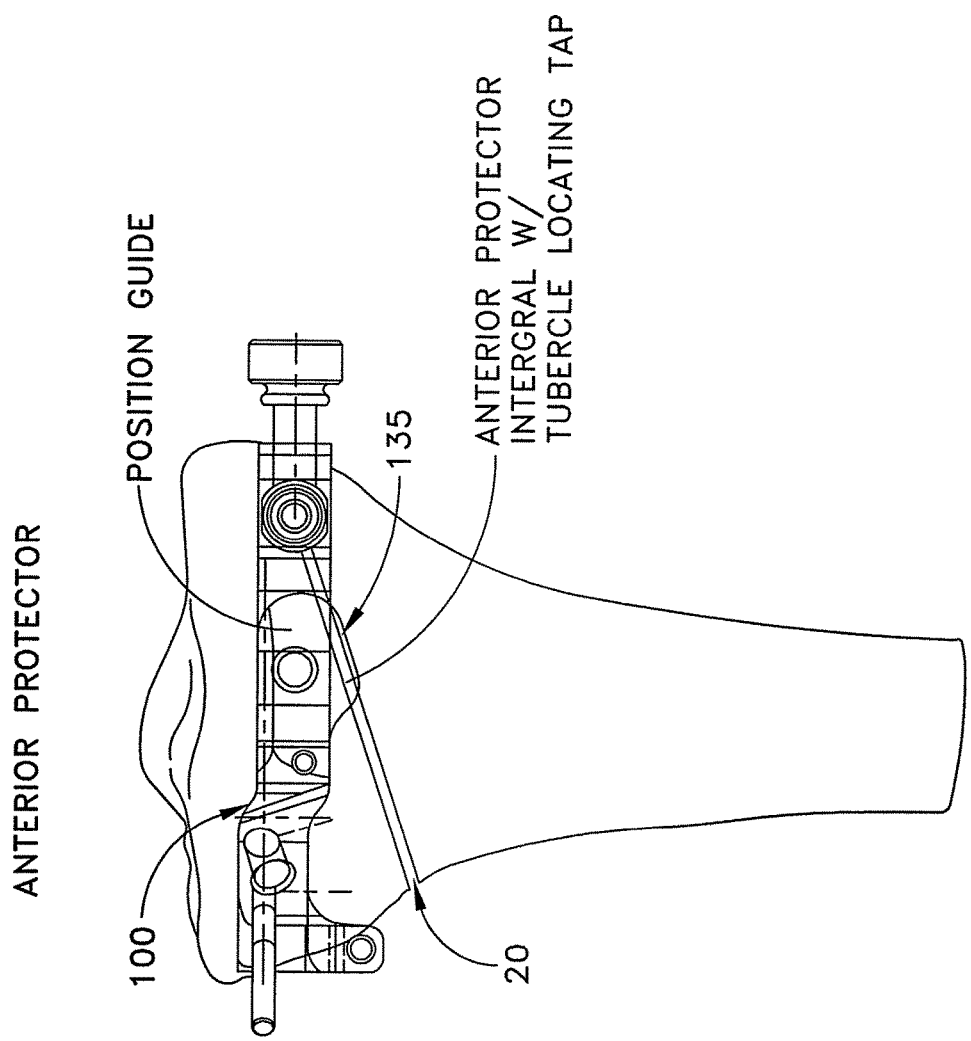

As seen in FIG. 15, tibial tubercle locating tab 135 is preferably sized so that it also functions as an anterior protector, by providing a protective shield between the oscillating saw blade (to be used later in the procedure to form the osteotomy cut 20) and the anterior soft tissue structures, e.g., the patellar tendon. In this respect it will be recalled that the tibial tubercle locating tab 135 is intended to be positioned between the face of tibia 10 and the backside of the patellar tendon. Thus, tibial tubercle locating tab 135 also functions as a patellar tendon protector.

12. By virtue of the foregoing, it will be seen that apex pin 300 is positioned in the patient's tibia so that the apex pin extends (i) parallel to the A-P slope of the tibia, and (ii) parallel to the sagittal plane of the patient. As a result, when the osteotomy cut 20 is subsequently formed in the bone (see below) by cutting along the osteotomy cut plane 65 (FIG. 8) until the apex pin is engaged by the bone saw, so that the perimeter of the bony hinge is defined by the location of the apex pin, the bony hinge will extend (i) parallel to the A-P slope of the tibia, and (ii) parallel to the sagittal plane of the patient. By ensuring that apex pin 300 is set in the aforementioned fashion, and hence ensuring that the bony hinge is so created, the final configuration of the tibia can be properly regulated when the bone cut is thereafter opened so as to form the open wedge osteotomy.

13. Once apex pin 300 has been properly positioned in the bone, slope guide 200 and introducer 105 are removed (FIG. 16), leaving positioning guide 100 properly aligned on, and secured to, the tibia, with apex pin 300 extending parallel to the A-P slope and parallel to the sagittal plane of the patient.

As will be discussed in further detail below, the system of FIGS. 10-30 utilizes a wedge-shaped implant to maintain the open wedge osteotomy. In this respect, the size of positioning guide 100 and the associated instrumentation are preferably used to prepare the osteotomy to fit a particular implant sizing of small, medium or large. More particularly, the medial locating pin 140, the size of positioning guide 100, and apex pin 300 all preferably combine to implement an implant sizing scheme of small, medium or large. As seen in FIG. 17, medial locating pin 140, positioning guide 100 and apex pin 300 combine to provide a known, fixed distance from the medial aspect of the tibia to the apex pin. The size of the planned osteotomy is then set, allowing a specifically-sized implant (e.g., small, medium or large) to nominally fit between the medial aspect of the tibia and the apex pin.

In the embodiment shown in FIG. 17, there is a known lateral offset between medial locating pin 140 and the entry point of the osteotomy. The implant size is reduced slightly to factor in this offset distance so as to yield a proper fit.

Figure 17A:
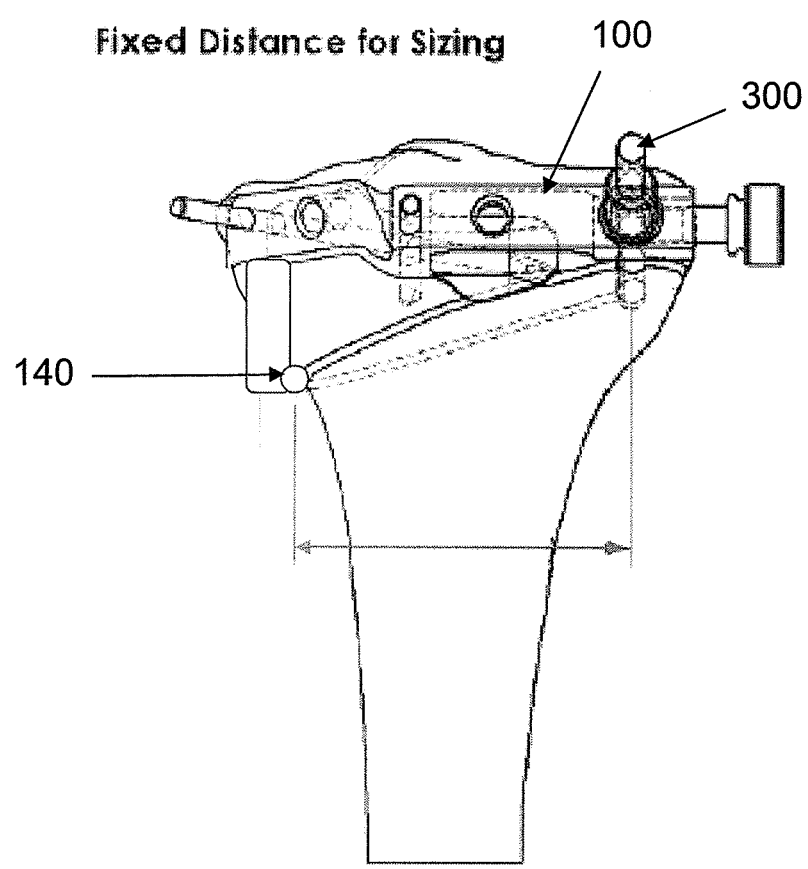

In a more preferred construction, and looking now at FIG. 17A, medial locating pin 140 is substantially aligned with the entry point of the planned osteotomy.

14. Looking next at FIG. 18, keyhole drill guide 400 is then attached to positioning guide 100 by passing keyhole drill guide 400 over frontal pin 145 and apex aimer 155. Keyhole drill guide 400 is then secured in this position with thumbscrew 405. At this point, a distal pin 410 is inserted through keyhole drill guide 400 and into the tibia. Distal pin 410 further secures the instrumentation to the tibia. Next, a surface locator pin 415 is inserted through keyhole drill guide 400. Surface locator pin 415 slides through keyhole drill guide 400 until the distal tip of surface locator pin 415 contacts the surface of the tibia. For the purposes of the present invention, this surface may be referred to as the "antero-medial surface" or the "A-M surface", which is the anatomical surface of the tibia corresponding to the antero-medial approach of the osteotomy. When surface locator pin 415 contacts the A-M surface, the surface locator pin can act as an indicator as to the location of the A-M surface. This information can then be used to set the depth of the keyholes which are to be formed in the tibia (see below) for an improved implant fit.

Figure 29:
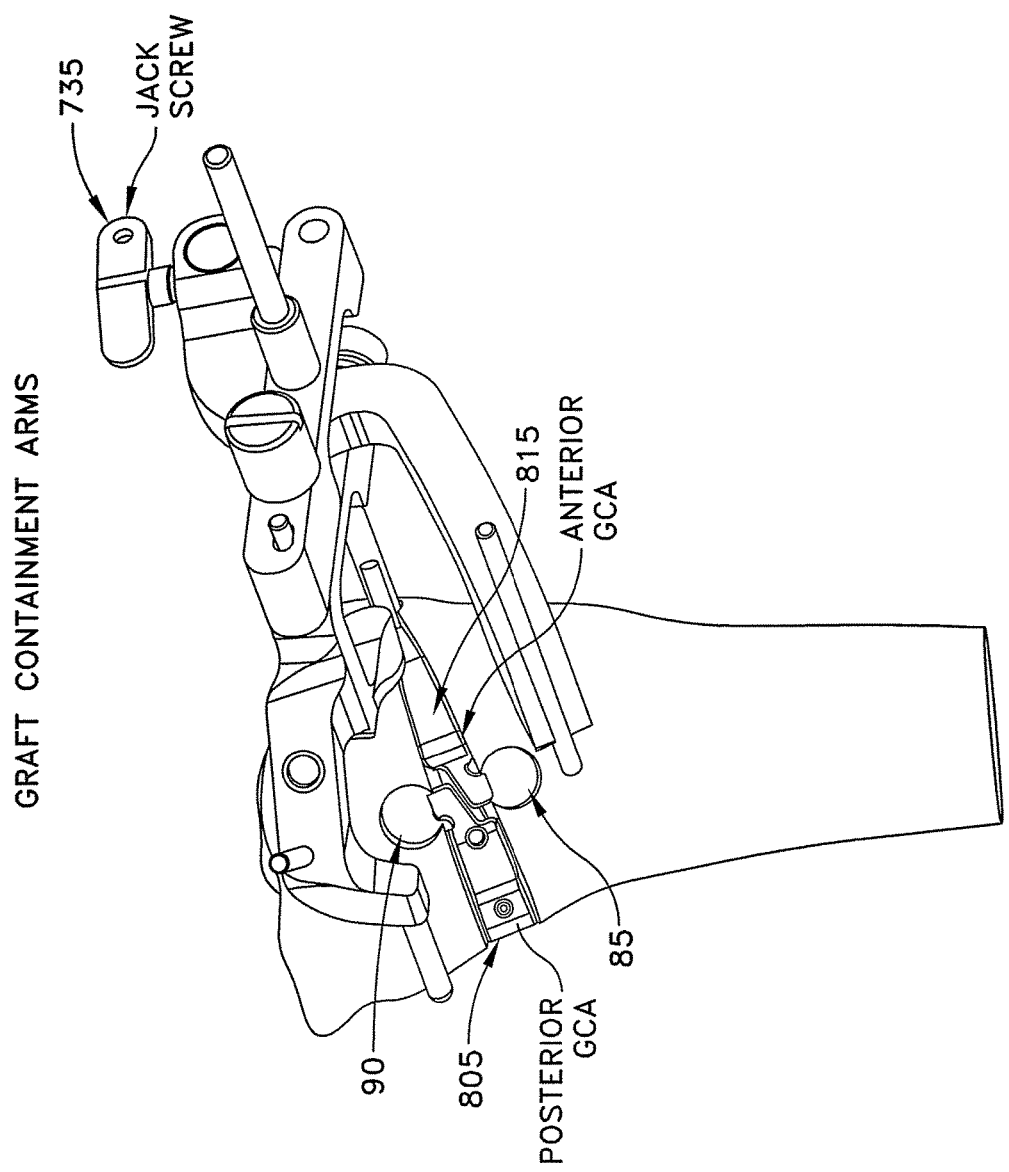
Figure 30:
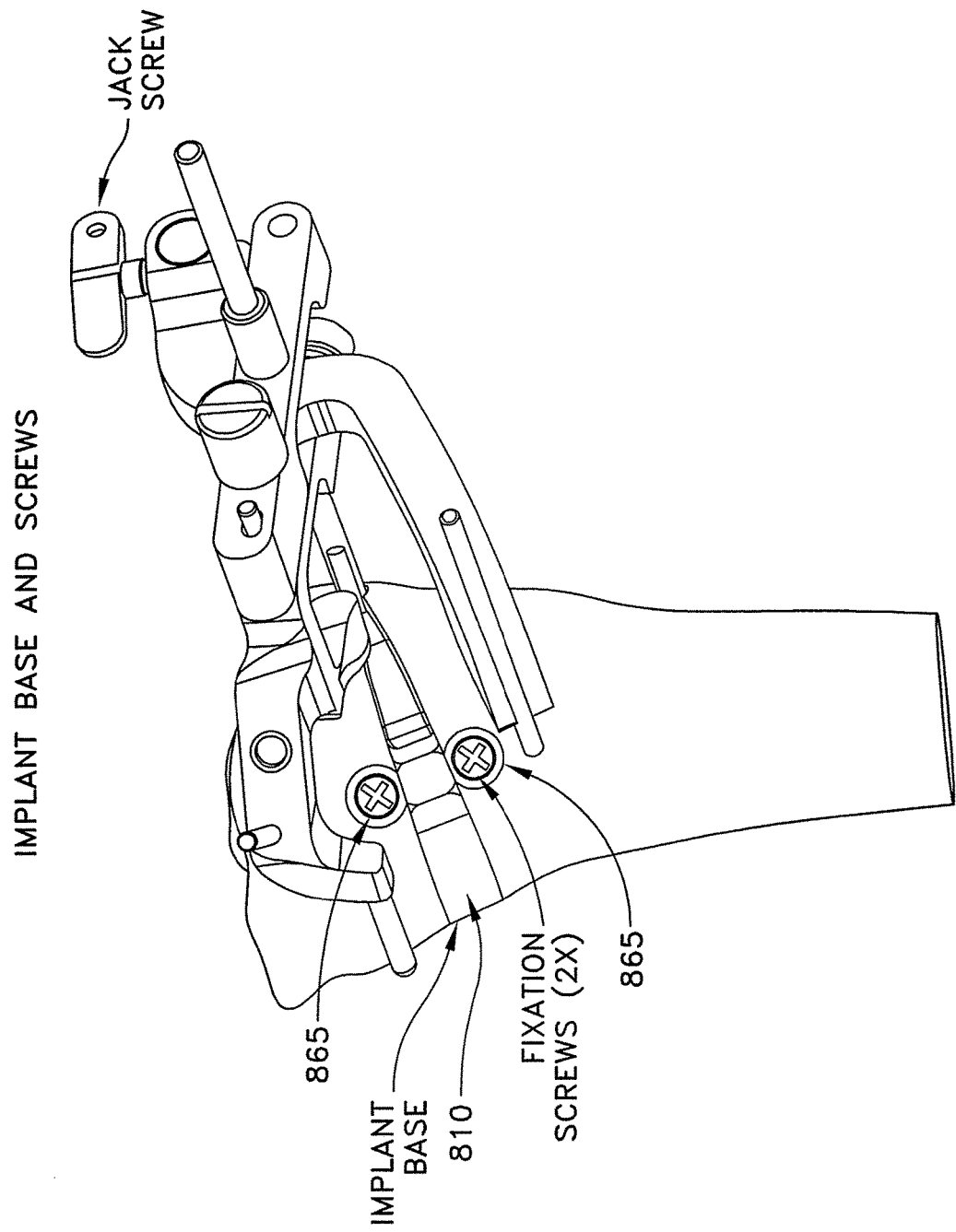

Next, an end mill 420 is inserted into the distal hole 425 (i.e., the bottom hole 425) of keyhole drill guide 400 and drilled until a stop flange 430 on end mill 420 contacts the proximal end of surface locator pin 415, whereby to form the distal keyhole 85 (FIG. 21) in the tibia. The drilling procedure is then repeated for the proximal hole 435 (i.e., the top hole 435), whereby to form the proximal keyhole 90 (FIG. 21) in the tibia. Thus, keyholes 85 and 90 are formed so that one keyhole (i.e., proximal keyhole 90) sits above the other keyhole (i.e., distal keyhole 85), in a so-called "over-under" configuration. While it is possible to drill the proximal keyhole before the distal keyhole, it is generally preferable to drill the distal keyhole first. This is because drilling the distal keyhole before the proximal keyhole reduces the possibility that the sloping nature of the bone will cause a later-drilled keyhole to slip into an earlier-drilled keyhole. It should be appreciated that keyhole drill guide 400 is configured so that distal hole 425 and proximal hole 435 will overlap the osteotomy cutting plane 65 to some extent (FIG. 21), so that when osteotomy cut 20 is thereafter formed and the tibia subsequently opened so as to create the wedge-like opening 25, distal keyhole 85 and proximal keyhole 90 will overlap, and communicate with, the wedge-like opening 25 (FIG. 29).

15. Once the two implant keyholes have been drilled into the tibia, end mill 420 is removed, thumbscrew 405 is loosened, and then keyhole drill guide 400 is removed.

16. Next, and looking now at FIG. 19, posterior protector 500 is attached to an introducer 505 with a thumbscrew 510. Posterior protector 500 preferably comprises a far tip 515 and a curved portion 520. Far tip 515 is preferably formed out of a flexible material so as to facilitate passage of the posterior protector along the surface of the posterior cortex and beneath overlying soft tissue. Curved portion 520 comprises a relatively stiff material which provides support for far tip 515. Far tip 515 of posterior protector 500 is inserted into the incision and worked along the posterior cortex of the tibia until far tip 515 of posterior protector 500 substantially crosses the axis of, and in some cases actually engages, apex pin 300 (FIG. 21). Once posterior protector 500 has been properly positioned, the thumbscrew 510 is unscrewed, and introducer handle 505 is removed, leaving posterior protector 500 extending along the posterior cortex of the tibia, interposed between the tibia and the delicate neurological and vascular structures located at the back of the knee.

17. Looking next at FIG. 20, cutting guide 600 is then attached to positioning guide 100 and secured in place using cutting guide thumbscrew 605. Cutting guide 600 comprises alignment rods 610 (FIG. 21) that extend from the cutting guide into the pre-drilled keyholes 85, 90 (FIG. 21) to assist with cutting alignment. More particularly, alignment rods 610 ensure proper alignment between cutting guide 600, its cutting slot 615 (FIGS. 20 and 21) and the pre-drilled keyholes 85, 90 previously formed in the tibia with end mill 420 and, ultimately, ensure the desired fit between the implant and the tibia.

Figure 20:
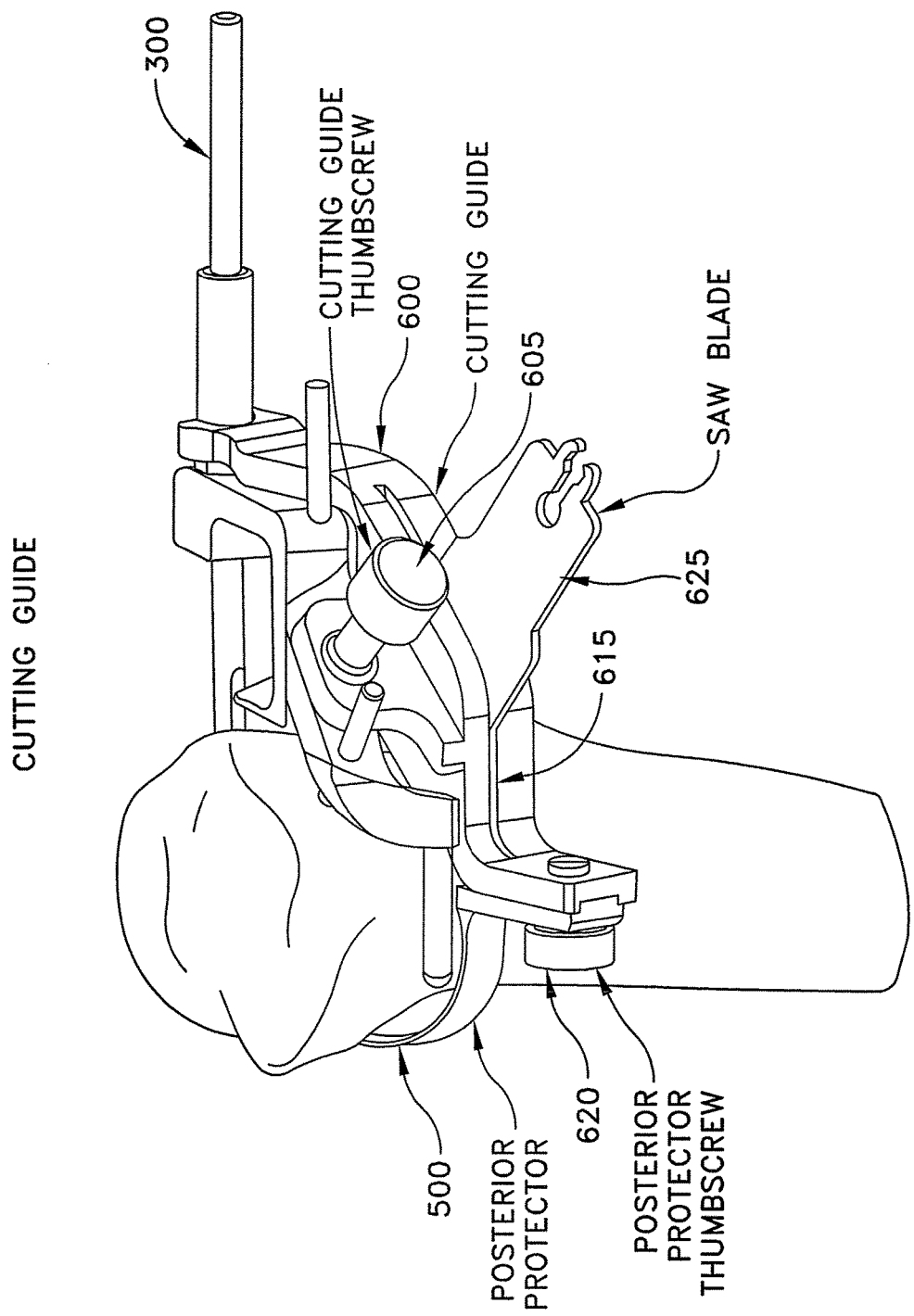

Then, posterior protector 500 is attached to cutting guide 600 using thumbscrew 620 (FIG. 20).

At this point, the instrumentation is ready to form the osteotomy cut, with cutting slot 615 of cutting guide 600 properly aligned with the osteotomy cut plane, apex pin 300 properly positioned at the far (lateral) limit of the osteotomy cut, tibial tubercle locating tab 135 forming a protective shield for the patellar tendon, and with posterior protector 500 forming a protective shield for the vascular and neurological structures at the back of the knee. In this respect it should be appreciated that cutting guide 600 is sized and shaped, and cutting slot 615 is positioned, so that, in addition to being aligned with the apex pin 300, the entry point of the cutting plane into the tibia is located at an appropriate location on the tibia's medial neck 66.

18. Next, a saw blade 625 (attached to an oscillating saw, not shown) is inserted into cutting slot 615 of cutting guide 600. The osteotomy cut is then made by plunging the oscillating saw blade through cutting slot 615 and into the bone (FIG. 20). The saw blade is used to cut completely through the medial and posterior cortices. The saw is operated until saw blade 625 contacts posterior protector 500 and apex pin 300. As the saw blade cuts through the tibia, it is constrained by cutting slot 615, apex pin 300 and posterior protector 500, so that the saw blade may only cut bone along the osteotomy plane, up to (but not beyond) the desired location of the bony hinge, and does not cut soft tissue. During cutting, tibial tubercle locating tab 135 also ensures that the saw blade will not inadvertently cut the patellar tendon. Thus, cutting slot 615, apex pin 300, posterior protector 500 and tibial tubercle locating tab 135 effectively define a "safe cutting zone" for saw blade 625.

After saw blade 625 forms the desired osteotomy cut 20 along the cutting plane, the saw blade is removed, and a hand osteotome (not shown) of the sort well know in the art is inserted through cutting slot 615 and into the osteotomy cut 20, and then the cut is completed through the posterior cortical bone near apex pin 300 and posterior protector 500. Then the hand osteotome is removed.

At this point the osteotomy cut 20 has been completed, with the osteotomy cut terminating on the lateral side at apex pin 300, so that the bony hinge is properly positioned at the desired location, i.e., parallel to the A-P slope and perpendicular to the coronal plane.

Next, thumbscrew 620 is loosened and posterior protector 500 removed. Then thumbscrew 605 is loosened and cutting guide 600 is removed. See FIG. 21.

At this point, the desired osteotomy cut 20 has been formed in the tibia, with keyholes 85 and 90 formed below and above, respectively, the osteotomy cut.

In order to complete the procedure, the bone must now be opened so as to reconfigure the tibia to the desired geometry, and then the tibia stabilized with the desired configuration, e.g., by inserting a wedge-shaped implant 27 into wedge-like opening 25.

19. Looking next at FIG. 22, opening jack 700 is assembled onto the instrumentation by receiving frontal pin 145 in a hole 705 formed in jack arm 710, by receiving apex aimer 155 in another hole 715 formed in jack arm 710 and jack arm 725, and by receiving distal pin 410 in a slot 720 formed in jack arm 725. Opening jack 700 is secured to positioning guide 100 with a thumbscrew 730.

Figure 23:
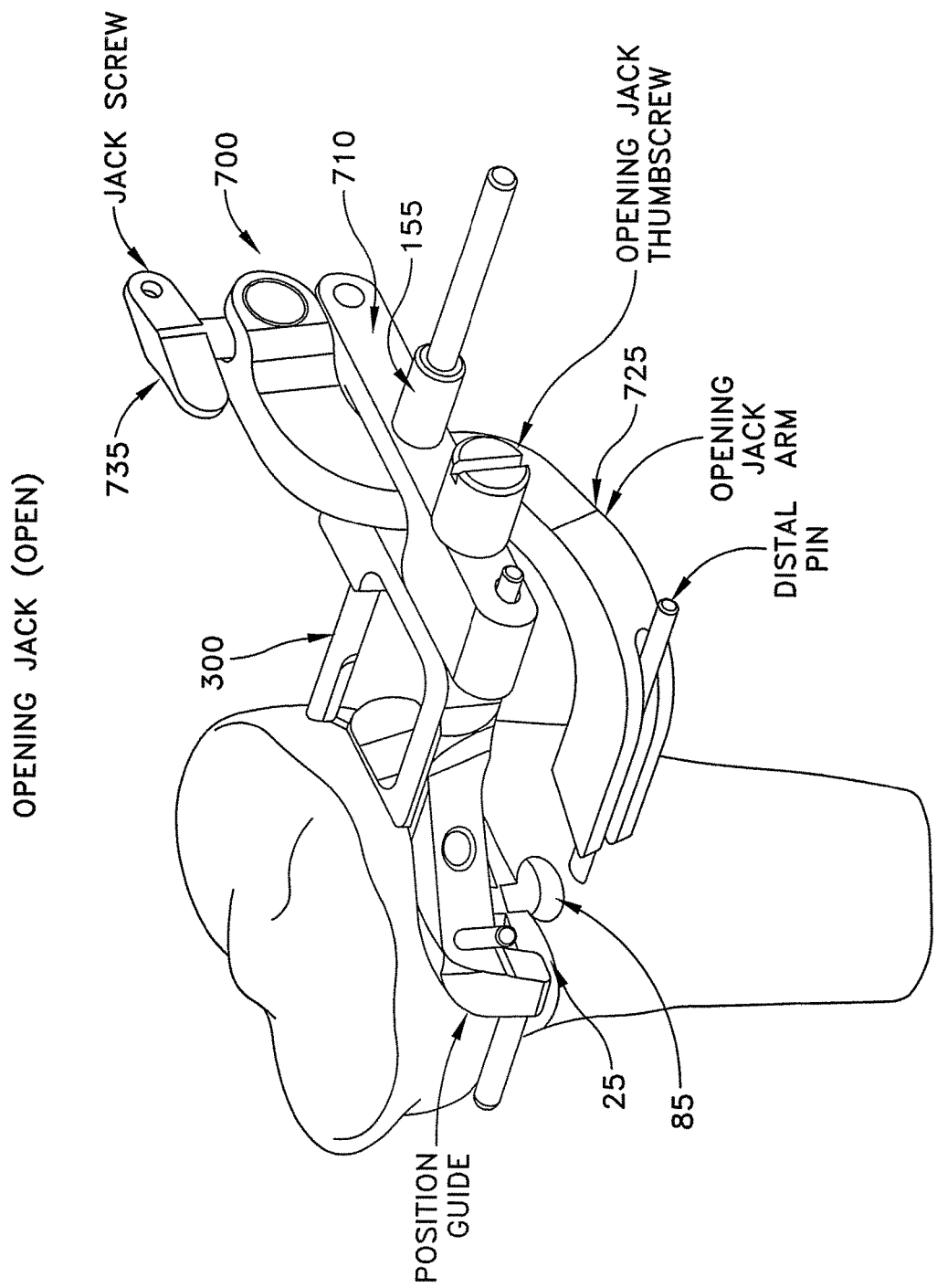
Figure 23A:
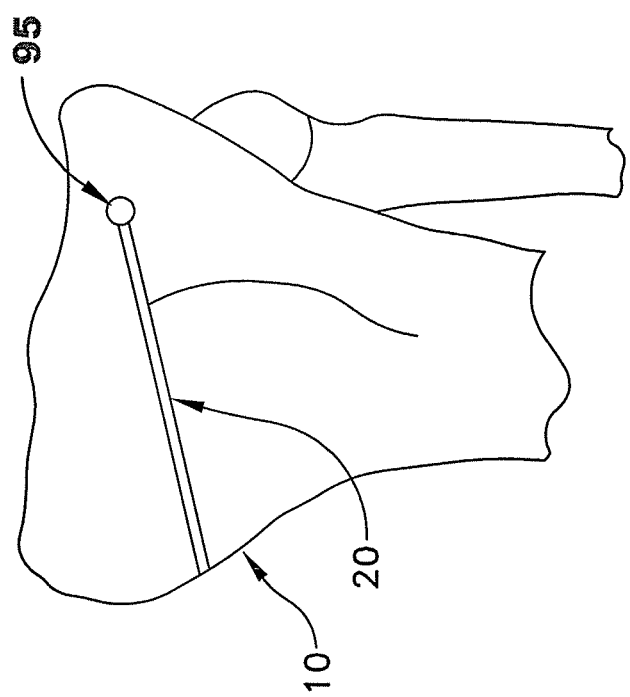

Once opening jack 700 is in place, the jack is opened by rotating jack screw 735. This causes jack arm 725 to pivot about apex aimer 155 so as to open the jack and thereby open the desired wedge-like opening 25 in the tibia. See FIG. 23. Preferably the patient's lower leg is manipulated as jack screw 735 is turned so as to assist in opening of the bone about the bony hinge. As the wedge-like opening 25 is created in the bone, the tibia will be reoriented in a highly controlled manner, due to the fact that the bony hinge is precisely positioned at axis 70 through the use of apex pin 300, i.e., the bony hinge extends parallel to the A-P slope and parallel to the sagittal plane. Furthermore, as the wedge-like opening 25 is created in the bone, the risk of bone cracking is minimized, due to the fact that apex pin 300 forms an oversized hole 95 (FIGS. 23A and 27) at the lateral end of the bone cut, i.e., "oversized" relative to the thickness of the osteotomy cut, whereby to reduce the occurrence of stress risers and the like as the bone is opened.

The surgeon uses opening jack 700 to open the bone to the extent necessary to correctly re-align the weight-bearing axis of the knee.

20. Then, with opening jack 700 still in place, an implant is positioned at the wedge-like opening 25 so as to hold the re-oriented bone with the desired orientation.

If desired, the implant may be a "generic" wedge-shaped implant such as the implant 27 shown in FIG. 3.

Figure 24:
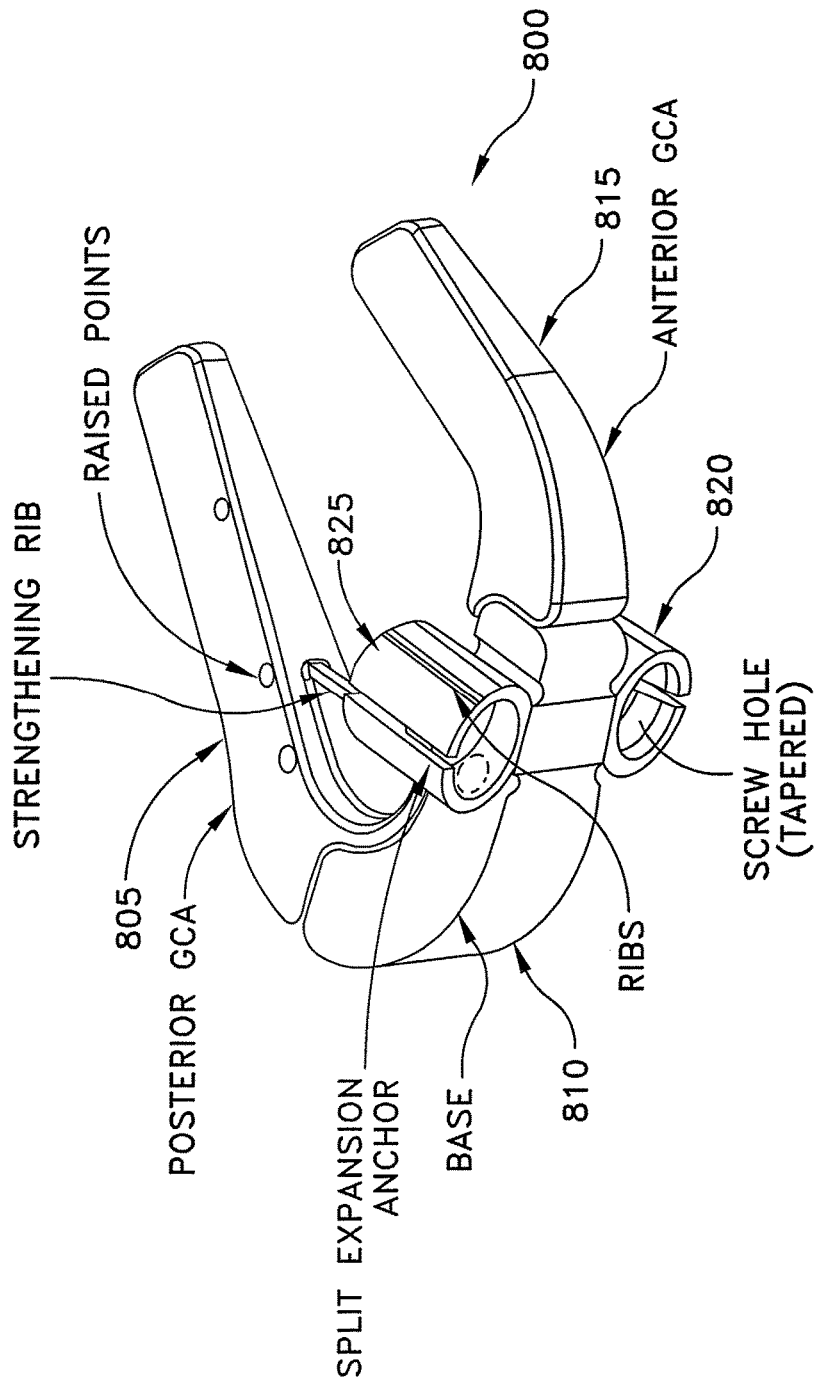

More preferably, however, and looking now at FIG. 24, there is shown a wedge-shaped implant 800 formed in accordance with the present invention. Wedge-shaped implant 800 is characterized by a wedge-like side profile configured to match the geometry of the wedge-like opening 25 (i.e., to match the prescribed correction angle of the open wedge, high tibial osteotomy). Preferably, wedge-shaped implant 800 is also formed so as to have a U-shaped top profile, such that it can form a barrier about the perimeter of the wedge-like opening 25, with the open end of the U-shaped implant positioned against the bony hinge, whereby to contain graft material (e.g., bone paste, bone cement, etc.) which may be positioned within the interior of the wedge-like opening 25. In one preferred form of the present invention, wedge-shaped implant 800 is formed so as to have an asymmetric configuration when viewed in a top view, so as to mate with the geometry of the tibia when the implant is positioned using an antero-medial approach. Wedge-shaped implant 800 is sized so as to match the known distance from the medial aspect of the tibia to the axis 70 of the bony hinge, which is set by the position of apex pin 300. Wedge-shaped implant 800 may be formed out of absorbable material or non-absorbable material, as desired.

Figure 25:
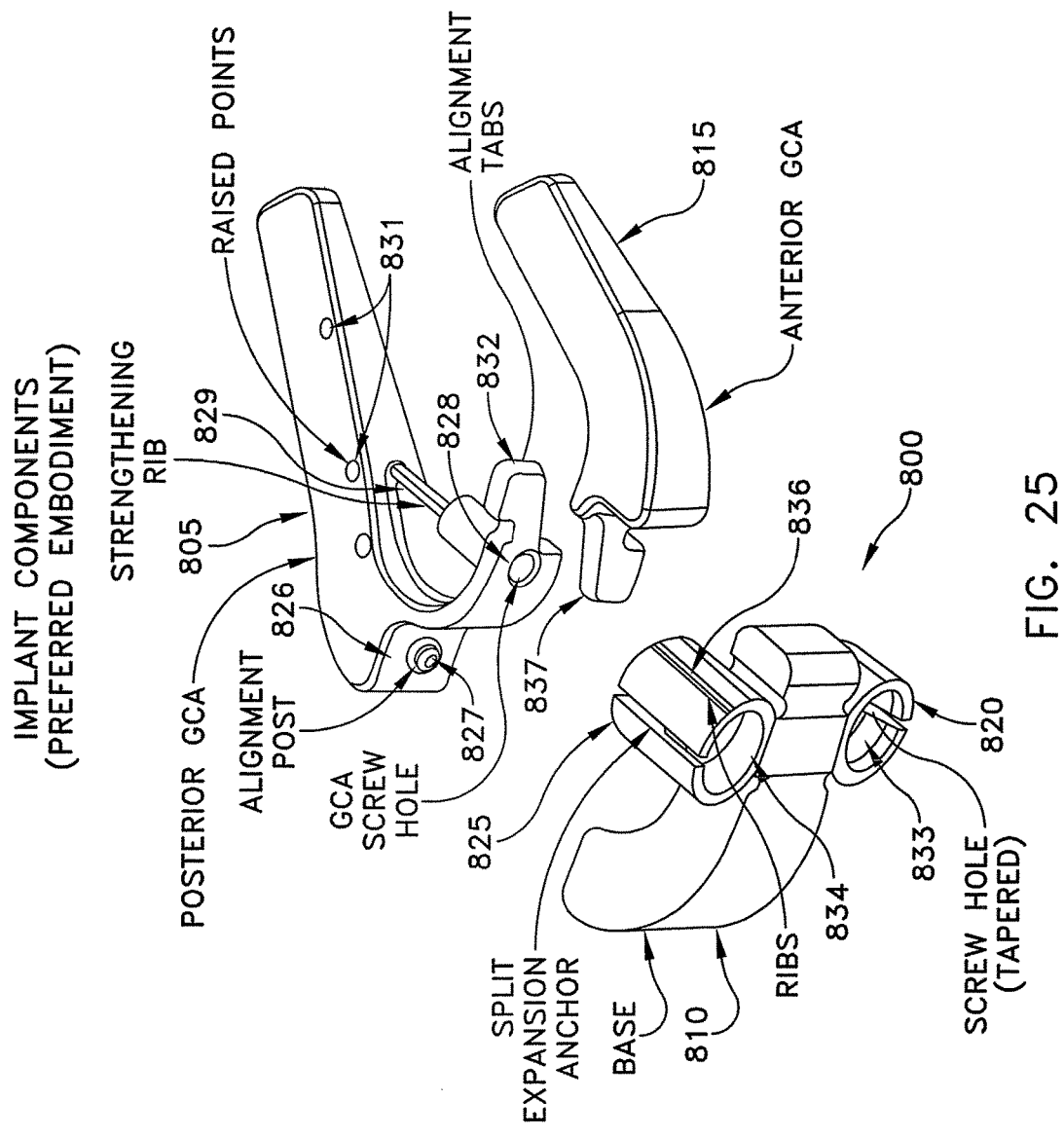
Figure 26:
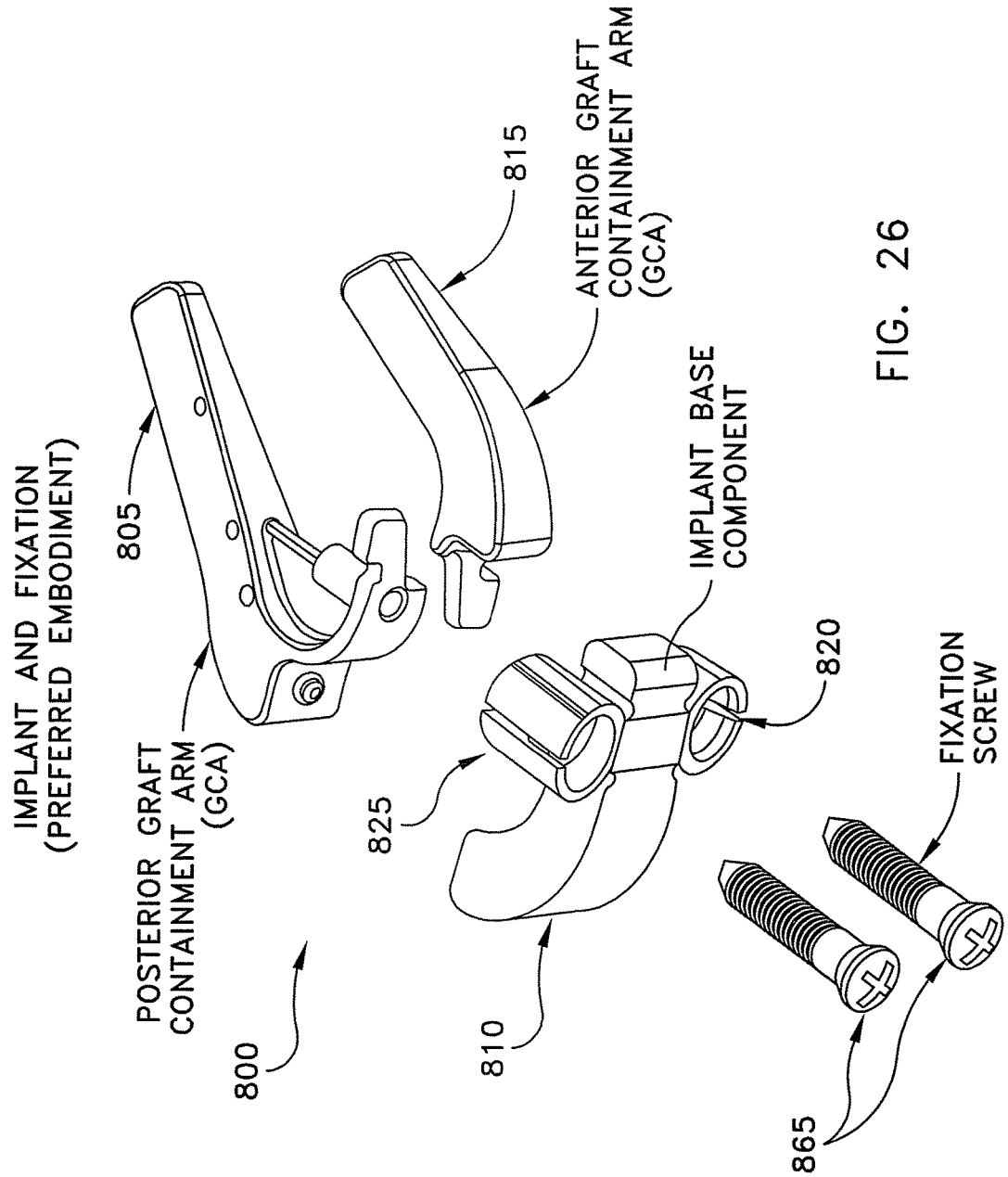

In one preferred form of the invention, and looking now at FIGS. 25 and 26, implant 800 preferably comprises a three-part assembly, comprising posterior graft containment arm (GCA) 805, a base 810 and an anterior graft containment arm (GCA) 815. The individual components of implant 800 may each be formed out of absorbable material and/or non-absorbable material, as desired. Furthermore, where one or more of the implant components is formed out of an absorbable material, the absorption characteristics of the material may vary as desired. By way of example but not limitation, base 810 may be formed out of a relatively slowly-absorbing material, while posterior graft containment arm (GCA) 805 and anterior graft containment arm (GCA) 815 may be formed out of a relatively faster-absorbing material. Base 810 preferably comprises a pair of keys 820, 825. Keys 820, 825 have a disposition which is complementary to the disposition of the keyholes 85, 90, i.e., where keyholes 85, 90 have an "over-under" configuration, keys 820, 825 also have an "over-under" configuration, as will hereinafter be discussed in further detail.

In one preferred form of the invention, implant 800 is formed so that posterior graft containment arm (GCA) 805 has a generally wedge-shaped profile including an engagement seat 826 comprising an alignment post 827, and an introducer hole 828 opening on the antero-medial side of the component for engagement with introducer 845 (see below). A strengthening rib 829 is preferably provided as shown. Additionally, raised points or dimples 831 may be provided to help fix posterior graft containment arm (GCA) 805 to the bone. An alignment tab 832 is provided for extension into upper keyhole 90 (FIG. 29) when posterior graft containment arm (GCA) 805 is positioned in the wedge-shaped opening 25.

And in one preferred form of the invention, base 805 is formed so that its keys 820, 825 each includes a bore 833, 834, respectively, with the keys being slotted longitudinally so as to permit expansion of the keys when screws 865 are thereafter deployed in the bores, whereby to help lock the implant against the hard cortical bone of the tibia. External ribs 836 may be provided on the outer surfaces of keys 820, 825 so as to help fix keys 820, 825 in keyholes 85, 90, respectively, when keys 820, 825 are expanded, as will hereafter be discussed in further detail. External ribs 836 may extend longitudinally (FIG. 25) or circumferentially (not shown). Keys 820, 825 protrude from the upper and lower surfaces of base implant 810, and accommodate shear loads which may be imposed across the implant. Furthermore, expansion of keys 820, 825 creates an interference fit with the cortical bone of the tibia, and can help support tensile loads which may be imposed across the implant. An alignment mechanism, e.g., a bore (not shown), is provided for mating with alignment post 827 of posterior graft containment arm (GCA) 805.

The bores 833, 834 may be axially aligned with the longitudinal axes of keys 820, 825, respectively. Alternatively, the bores 833, 834 may be arranged so that they diverge from one another, downwardly and upwardly, respectively, so as to direct screws 865 deeper into the adjacent portions of the tibia.

Anterior graft containment arm (GCA) 815 also comprises a generally wedge-shaped profile, and an alignment tab 837 is provided for extension into lower keyhole 85 when GCA 815 is positioned in the wedge-shaped opening 25.

Implant 800 is preferably assembled in situ.

In some instances, it may be advantageous to use an implant trial base 830 (FIGS. 27 and 28) in the course of preparing the tibia to receive implant 800, and in order to confirm proper fit of implant 800 in its seat.

More particularly, a pre-assembled assembly comprising posterior graft containment arm (GCA) 805, an implant trial base 830 and two guide sleeves 835, 840 are first inserted into wedge-like opening 25 in the bone using an introducer 845. See FIGS. 27 and 28.

Figure 27:
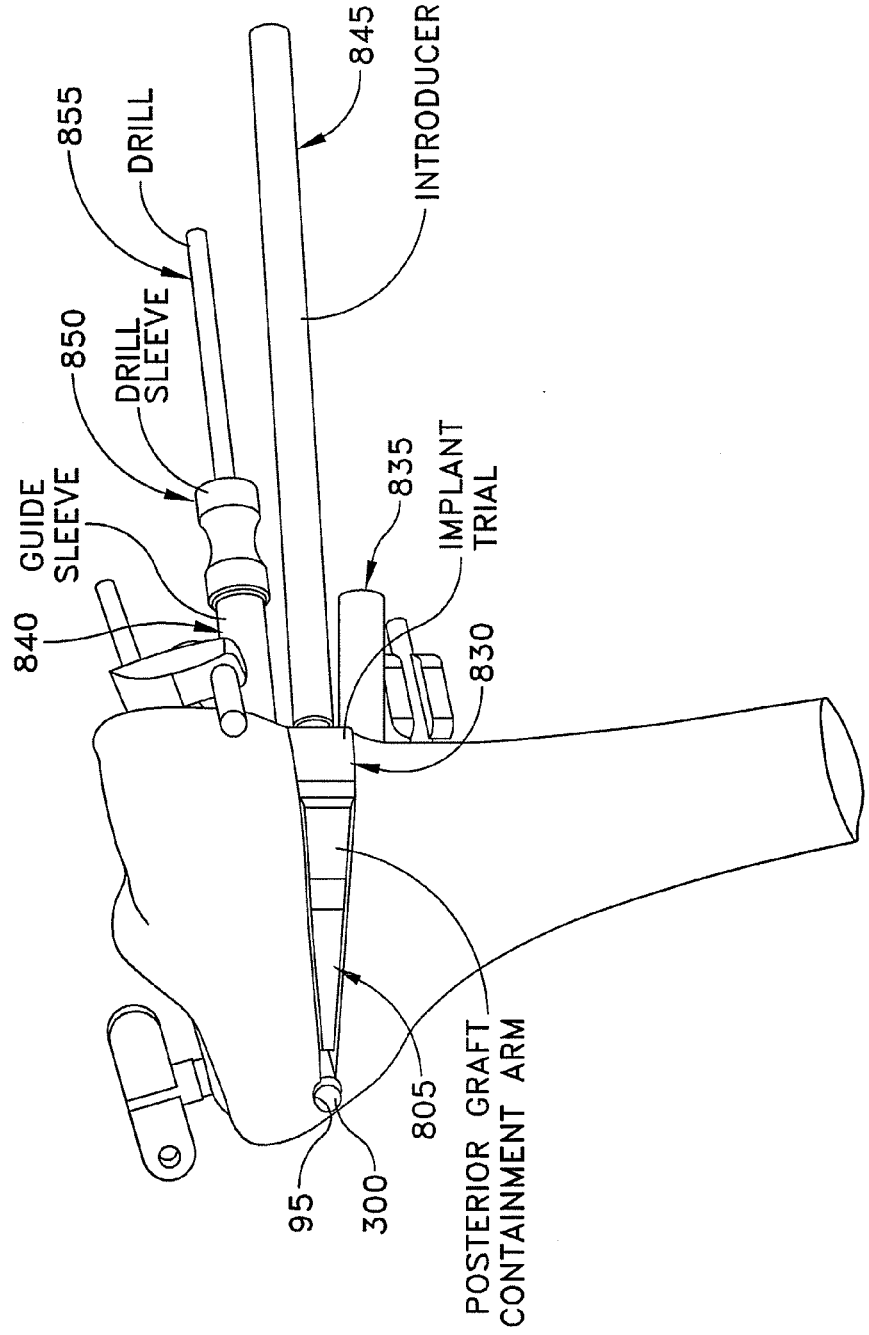
Figure 28:
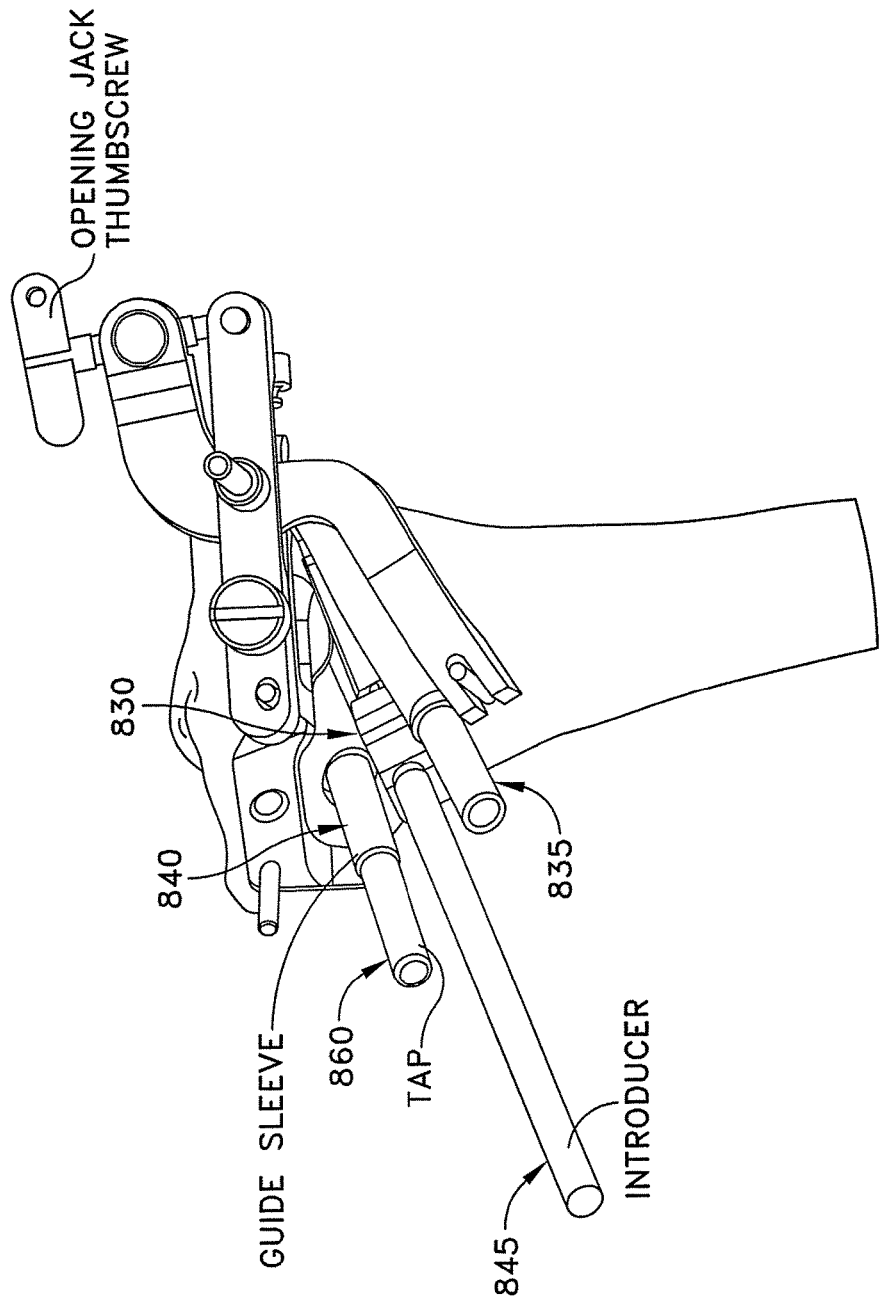

Next, a drill sleeve 850 and a drill 855 are inserted into guide sleeve 840 (FIG. 27). An upper hole is drilled into the tibia with the drill. The drilling procedure is then repeated for guide sleeve 835 so as to create a lower hole. Then drill sleeve 850 and drill 855 are removed from the surgical site. Next, a tap 860 is inserted into guide sleeve 840 and the upper hole is tapped. See FIG. 28. Then the tap is inserted into guide sleeve 835 and the lower hole is tapped. Then tap 860 is removed from the surgical site.

21. Next, posterior graft containment arm (GCA) 805 is released from introducer 845, and then introducer 845 and implant trial base 830 are removed. Posterior graft containment arm (GCA) 805 remains in wedge-like opening 25.

22. Then, if desired, graft material is packed into the osteotomy opening.

23. Next, anterior graft containment arm (GCA) 815 is placed into the osteotomy opening and aligned with the prepared implant holes. See FIG. 29. If necessary, jack screw 735 is rotated as needed so as to facilitate insertion of anterior GCA 815. At this point in the procedure, posterior graft containment arm (GCA) 805 and anterior graft containment arm (GCA) 815 are positioned in wedge-like opening 25.

24. Then implant base 810 is inserted into the prepared osteotomy, with keys 820 and 825 seated in tibial holes 85 and 90, respectively, and with base 810 capturing posterior graft containment arm (GCA) 805 and anterior graft containment arm (GCA) 815 against the bony hinge. Keys 820 and 825, seating in keyholes 85 and 90, help ensure a precise fit of the implant to the bone. As this is done, jack screw 735 is adjusted as necessary so as to facilitate insertion of the base into the osteotomy. Then jack screw 735 is tightened slightly so as to ensure that the implant components are fully seated into the osteotomy wedge, with at least implant base 810, and preferably also posterior graft containment arm (GCA) 805 and anterior graft containment arm (GCA) 815, providing load bearing support to the tibia. Next, fixation screws 865 are inserted through keys 820 and 825 in base 810 and into the tapped holes in the tibia, and then tightened into place. As this occurs, fixation screws 865 expand keys 820, 825 within keyholes 85, 90 so as to lock keys 820, 825 to the adjacent cortical bone, and fixation screws 865 extend into the tibia, so as to further lock the implant in position. See FIG. 30. Finally, opening jack 700, positioning guide 100, apex pin 300, distal pin 410, frontal pin 145 and A-M pin 150 are removed from the surgical site, and the incision closed.

Providing implant 800 with two graft containment arms, e.g., posterior graft containment arm (GCA) 805 and anterior graft containment arm (GCA) 815, is frequently preferred. However, in some circumstances, it may be desirable to omit one or both of posterior graft containment arm (GCA) 805 and anterior graft containment arm (GCA) 815. Thus, in one preferred form of the invention, implant 800 comprises only base 810 and omits both posterior graft containment arm (GCA) 805 and anterior graft containment arm (GCA) 815.

Providing implant 800 with a pair of keys 820, 825 is generally preferred. However, in some circumstances, it may be desirable to omit one or the other, or both, of keys 820, 825. Furthermore, in other circumstances, it may be desirable to provide more than two keys, e.g., to provide three keys.

Furthermore, each of the keys 820, 825 may include more than one bore 833, 834. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

The use of apex pin 300 is significant for a number of reasons:

(1) the oversized, circular diameter hole 95 (FIG. 23A) formed in the tibia by apex pin 300, which forms the limit of bone cut 20, effectively displaces the stress forces created at the edge of the bony hinge when the cut is opened to form the wedge-like opening 25, thereby adding significantly to the effective strength of the bony hinge;

(2) by using apex pin 300 to control the length of bone cut 20 (as measured from the medial aspect of the tibia to the apex pin), the seat for the implant is always of known size, thereby simplifying proper fitting of the implant to its seat in the bone, and also reducing the inventory of different-sized implants which must be on hand during the surgery;

(3) with apex pin 300 in place, bone resecting tools can be used with increased confidence, without fear of inadvertently cutting into, or even through, the bony hinge; and (4) since apex pin 300 controls the depth of bone cut 20, the implant can be reliably manufactured to appropriately address the required degree of correction needed to effect knee realignment (e.g., a 4 degree implant slope will always provide a 4 degree angle of correction).

Furthermore, the provision of (i) apex pin 300, posterior protector 500 and tibial tubercle locating tab 135 creates a "protection zone", and (ii) cutting guide 600 creates a closely constrained cutting path for saw blade 625, thereby together ensuring that only the desired portion of the bone is cut. Among other things, the provision of posterior protector 500 ensures that the delicate neurological and vascular tissues at the back of the knee are protected during cutting of the tibia.

The provision of keyholes 85, 90 in the tibia, and the provision of keys 820, 825 in the implant, is significant inasmuch as they provide improved stabilization of the implant, particularly against rotational and shearing forces. This is particularly true inasmuch as keyholes 85, 90 extend through the hard cortical bone at the periphery of the tibia.

Implant with "Side-by-Side" Key Configuration

Figure 31:
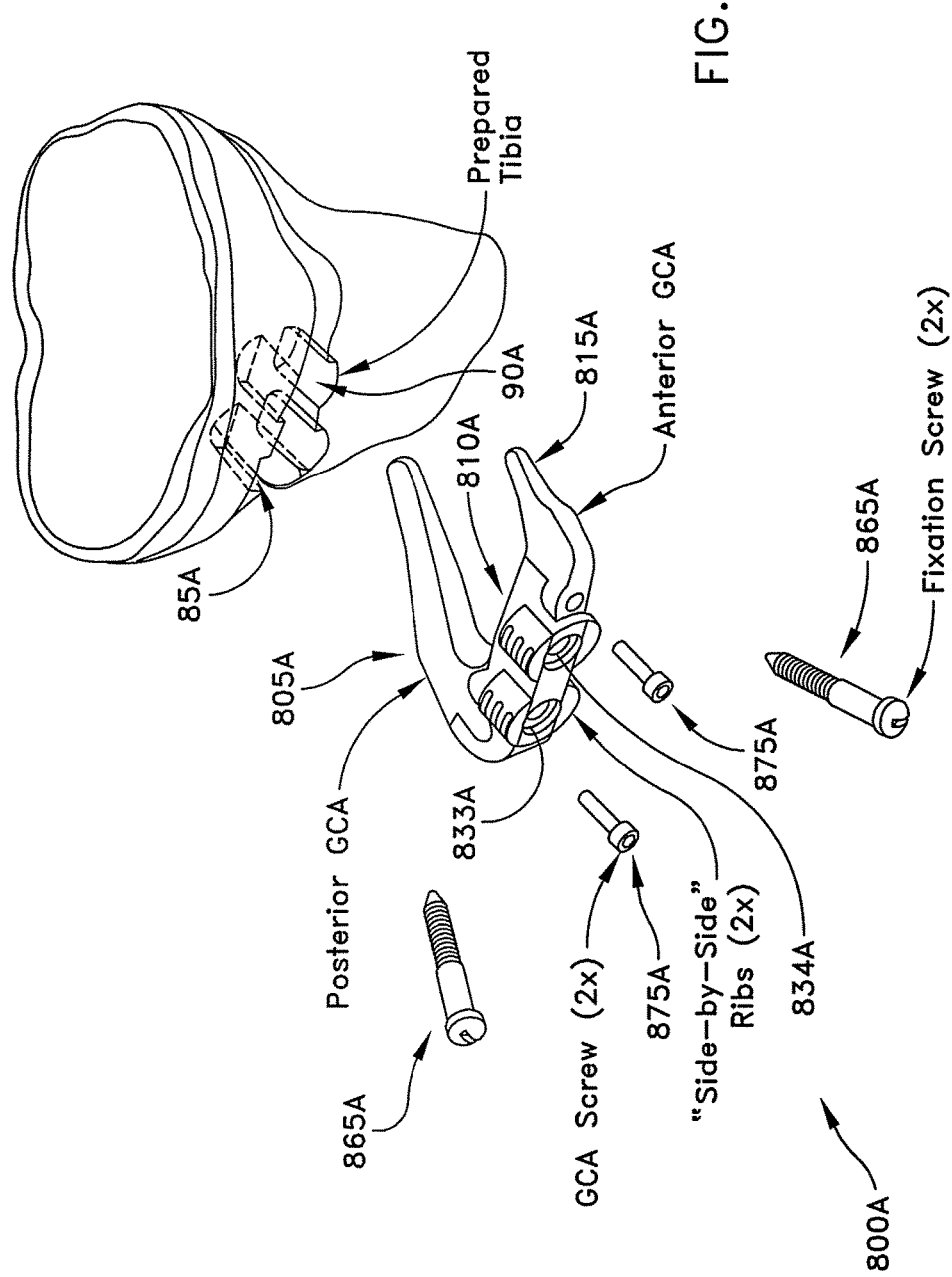
Figure 33:
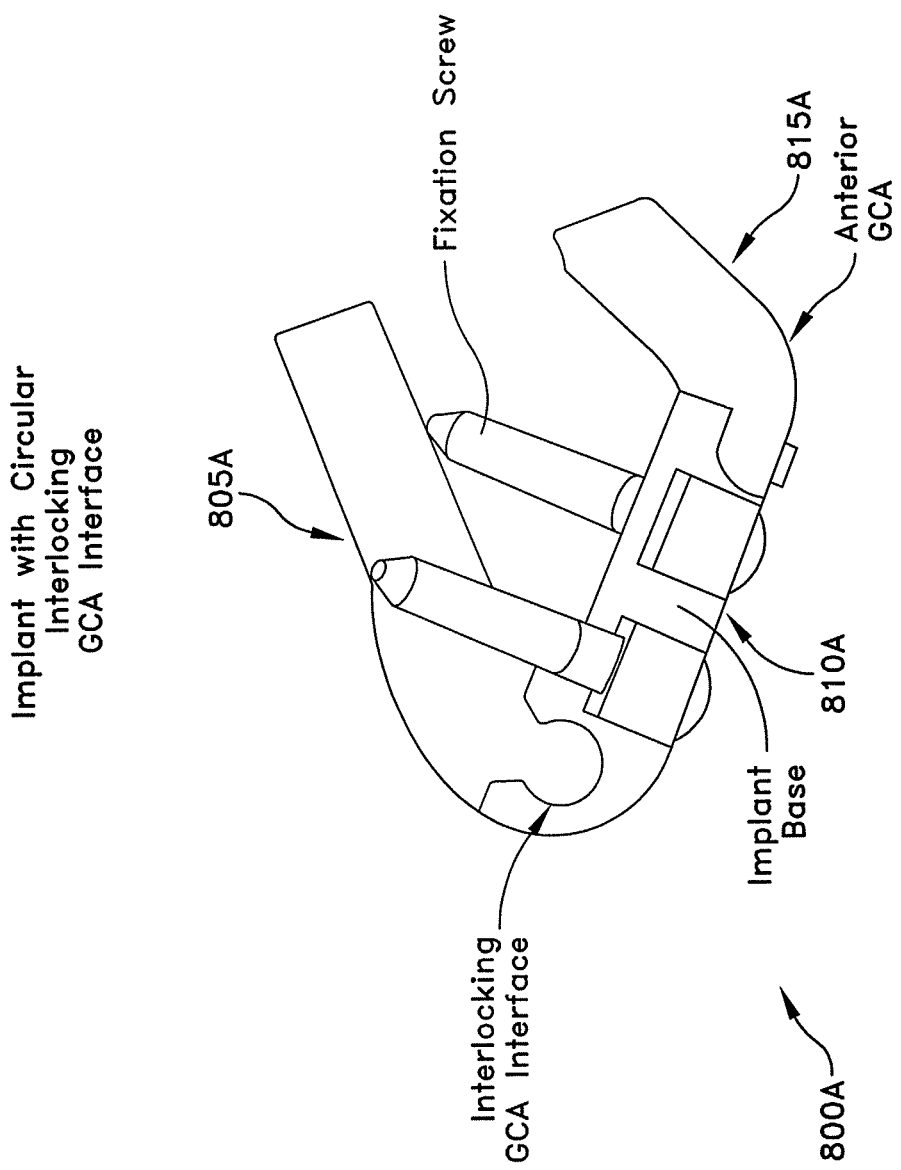

Looking next at FIGS. 31-33, there is shown an implant 800A also formed in accordance with the present invention. Implant 800A is generally similar to the implant 800 disclosed above, except that implant 800A has its keys disposed in a "side-by-side" configuration, rather than the "over-under" key configuration of implant 800, as will hereinafter be discussed in further detail. Furthermore, implant 800A also provides an alternative approach for joining the posterior graft containment arm (GCA) to the base, and an alternative approach for joining the anterior graft containment arm (GCA) to the base, as will hereinafter also be discussed in further detail.

More particularly, and still looking now at FIGS. 31-33, implant 800A comprises a posterior graft containment arm (GCA) 805A, a base 810A and an anterior graft containment arm (GCA) 815A. Base 810A preferably comprises a pair of keys 820A, 825A. Keys 820A, 825A are laterally displaced along the width of base 810A, in a "side-by-side" configuration. This is in contrast to the construction of implant 800, which uses an "over-under" configuration for its keys 820, 825 (FIG. 24). Among other things, it has been found that the "side-by-side" configuration provides, at the base of the implant, excellent load-bearing characteristics and substantial resistance to rotational and shear forces.

Posterior graft containment arm (GCA) 805A includes a tab 870A, and base 810A includes a groove 873A, whereby posterior graft containment arm (GCA) 805A can mate with base 810A. A screw 875A is used to secure tab 870A in groove 873A, and hence posterior graft containment arm (GCA) 805 to base 810. Anterior graft containment arm (GCA) 815A includes a flange 878A, and implant base 810A includes a recess 881A, whereby anterior graft containment arm (GCA) 815A can mate with base 810A. Another screw 875A is used to secure flange 878A in recess 881A, and hence anterior graft containment arm (GCA) 815 to base 810.

Posterior graft containment arm (GCA) 805A, and/or anterior graft containment arm (GCA) 815A, may include raised points or dimples 831A.

Keys 820A, 825A each include a bore 833A, 834A, respectively. Bores 833A, 834A receive fixation screws 865A for fixing implant 800A to the tibia. Bores 833A, 834A preferably diverge from the longitudinal axes of keys 820A, 825A, respectively, so as to direct fixation screws 865A downwardly or upwardly into the adjacent portions of the tibia. Keys 820A, 825A may also include external ribs 836A. External ribs 836A may extend longitudinally (not shown) or circumferentially (FIG. 32). Keys 820A, 825A may also be slotted (i.e., in a manner analogous to the slots provided in keys 820, 825 of implant 800), whereby to permit keys 820A, 825A to expand when fixation screws 865A are received in bores 833A, 834A.

Figure 34:
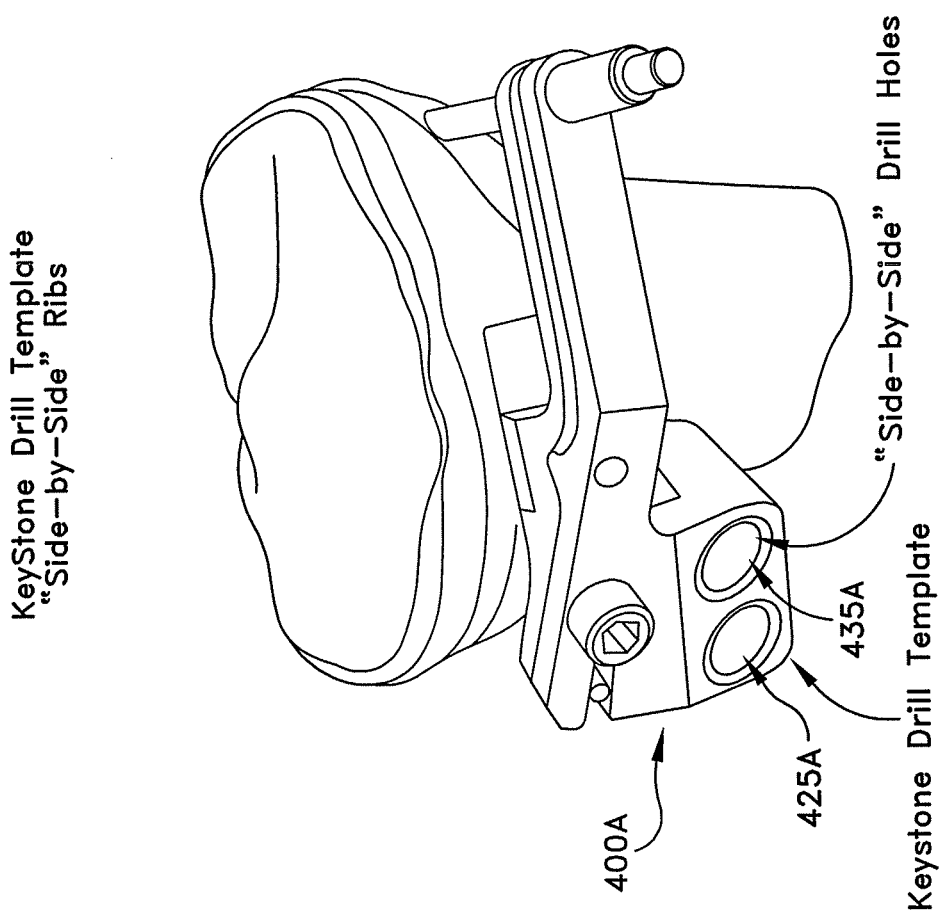
FIG. 34 is a schematic view showing a keyhole drill guide which may be used in conjunction with the wedge-shaped implant shown in FIGS. 31-33.

In order to provide appropriate keyholes 85A, 90A (FIG. 31) for receiving keys 820A, 825A, a keyhole drill guide 400A (also sometimes referred to as a "keystone drill template") may be used (FIG. 34). Keyhole drill guide 400A is generally similar to the keyhole drill guide 400 disclosed above, except that keyhole drill guide 400A has its two guide holes 425A, 435A disposed in a "side-by-side" disposition, rather than the "over-under" disposition of the two guide holes 425, 435 of drill guide 400.

Implant 800A (and drill guide 400A) may be used in an open wedge, high tibial osteotomy in a manner which is generally similar to that previously described with respect to implant 800 (and drill guide 400).

Providing implant 800A with two graft containment arms, e.g., posterior graft containment arm (GCA) 805A and anterior graft containment arm (GCA) 815A, is frequently preferred. However, in some circumstances, it may be desirable to omit one or both of posterior graft containment arm (GCA) 805A and anterior graft containment arm (GCA) 815A. Thus, in one preferred form of the invention, implant 800A comprises only base 810A and omits both posterior graft containment arm (GCA) 805A and anterior graft containment arm (GCA) 815A.

Providing implant 800A with a pair of keys 820A, 825A is generally preferred. However, in some circumstances, it may be desirable to omit one or the other, or both, of keys 820A, 825A. Furthermore, in other circumstances, it may be desirable to provide more than two keys, e.g., to provide three keys.

Furthermore, each of the keys 820A, 825A may include more than one bore 833A, 834A. Thus, for example, a key may include two bores, one angled upwardly so as to direct a fixation screw upwardly into the tibia above the key, and/or one angled downwardly so as to direct a fixation screw downwardly into the tibia below the key.

Figure 35:
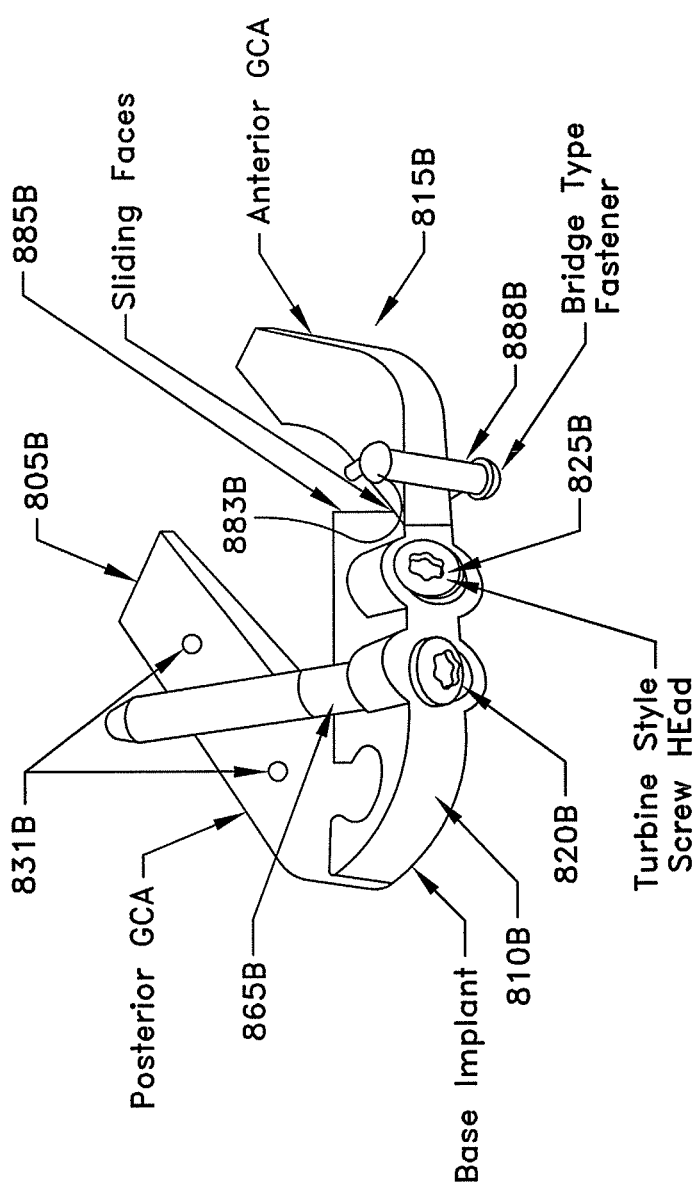
FIG. 35 is a schematic view showing another wedge-shaped implant formed in accordance with the present invention.

Implant with Alternative Approach for Joining Anterior Graft Containment Arm (GCA) to Implant Base Looking next at FIG. 35, there is shown another implant 800B also formed in accordance with the present invention. Implant 800B is generally similar to the implant 800A disclosed above, except that implant 800B provides an alternative approach for joining the anterior graft containment arm (GCA) to the implant base, among other things.

More particularly, and still looking now at FIG. 35, implant 800B comprises a posterior graft containment arm (GCA) 805B, a base 810B and an anterior graft containment arm (GCA) 815B. Base 810B preferably comprises a pair of keys 820B, 825B. Keys 820B, 825B are laterally displaced along the width of base 810B, in a "side-by-side" configuration. Again, this is in contrast to the construction of implant 800, which uses an "over-under" configuration for its keys 820, 825 (FIG. 24).

Posterior graft containment arm (GCA) 805B includes a tab 870B, and base 810B includes a groove 873B, whereby posterior graft containment arm (GCA) 805B can mate with base 810B. Anterior graft containment arm (GCA) 815A includes a slide face 883B, and implant base 810B includes an opposing slide face 885B, whereby anterior graft containment arm (GCA) 815B can mate with base 810B. A bridge-type fastener 888B is used to secure anterior graft containment arm (GCA) 815B in position, with arm slide face 883B engaging base slide face 885B, after the implant is positioned within positioned within the wedge-like opening 25.

Posterior graft containment arm (GCA) 805B, and/or anterior graft containment arm (GCA) 815B, may include raised points or dimples 831B.

Keys 820B, 825B each include a bore 833B, 834B, respectively. Bores 833B, 834B receive fixation screws 865B for fixing implant 800B to the tibia. Bores 833B, 834B preferably diverge from the longitudinal axes of keys 820B, 825B, respectively, so as to direct fixation screws 865B downwardly or upwardly into the adjacent portions of the tibia. Keys 820B, 825B may also include external ribs 836B. External ribs 836B may extend longitudinally or circumferentially. Keys 820B, 825B may also be slotted (i.e., in a manner analogous to the slots provided in keys 820, 825 of implant 800), whereby to permit keys 820B, 825B to expand when fixation screws 865B are received in bores 833B, 834B.

Implant 800B may be used in an open wedge, high tibial osteotomy in a manner which is generally similar to that previously described with respect to implant 800.

Providing implant 800B with two graft containment arms, e.g., posterior graft containment arm (GCA) 805B and anterior graft containment arm (GCA) 815B, is frequently preferred. However, in some circumstances, it may be desirable to omit one or both of posterior graft containment arm (GCA) 805B and anterior graft containment arm (GCA) 815B. Thus, in one preferred form of the invention, implant 800B comprises only base 810B and omits both posterior graft containment arm (GCA) 805B and anterior graft containment arm (GCA) 815B.

Providing implant 800B with a pair of keys 820B, 825B is generally preferred. However, in some circumstances, it may be desirable to omit one or the other, or both, of keys 820B, 825B. Furthermore, in other circumstances, it may be desirable to provide more than two keys, e.g., to provide three keys.

Furthermore, each of the keys 820B, 825B may include more than one bore 833B, 834B. Thus, for example, a key may include two bores, one angled upwardly so as to direct a fixation screw upwardly into the tibia above the key, and/or one angled downwardly so as to direct a fixation screw downwardly into the tibia below the key.

Implant with Shear Rib

Figure 36:
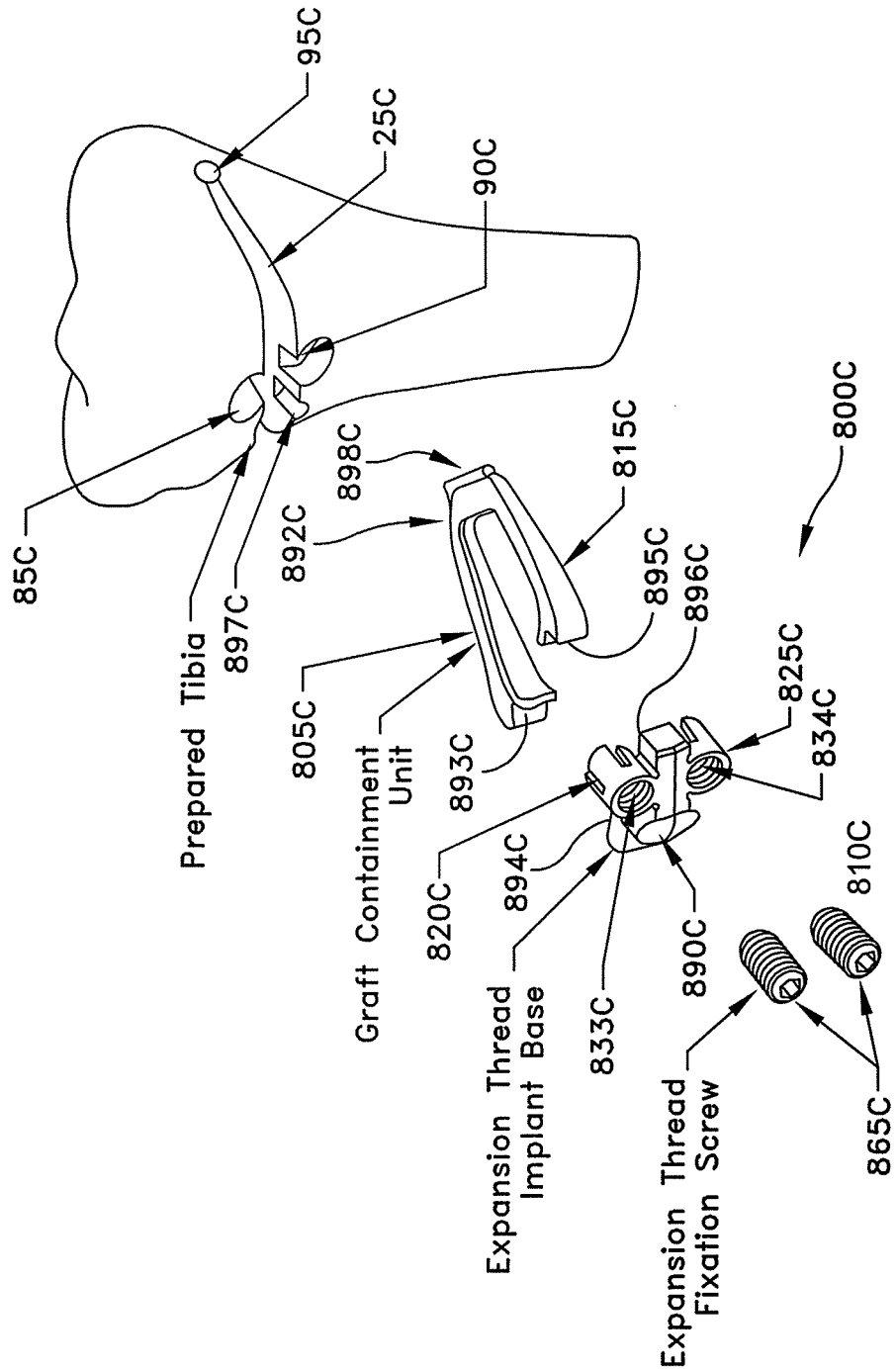
FIGS. 36-38 are schematic views showing still another wedge-shaped implant formed in accordance with the present invention.
Figure 37:
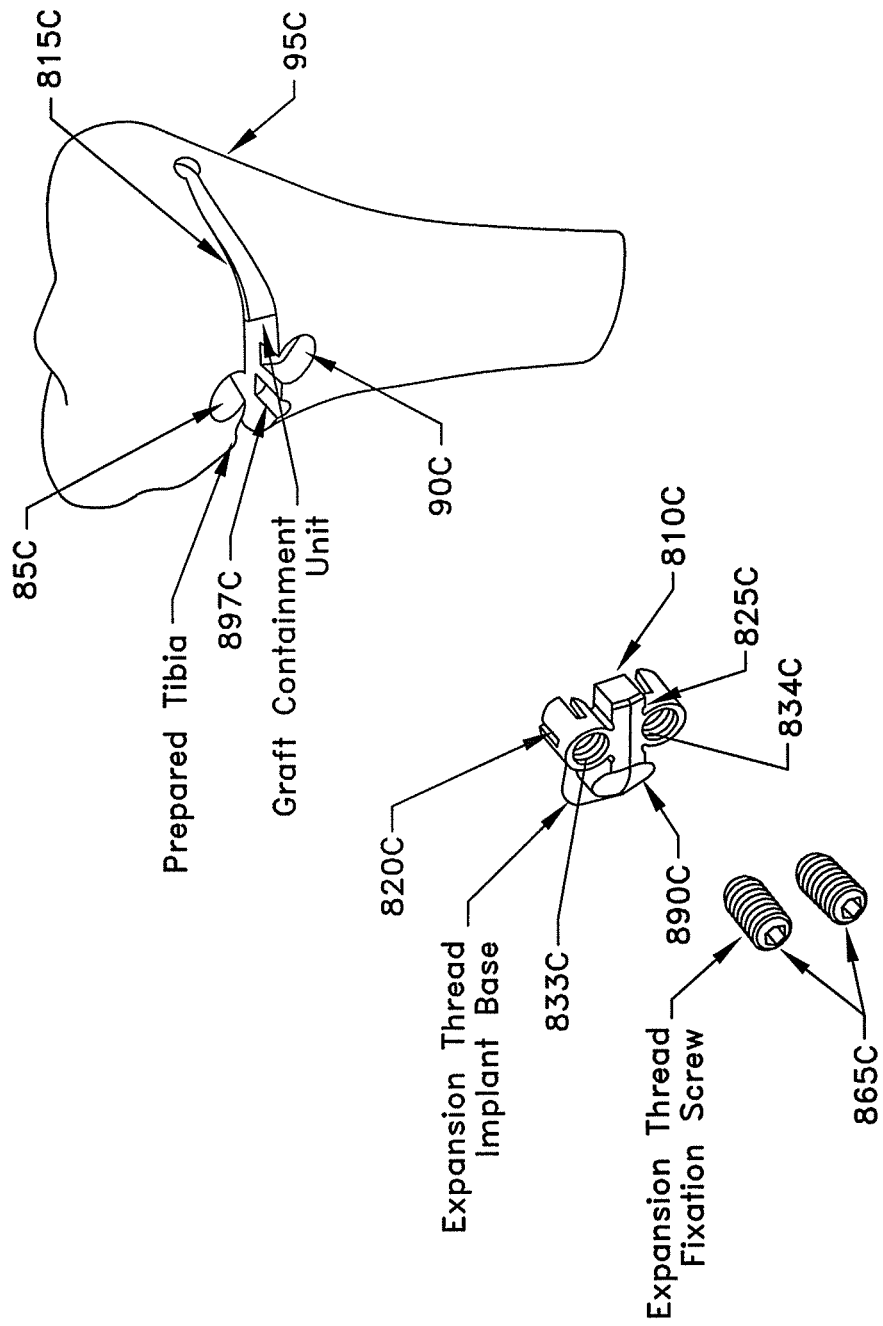
Figure 38:
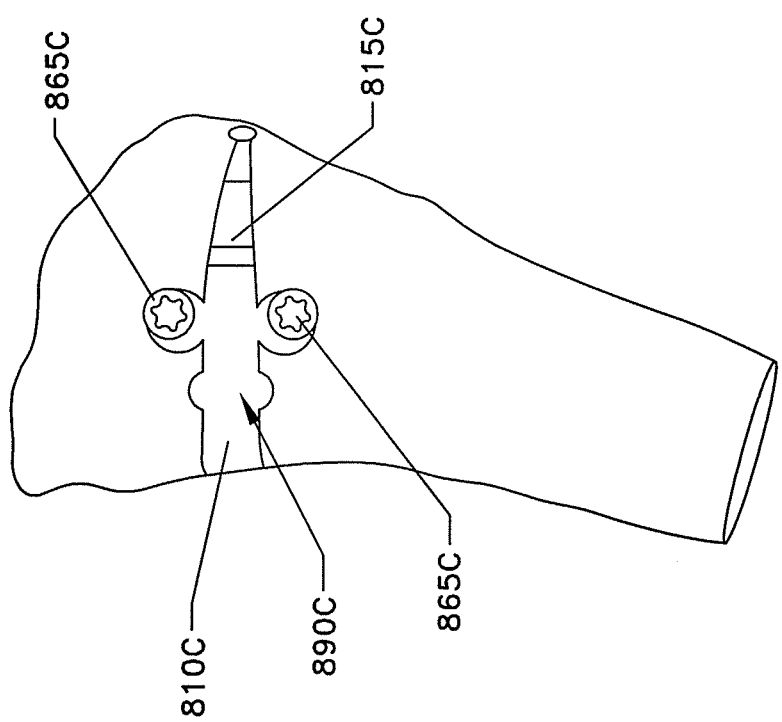

Looking next at FIGS. 36-38, there is shown an implant 800C also formed in accordance with the present invention. Implant 800C is generally similar to the implant 800 disclosed above, except that implant 800C has a shear rib 890C on its base, laterally displaced from the two keys (which are themselves arranged in an "over-under" configuration), as will hereinafter be discussed in further detail. Furthermore, implant 800C also provides an alternative approach for joining the posterior graft containment arm (GCA) to the base, and an alternative approach for joining the anterior graft containment arm (GCA) to the base, as will hereinafter also be discussed in further detail. Furthermore, implant 800C also provides a means for joining the distal end of posterior graft containment arm (GCA) 805C to the distal end of anterior graft containment arm (GCA) 815C, as will hereinafter also be discussed in further detail.

More particularly, and still looking now at FIGS. 36-38, implant 800C comprises a posterior graft containment arm (GCA) 805C, a base 810C and an anterior graft containment arm (GCA) 815C. Preferably a bridge 892C connects the distal end of posterior graft containment arm (GCA) 805C with the distal end of anterior graft containment arm (GCA) 815C. If desired, bridge 892C may be provided with a distal tab 898C to be received in oversized hole 95C. Distal tab 898C serves to improve the alignment and stability of implant 800C when seated in wedge-like opening 25C. A shear rib 890C is formed in base 810C, laterally displaced from the two keys 820C, 825C, which are arranged in an "over-under" configuration.

Posterior graft containment arm (GCA) 805C includes a recess 893C, and base 810C includes a shoulder 894C, whereby posterior graft containment arm (GCA) 805C can mate with base 810C. Anterior graft containment arm (GCA) 815C includes a recess 895C, and implant base 810C includes a shoulder 896C, whereby anterior graft containment arm (GCA) 815C can mate with base 810C.

Posterior graft containment arm (GCA) 805C, and/or anterior graft containment arm (GCA) 815C, may include raised points or dimples 831C.

Keys 820C, 825C each include a bore 833C, 834C, respectively. Bores 833C, 834C receive fixation screws 865C for fixing implant 800C to the tibia. The bores 833C, 834C may be axially aligned with the longitudinal axes of keys 820C, 825C, respectively. Alternatively, the bores 833C, 834C may be arranged so that they diverge from one another, downwardly and upwardly, respectively, so as to direct screws 865C deeper into the adjacent portions of the tibia. Keys 820C, 825C may also include external ribs 836C. External ribs 836C may extend longitudinally or circumferentially. Keys 820C, 825C may also be slotted (i.e., in a manner analogous to the slots provided in keys 820, 825 of implant 800), whereby to permit keys 820C, 825C to expand when fixation screws 865C are received in bores 833C, 834C.

Shear rib 890C is laterally offset from keys 820C, 825C. Shear rib 890C projects above and below the top and bottom surfaces of base 810C. Among other things, it has been found that the provision of shear rib 890C provides, at the base of the implant, excellent load-bearing characteristics and substantial resistance to rotational and shear forces.

Figure 39:
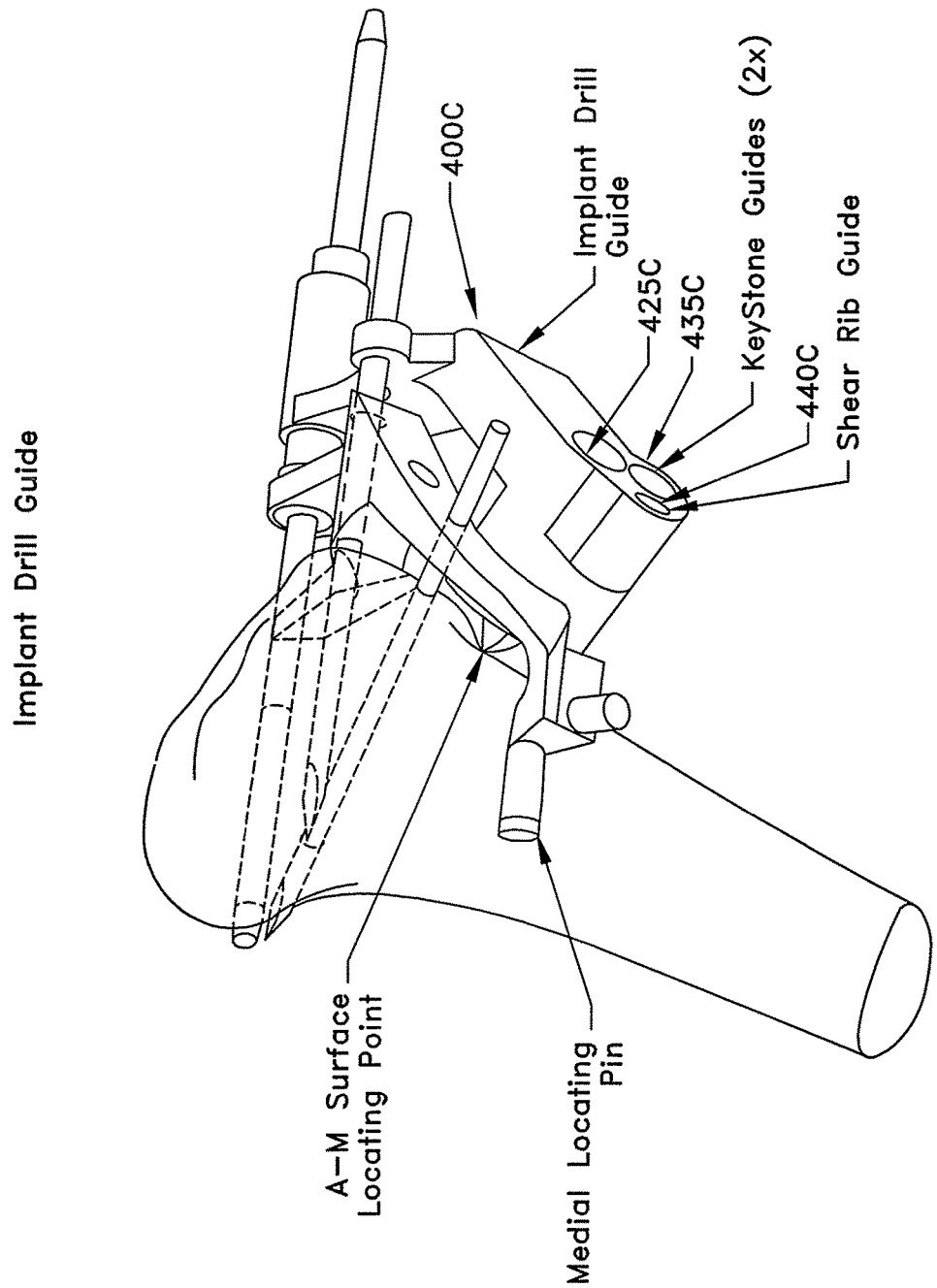
FIGS. 39-41 are schematic views showing a keyhole drill guide and an end mill which may be used in conjunction with the wedge-shaped implant shown in FIGS. 36-38.
Figure 40:
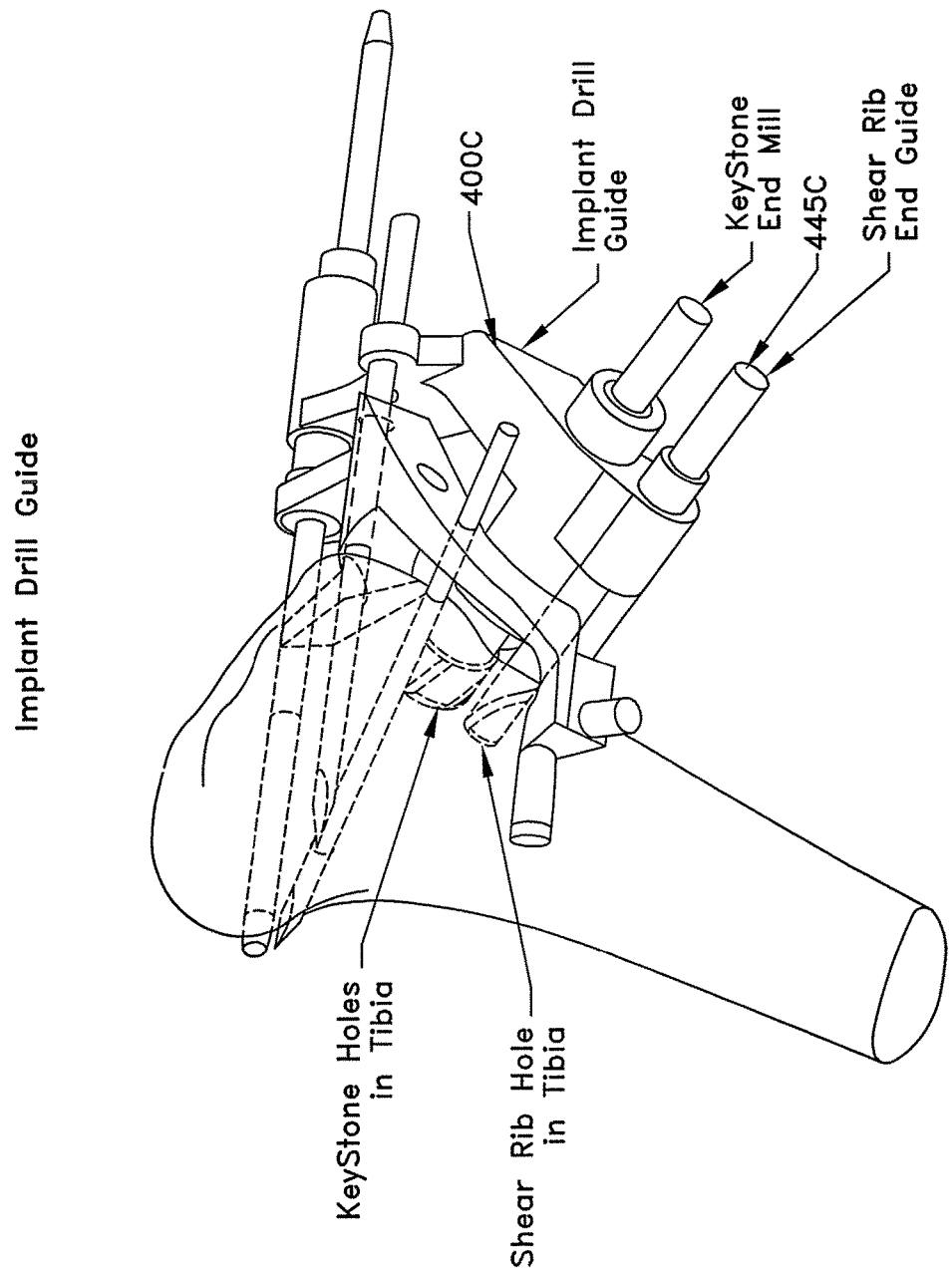

In order to provide appropriate keyholes 85C, 90C (FIG. 36) for receiving keys 820C, 825C, and also for providing a shear rib keyhole 897C for receiving shear rib 890C, a keyhole drill guide 400C (also sometimes referred to as a "keystone guide") may be used (FIGS. 39 and 40). Keyhole drill guide 400C is generally similar to the keyhole drill guide 400 disclosed above, except that keyhole drill guide 400C has, in addition to its two guide holes 425C, 435C, a shear rib guidehole 440C for forming shear rib keyhole 897C.

Implant 800C (and drill guide 400C) may be used in an open wedge, high tibial osteotomy in a manner which is generally similar to that previously described with respect to implant 800 (and drill guide 400), except that the bridged graft containment unit, i.e., posterior graft containment arm (GCA) 805C, bridge 892C and anterior graft containment arm (GCA) 815C, is installed as a single construction. Furthermore, when drill guide 400C is used to form keyholes 85C and 90C, it is also used to form shear rib keyhole 897C.

Providing implant 800C with two graft containment arms, e.g., posterior graft containment arm (GCA) 805C and anterior graft containment arm (GCA) 815C, is frequently preferred. However, in some circumstances, it may be desirable to omit one or both of posterior graft containment arm (GCA) 805C and anterior graft containment arm (GCA) 815C. Thus, in one preferred form of the invention, implant 800C comprises only base 810C and omits both posterior graft containment arm (GCA) 805C and anterior graft containment arm (GCA) 815C.

Providing implant 800C with a pair of keys 820C, 825C is generally preferred. However, in some circumstances, it may be desirable to omit one or the other, or both, of keys 820C, 825C. Furthermore, in other circumstances, it may be desirable to provide more than two keys, e.g., to provide three keys.

Furthermore, each of the keys 820C, 825C may include more than one bore 833C, 834C. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

Figure 41:
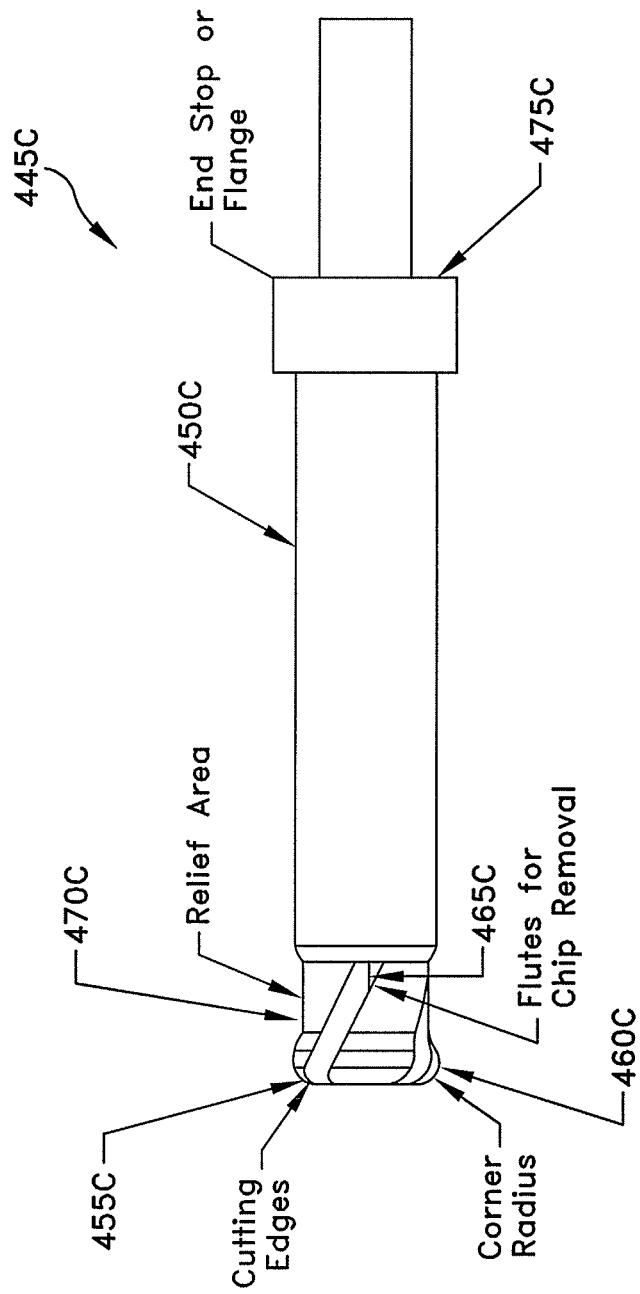

If desired, shear rib keyhole 897C can be formed using a conventional drill. More preferably, however, and looking now at FIGS. 40 and 41, shear rib keyhole 897C is formed using a shear rib end mill 445C. Shear rib end mill 445C generally comprises a shaft 450C having cutting edges 455C, a corner radius 460C and flutes 465C. A relief area 470C is formed just proximal to corner radius 460C. An end stop 475C limits, through engagement with drill guide 400C, the depth of shear rib keyhole 897C.

Implant with Expansion Thread Fixation Screws which Terminate within the Keys

Figure 42:
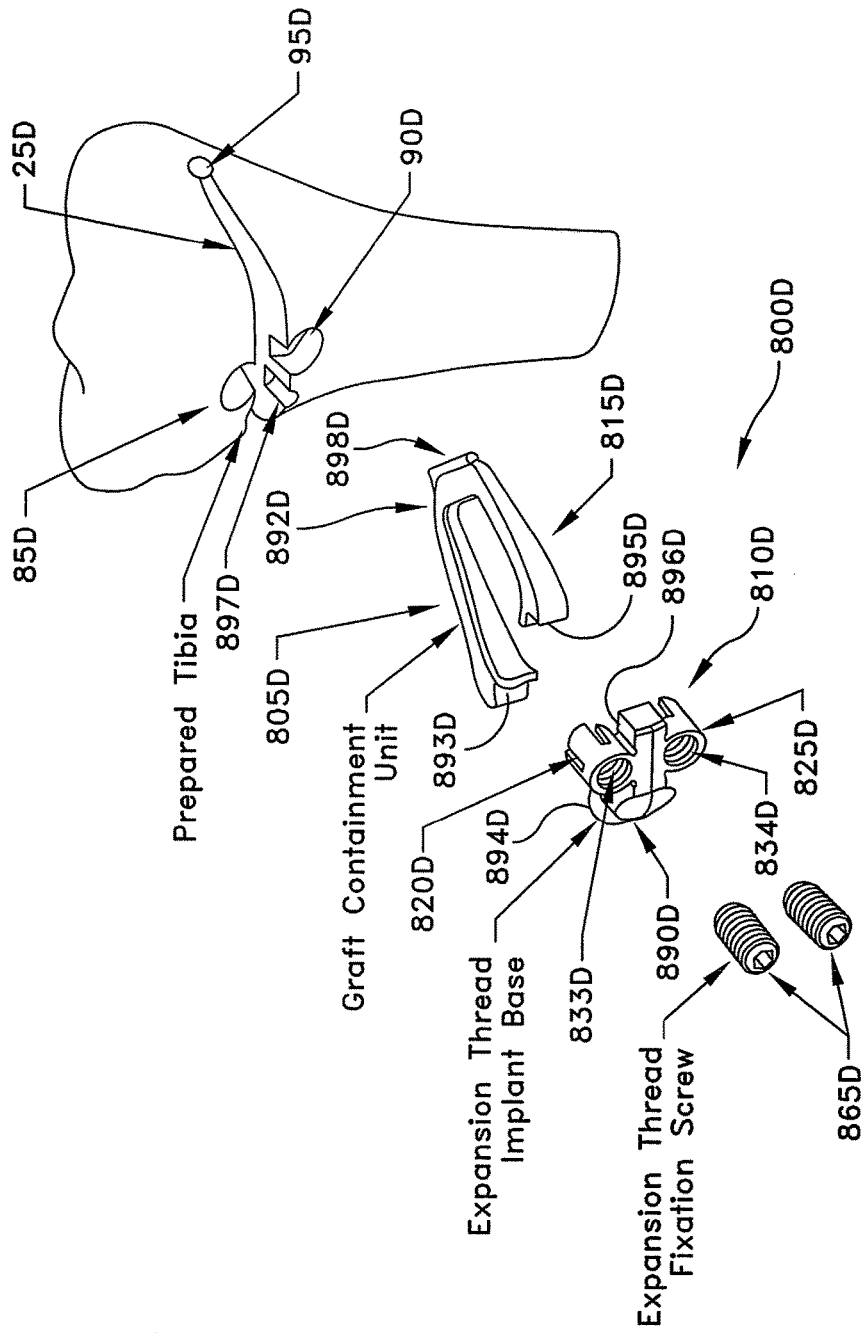
FIGS. 42-44 are schematic views showing yet another wedge-shaped implant formed in accordance with the present invention.
Figure 43:
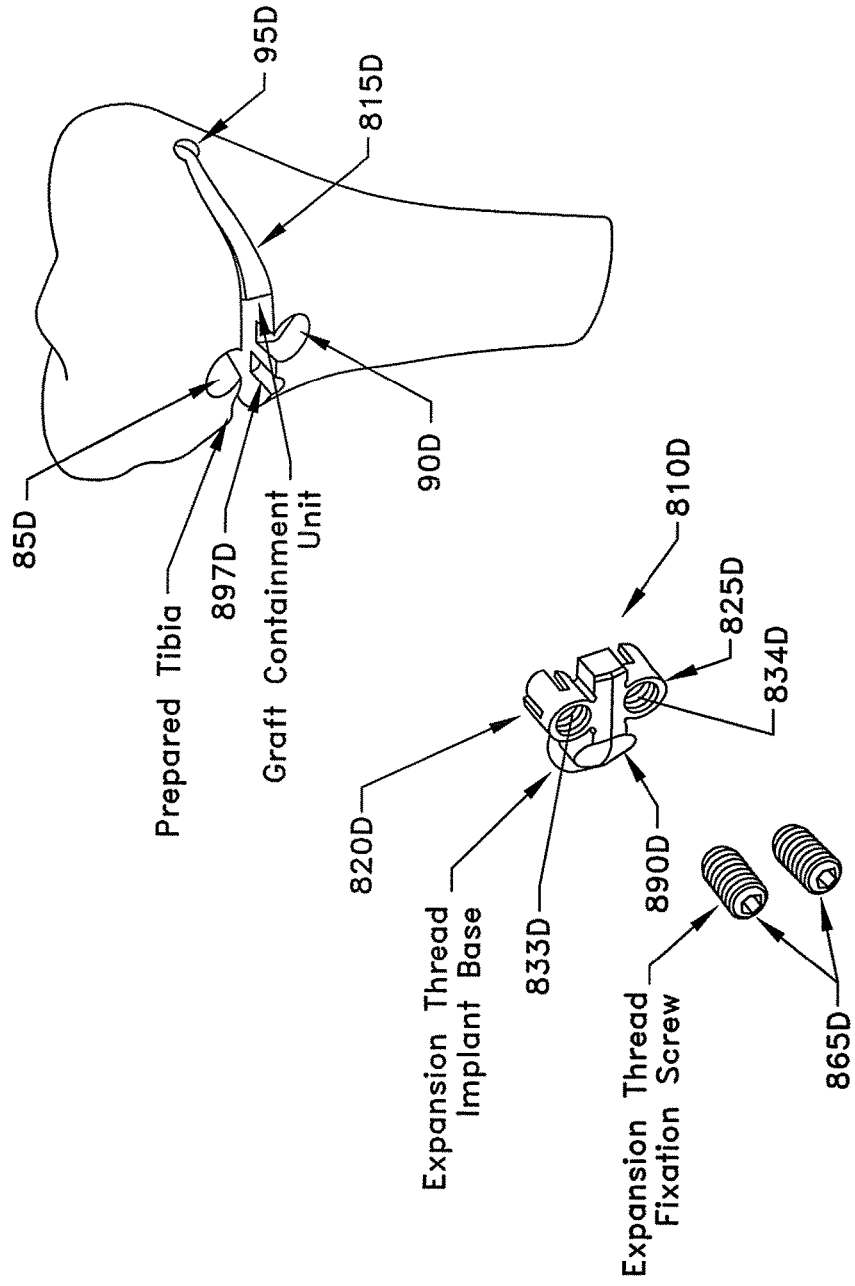
Figure 44:
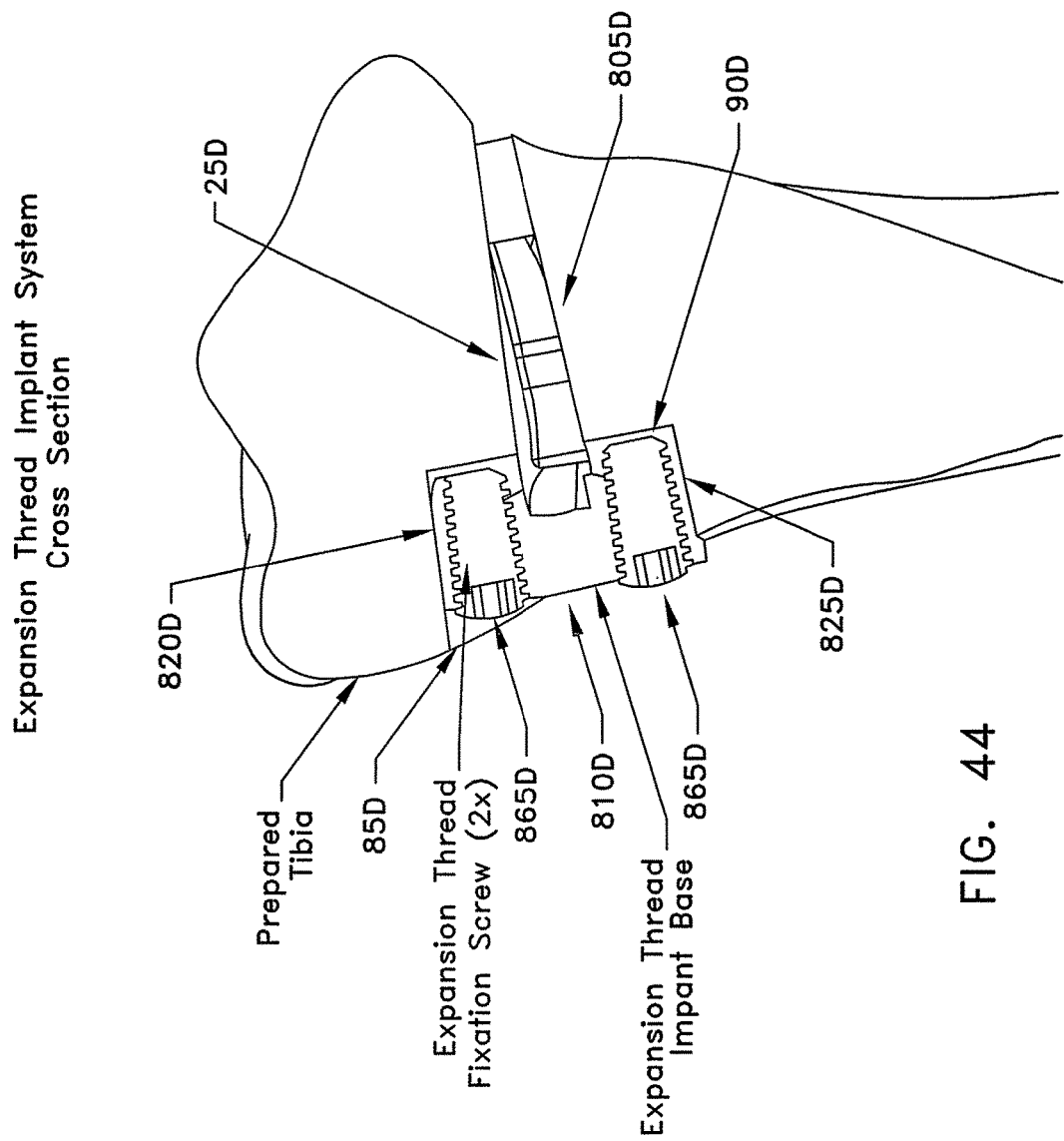

Looking next at FIGS. 42-44, there is shown an implant 800D also formed in accordance with the present invention. Implant 800D is generally similar to the implant 800C disclosed above, except that implant 800D is intended to be used with expansion thread fixation screws that terminate within the keys.

More particularly, and still looking now at FIGS. 42-44, implant 800D comprises a posterior graft containment arm (GCA) 805D, a base 810D and an anterior graft containment arm (GCA) 815D. Preferably a bridge 892D connects the distal end of posterior graft containment arm (GCA) 805D with the distal end of anterior graft containment arm (GCA) 815D. If desired, bridge 892D may be provided with a distal tab 898D to be received in oversized hole 95D. Distal tab 898D serves to improve the alignment and stability of implant 800D when seated in wedge-like opening 25D.

A shear rib 890D is formed in base 810D, laterally displaced from the two keys 820D, 825D (which are themselves arranged in an "over-under" configuration). Posterior graft containment arm (GCA) 805D includes a recess 893D, and base 810D includes a shoulder 894D, whereby posterior graft containment arm (GCA) 805D can mate with base 810D. Anterior graft containment arm (GCA) 815D includes a recess 895D, and implant base 810D includes a shoulder 896D, whereby anterior graft containment arm (GCA) 815D can mate with base 810D.

Posterior graft containment arm (GCA) 805D, and/or anterior graft containment arm (GCA) 815D, may include raised points or dimples 831D (not shown).

Keys 820D, 825D each include a bore 833D, 834D, respectively. Bores 833D, 834D receive expansion thread fixation screws 865D for fixing implant 800D to the tibia. Expansion thread fixation screws 865D are configured so as to intentionally terminate within bores 833D, 834D. This is in contrast to implant 800C which allows expansion thread fixation screws 865 to extend out of the distal ends of bores 833C, 834C and then into the adjacent bone. The bores 833D, 834D may be axially aligned with the longitudinal axes of keys 820D, 825D, respectively. Keys 820D, 825D may also include external ribs 836D (not shown). External ribs 836D may extend longitudinally or circumferentially. Keys 820D, 825D may also be slotted (i.e., in a manner analogous to the slots provided in keys 820, 825 of implant 800), whereby to permit keys 820D, 825D to expand when expansion thread fixation screws 865D are received in bores 833D, 834D. The external thread on the expansion thread fixation screws 865D may be tapered so as to expand the bore into the cancellous bone of the tibia when the expansion thread fixation screws are received within bores 833D, 834D. Alternatively, the internal thread on bores 833D, 834D may be tapered so as to expand the bore into the cancellous bone of the tibia when the expansion thread fixation screws 865D are received within bores 833D, 834D.

Shear rib 890D is laterally offset from keys 820D, 825D, which are arranged in an "over-under" configuration. Shear rib 890D projects above and below the top and bottom surfaces of base 810D. Among other things, it has been found that the provision of shear rib 890D provides, at the base of the implant, excellent load-bearing characteristics and substantial resistance to rotational and shear forces.

In order to provide appropriate keyholes 85D, 90D (FIG. 42) for receiving keys 820D, 825D, and also for providing a shear rib keyhole 897D for receiving shear rib 890D, a keyhole drill guide is used as disclosed above.

Implant 800D (and an associated drill guide) may be used in an open wedge, high tibial osteotomy in a manner which is generally similar to that previously described with respect to implant 800C (and drill guide 400C), except that expansion thread fixation screws 865D terminate within bores 833D, 834D.

Providing implant 800D with two graft containment arms, e.g., posterior graft containment arm (GCA) 805D and anterior graft containment arm (GCA) 815D, is frequently preferred. However, in some circumstances, it may be desirable to omit one or both of posterior graft containment arm (GCA) 805D and anterior graft containment arm (GCA) 815D. Thus, in one preferred form of the invention, implant 800D comprises only base 810D and omits both posterior graft containment arm (GCA) 805D and anterior graft containment arm (GCA) 815D.

Providing implant 800D with a pair of keys 820D, 825D is generally preferred. However, in some circumstances, it may be desirable to omit one or the other, or both, of keys 820D, 825D. Furthermore, in other circumstances, it may be desirable to provide more than two keys, e.g., to provide three keys.

Furthermore, each of the keys 820D, 825D may include more than one bore 833D, 834D. Thus, for example, one key may be expanded by multiple expansion thread fixation screws 865D.

It should be noted that while the construction of implant 800D is highly similar to the construction of implant 800C, the construction of implant 800D provides expansion thread fixation screws 865D that intentionally terminate within bores 833D, 834D, and hence within the body of the key, i.e., they do not penetrate into the adjacent bone.

Implant with Draw Nuts

Figure 45:
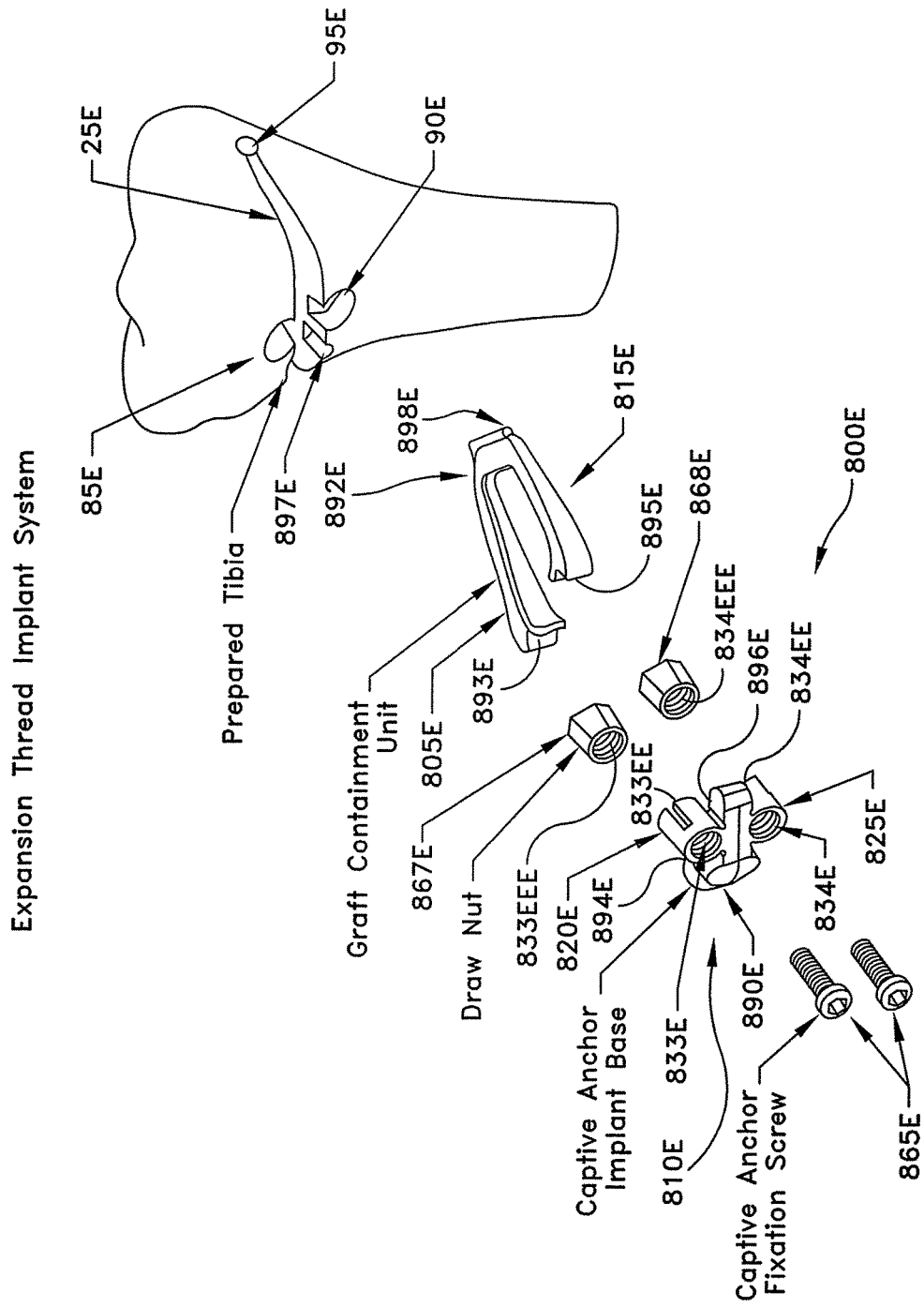
FIGS. 45-47 are schematic views showing another wedge-shaped implant formed in accordance with the present invention.
Figure 46:
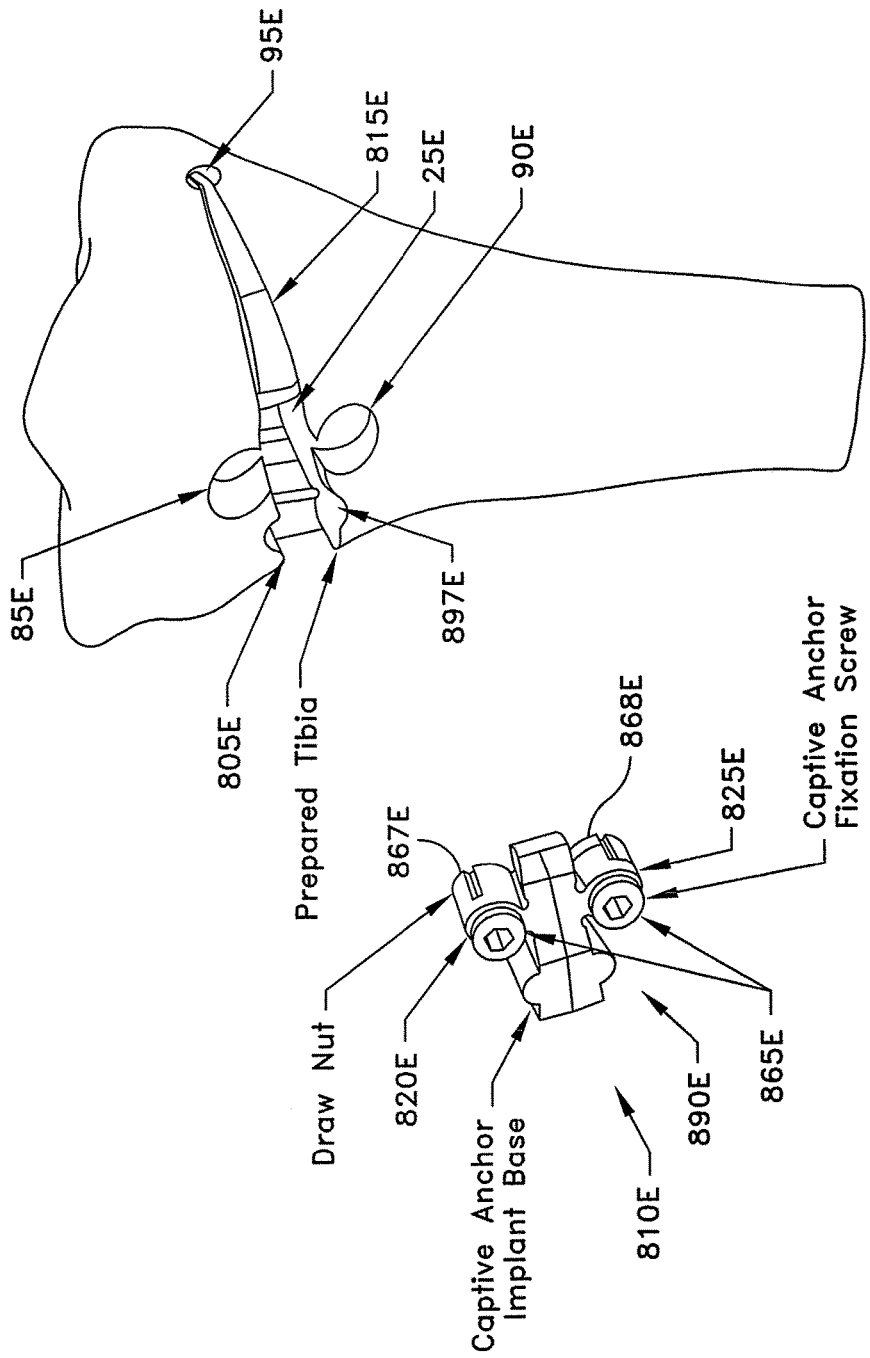
Figure 47:
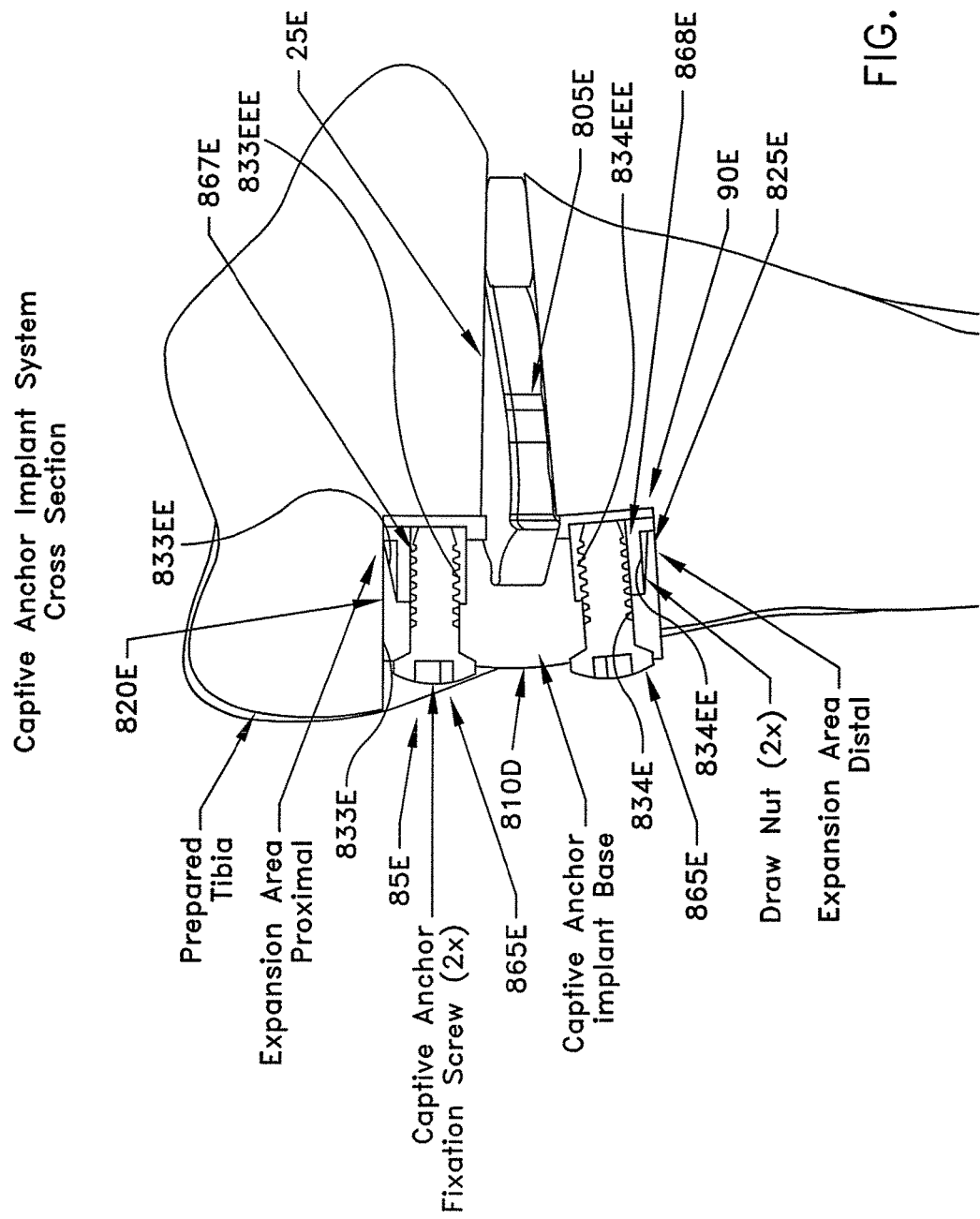

Looking next at FIGS. 45-47, there is shown an implant 800E also formed in accordance with the present invention. Implant 800E is generally similar to the implant 800C disclosed above, except that implant 800E provides counterbores 833EE, 834EE, respectively, for receiving draw nuts 867E, 868E, which in turn include bores 833EEE, 834EEE, respectively.

More particularly, and still looking now at FIGS. 45-47, implant 800E comprises a posterior graft containment arm (GCA) 805E, a base 810E and an anterior graft containment arm (GCA) 815E. Preferably a bridge 892E connects the distal end of posterior graft containment arm (GCA) 805E with the distal end of anterior graft containment arm (GCA) 815E. If desired, bridge 892E may be provided with a distal tab 898E to be received in oversized hole 95E. Distal tab 898E serves to improve the alignment and stability of implant 800E when seated in wedge-like opening 25E.

A shear rib 890E is formed in base 810E, laterally displaced from the two keys 820E, 825E (which are themselves arranged in an "over-under" configuration). Posterior graft containment arm (GCA) 805E includes a recess 893E, and base 810E includes a shoulder 894E, whereby posterior graft containment arm (GCA) 805E can mate with base 810E. Anterior graft containment arm (GCA) 815E includes a recess 895E, and implant base 810E includes a shoulder 896E, whereby anterior graft containment arm (GCA) 815E can mate with base 810E.

Posterior graft containment arm (GCA) 805E, and/or anterior graft containment arm (GCA) 815E, may include raised points or dimples 831E (not shown).

Keys 820E, 825E each include a bore 833E, 834E, respectively, and a counterbore 833EE, 834EE, respectively. Draw nuts 867E, 868E are positioned at the distal ends of bores 833E, 834E, in counterbores 833EE, 834EE, respectively. Draw nuts 867E, 868E each include a bore 833EEE, 834EEE, respectively, such that when expansion thread fixation screws 865E are received in bores 833E, 834E and bores 833EEE, 834EEE of draw nuts 867E, 868E, the draw nuts will be drawn into counterbores 833EE, 834EE, thereby enhancing the expansion of keys 820E, 825E, whereby to securely fix implant 800E to the tibia.

The bores 833E, 834E may be axially aligned with the longitudinal axes of keys 820E, 825E, respectively. Keys 820E, 825E may also include external ribs 836E (not shown). External ribs 836E may extend longitudinally or circumferentially. Keys 820E, 825E may also be slotted (i.e., in a manner analogous to the slots provided in keys 820, 825 of implant 800), whereby to permit keys 820E, 825E to expand when expansion thread fixation screws 865E are received in bores 833E, 834E and in bores 833EEE, 834EEE of draw nuts 867E, 868E.

Shear rib 890E is laterally offset from keys 820E, 825E, which are arranged in an "over-under" configuration. Shear rib 890E projects above and below the top and bottom surfaces of base 810E. Among other things, it has been found that the provision of shear rib 890E provides, at the base of the implant, excellent load-bearing characteristics and substantial resistance to rotational and shear forces.

In order to provide appropriate keyholes 85E, 90E (FIGS. 45 and 46) for receiving keys 820E, 825E, and also for providing a shear rib keyhole 897E for receiving shear rib 890E, a keyhole drill guide is used as disclosed above.

Implant 800E (and an associated drill guide) may be used in an open wedge, high tibial osteotomy in a manner which is generally similar to that previously described with respect to implant 800C (and drill guide 400C). Providing implant 800E with two graft containment arms, e.g., posterior graft containment arm (GCA) 805E and anterior graft containment arm (GCA) 815E, is frequently preferred. However, in some circumstances, it may be desirable to omit one or both of posterior graft containment arm (GCA) 805E and anterior graft containment arm (GCA) 815E. Thus, in one preferred form of the invention, implant 800E comprises only base 810E and omits both posterior graft containment arm (GCA) 805E and anterior graft containment arm (GCA) 815E.

Providing implant 800E with a pair of keys 820E, 825E is generally preferred. However, in some circumstances, it may be desirable to omit one or the other, or both, of keys 820E, 825E. Furthermore, in other circumstances, it may be desirable to provide more than two keys, e.g., to provide three keys.

Furthermore, each of the keys 820E, 825E may include more than one bore 833E, 834E and counterbore 833EE, 834EE and more than one draw nut 867E, 868E. Thus, for example, one key may be expanded by multiple expansion thread fixation screws 865E.

It should be noted that while the construction of implant 800E is highly similar to the construction of implant 800C, the construction of implant 800E provides draw nuts 867E, 868E positioned at the distal ends of bores 833E, 834E, received within counterbores 833EE, 834EE, respectively.

Implant with Open Keys

Figure 48:
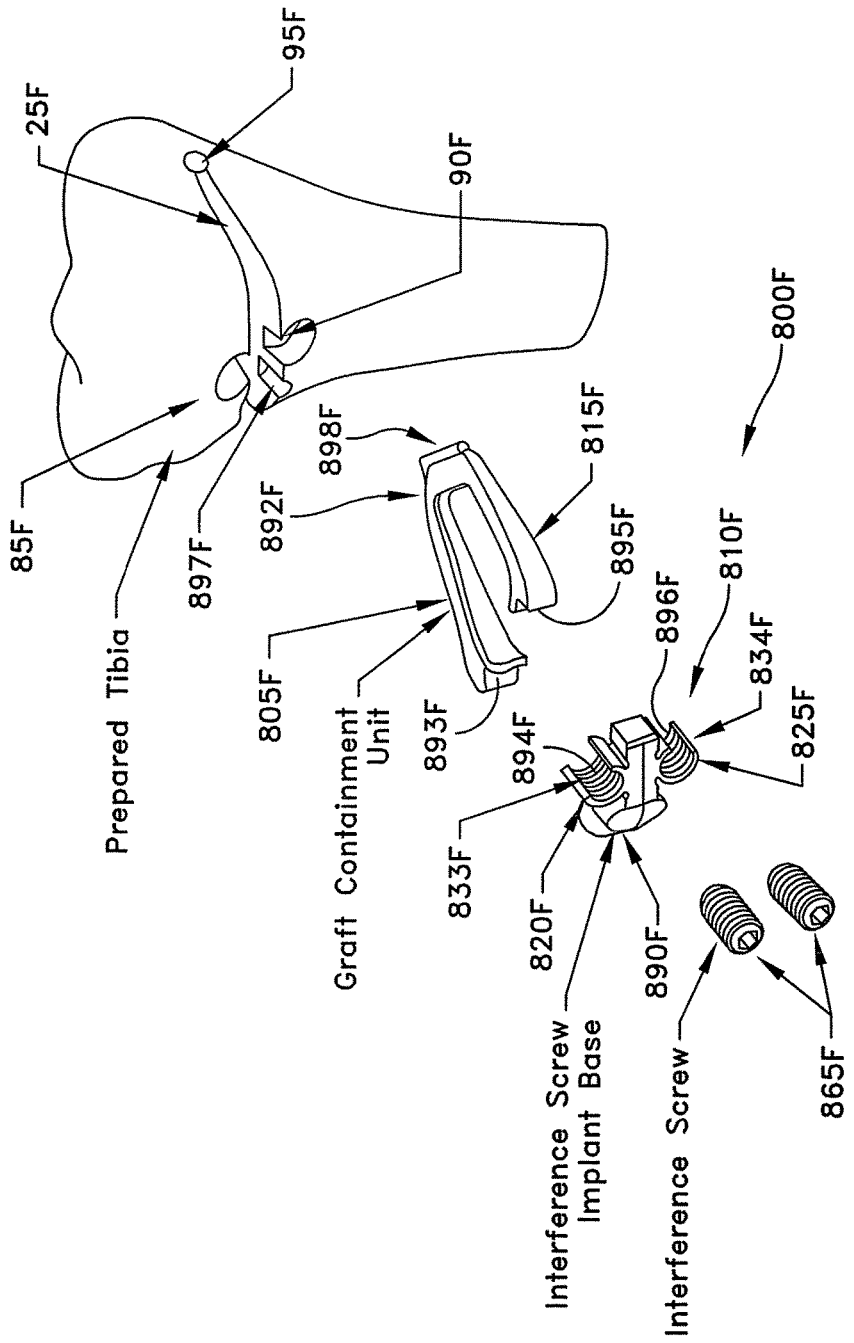
FIGS. 48-50 are schematic views showing still another wedge-shaped implant formed in accordance with the present invention.
Figure 49:
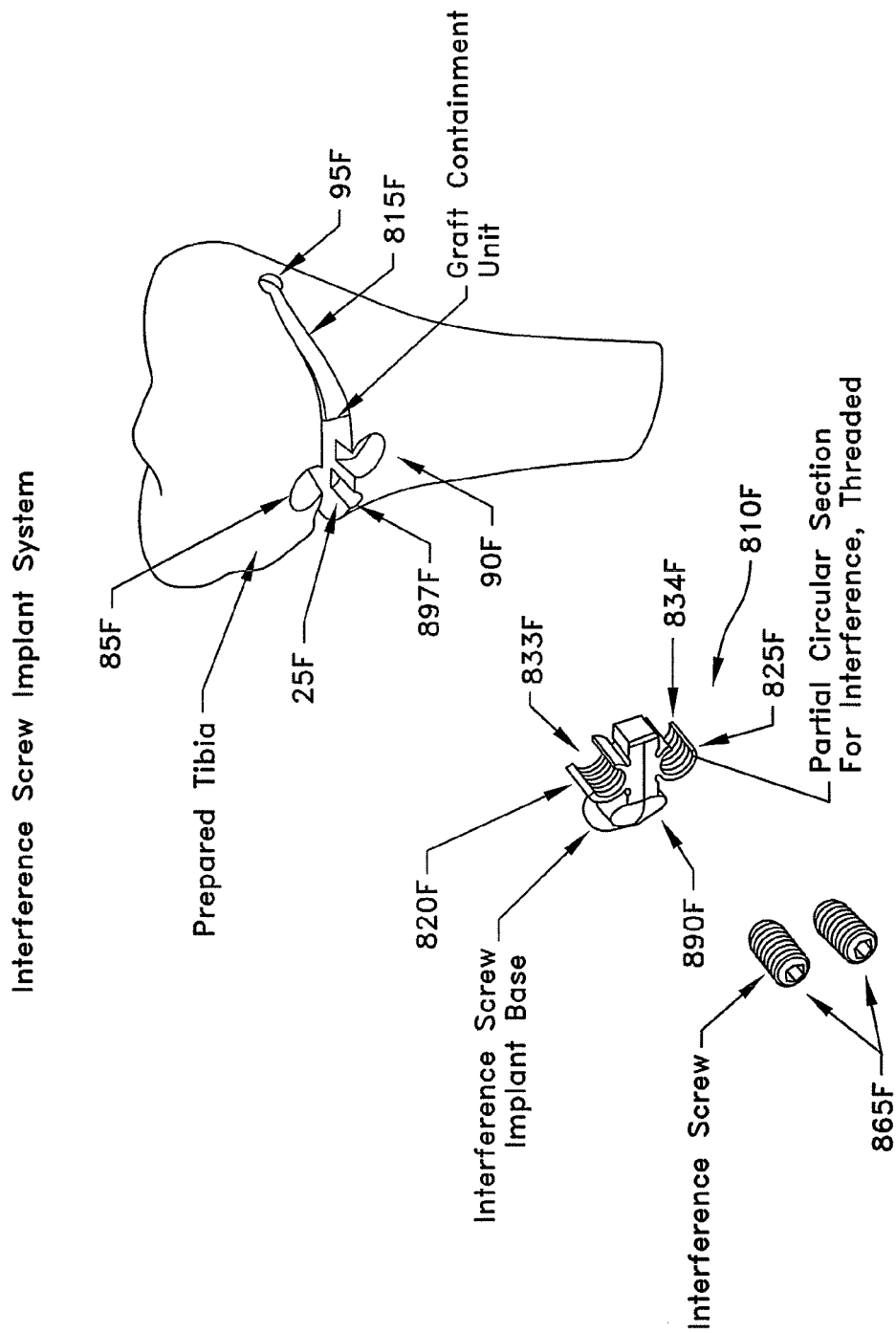
Figure 50:
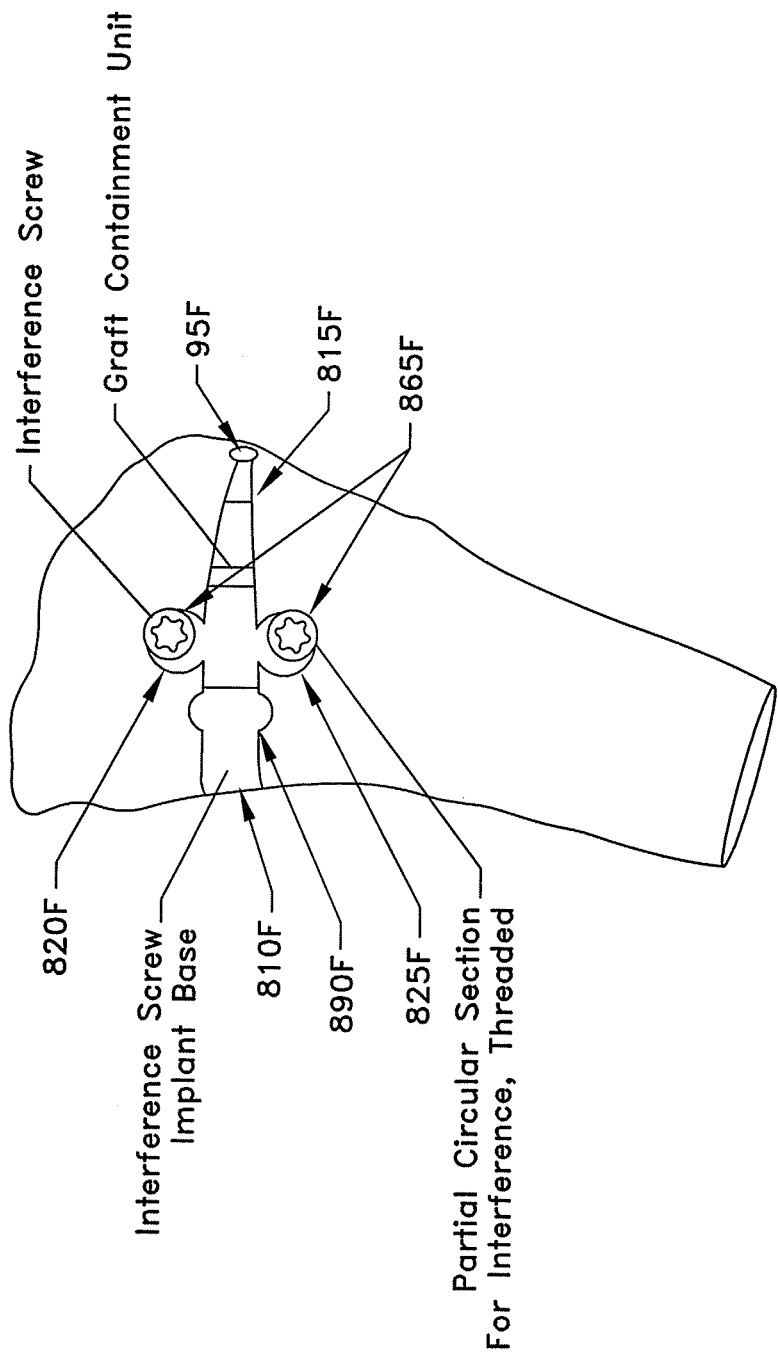
Figure 51:
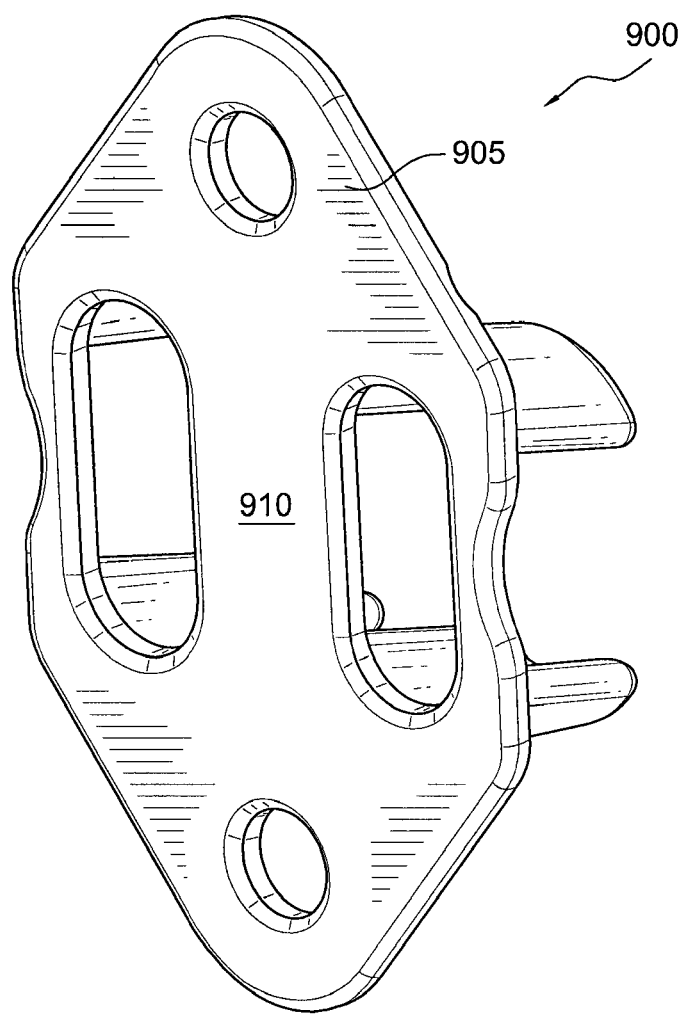
FIGS. 51-55 are schematic views showing a novel osteotomy plate formed in accordance with the present invention.

Looking next at FIGS. 48-50, there is shown an implant 800F also formed in accordance with the present invention. Implant 800F is generally similar to the implant 800C disclosed above, except that implant 800F provides open keys having opposed longitudinal edges. Furthermore, the open keys include threaded recesses.

More particularly, and still looking now at FIGS. 48-50, implant 800F comprises a posterior graft containment arm (GCA) 805F, a base 810F and an anterior graft containment arm (GCA) 815F. Preferably a bridge 892F connects the distal end of posterior graft containment arm (GCA) 805F with the distal end of anterior graft containment arm (GCA) 815F. If desired, bridge 892F may be provided with a distal tab 898F to be received in oversized hole 95F. Distal tab 898F serves to improve the alignment and stability of implant 800F when seated in wedge-like opening 25F.

A shear rib 890F is formed in base 810F, laterally displaced from two open keys 820F, 825F (which are themselves arranged in an "over-under" configuration). Posterior graft containment arm (GCA) 805F includes a recess 893F, and base 810F includes a shoulder 894F, whereby posterior graft containment arm (GCA) 805F can mate with base 810F. Anterior graft containment arm (GCA) 815F includes a recess 895F, and implant base 810F includes a shoulder 896F, whereby anterior graft containment arm (GCA) 815F can mate with base 810F.

Posterior graft containment arm (GCA) 805F, and/or anterior graft containment arm (GCA) 815F, may include raised points or dimples 831F (not shown).

Open keys 820F, 825F each include a threaded recess 833F, 834F, respectively. It should be appreciated that due to the geometry of the open keys 820F, 825F when expansion thread fixation screws 865F are received in the threaded recesses 833F, 834F, a portion of the threaded surface of expansion thread fixation screws 865F are exposed to, and hence directly engage, the adjacent bone. This is in contrast with implant 800C, wherein the fixation screws 865C are received within closed keys 820C, 825C.

In one form of the present invention, the keyholes 85F, 90F may be further prepared by tapping with a tap 899F (not shown) with a corresponding thread pitch to that of expansion thread fixation screws 865F.

Threaded recesses 833F, 834F may be axially aligned with the longitudinal axes of open keys 820F, 825F, respectively. Open keys 820F, 825F may also include external ribs 836F. External ribs 836F may extend longitudinally or circumferentially. Open keys 820F, 825F may also be only partially opened, i.e., along only a portion of the length of the keys (i.e., in a manner analogous to the slots provided in keys 820, 825 of implant 800), whereby to provide open keys 820F, 825F with greater structural integrity.

Shear rib 890F is laterally offset from open keys 820F, 825F, which are arranged in an "over-under" configuration. Shear rib 890F projects above and below the top and bottom surfaces of base 810F. Among other things, it has been found that the provision of shear rib 890F provides, at the base of the implant, excellent load-bearing characteristics and substantial resistance to rotational and shear forces.

In order to provide appropriate keyholes 85F, 90F (FIG. 48) for receiving open keys 820F, 825F, and also for providing a shear rib keyhole 897F for receiving shear rib 890F, a keyhole drill guide is used as disclosed above.

Implant 800F (and the associated drill guide) may be used in an open wedge, high tibial osteotomy in a manner which is generally similar to that previously described with respect to implant 800C (and drill guide 400C), except that the bridged graft containment unit, i.e., posterior graft containment arm (GCA) 805F, bridge 892F and anterior graft containment arm (GCA) 815F, is installed as a single construction.

Furthermore, when drill guide 400F is used to form keyholes 85F and 90F, it is also used to form shear rib keyhole 897F.

Providing implant 800F with two graft containment arms, e.g., posterior graft containment arm (GCA) 805F and anterior graft containment arm (GCA) 815F, is frequently preferred. However, in some circumstances, it may be desirable to omit one or both of posterior graft containment arm (GCA) 805F and anterior graft containment arm (GCA) 815F. Thus, in one preferred form of the invention, implant 800F comprises only base 810F and omits both posterior graft containment arm (GCA) 805F and anterior graft containment arm (GCA) 815F.

Providing implant 800F with a pair of open keys 820F, 825F is generally preferred. However, in some circumstances, it may be desirable to omit one or the other, or both, of open keys 820F, 825F. Furthermore, in other circumstances, it may be desirable to provide more than two open keys, e.g., to provide three open keys.

Furthermore, each of the open keys 820F, 825F may include more than one threaded recess 833F, 834F. Thus, for example, open keys may contain multiple, but not overlapping, recesses to receive multiple expansion thread fixation screws 865F. Thus, for example, an open key may include two recesses, one angled leftwardly so as to direct a fixation screw leftwardly into the tibia to the left of the open key, and/or one angled rightwardly so as to direct a fixation screw rightwardly into the tibia to the right of the open key.

It should be noted that while the construction of implant 800F is highly similar to the construction of implant 800C, the construction of implant 800F provides keys which allow a portion of the threaded surface of expansion thread fixation screws 865F to directly engage the adjacent bone.

Osteotomy Plate with Two Keys

It is also possible to replace the aforementioned wedge-shaped implants 27, 800, 800A, 800B, 800C, 800D, 800E and 800F with a novel osteotomy plate comprising two keys.

More particularly, and looking now at FIGS. 51-55, there is shown a novel osteotomy plate 900 also formed in accordance with the present invention. Osteotomy plate 900 is also designed to maintain the spacing of wedge-like opening 25 (FIGS. 2 and 23) formed in tibia 10. Preferably, wedge-like opening 25 is formed using the aforementioned novel apex pin technology of the present invention. However, it is also possible to use osteotomy plate 900 when the wedge-like opening 25 is formed in other ways well known in the art. In any case, however, wedge-like opening 25 is provided with keyholes 85, 90 (FIGS. 53 and 54) in order to cooperate with corresponding members provided on osteotomy plate 900, as will hereinafter be discussed in further detail.

Figure 52:
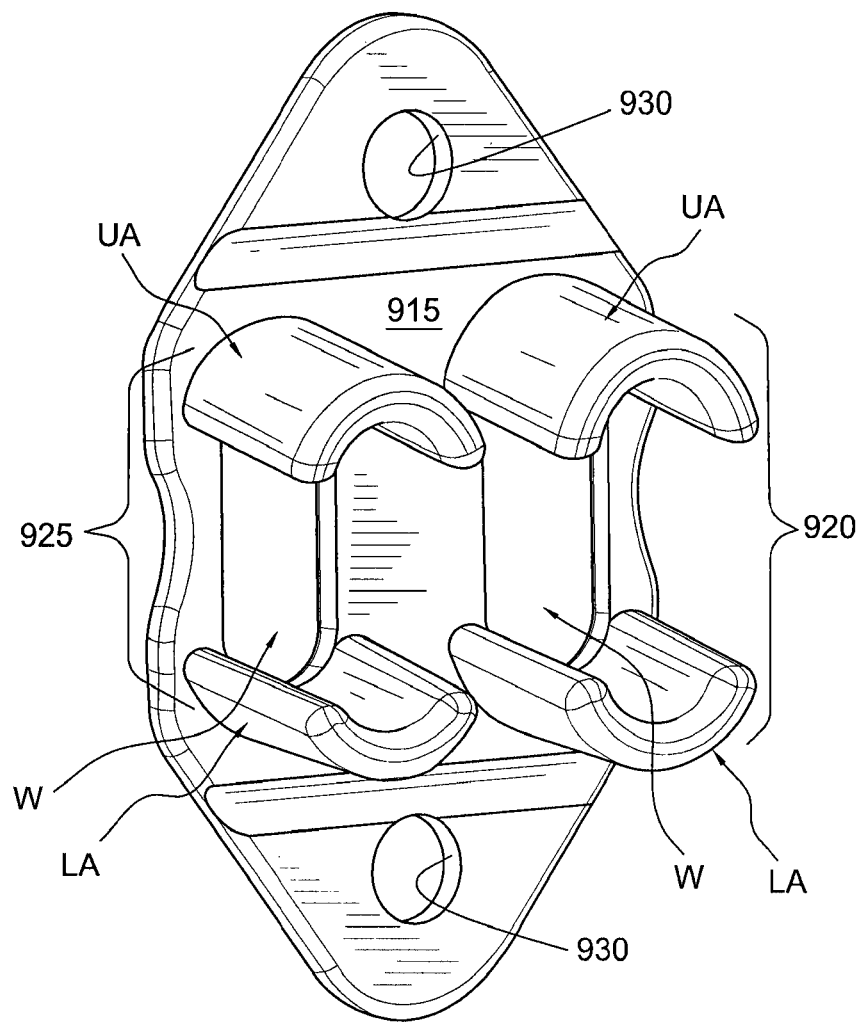

Osteotomy plate 900 generally comprises a body 905 having a front side 910 and a back side 915. A pair of keys 920, 925 (FIG. 52) project out of back side 915 of osteotomy plate 900. Each of the keys 920, 925 comprises an upper arc UA and a lower arc LA. Upper arc UA of key 920 may be spaced from its corresponding lower arc LA of key 920 (e.g., as shown in FIG. 52), or upper arc UA of key 920 may be connected to its corresponding lower arc LA of key 920 by a pair of walls (not shown). Similarly, upper arc UA of key 925 may be spaced from its corresponding lower arc LA of key 925 (e.g., as shown in FIG. 52), or upper arc UA of key 925 may be connected to its corresponding lower arc LA of key 925 by a pair of walls (not shown). Preferably, each of the keys 920, 925 has a corresponding window W formed in body 905 of osteotomy plate 900, with window W communicating with the interior of the key between upper arc UA and lower arc LA of that key. In addition to the foregoing, osteotomy plate 900 also includes a pair of mounting holes 930 extending between the osteotomy plate's front side 910 and back side 915.

Figure 53:
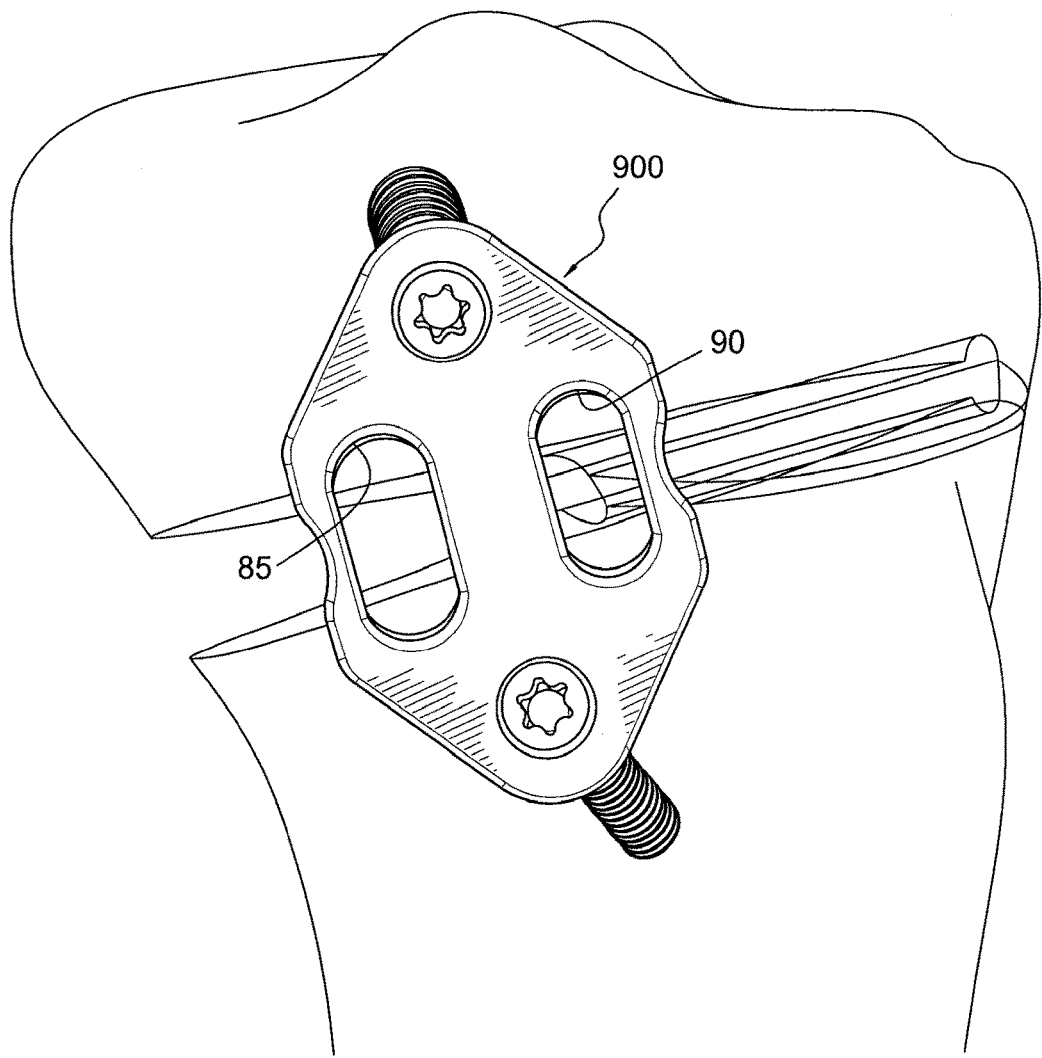
Figure 54:
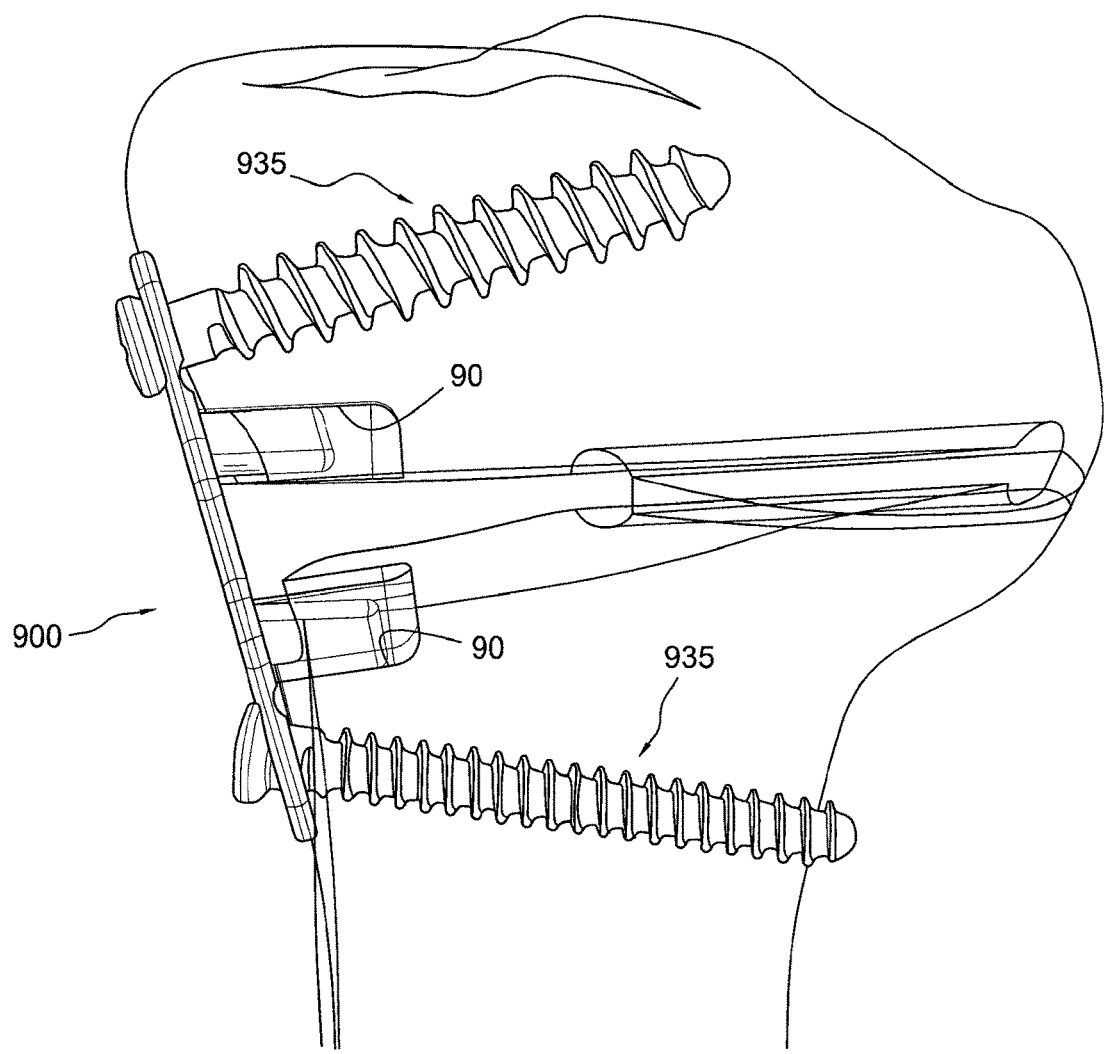
Figure 55:
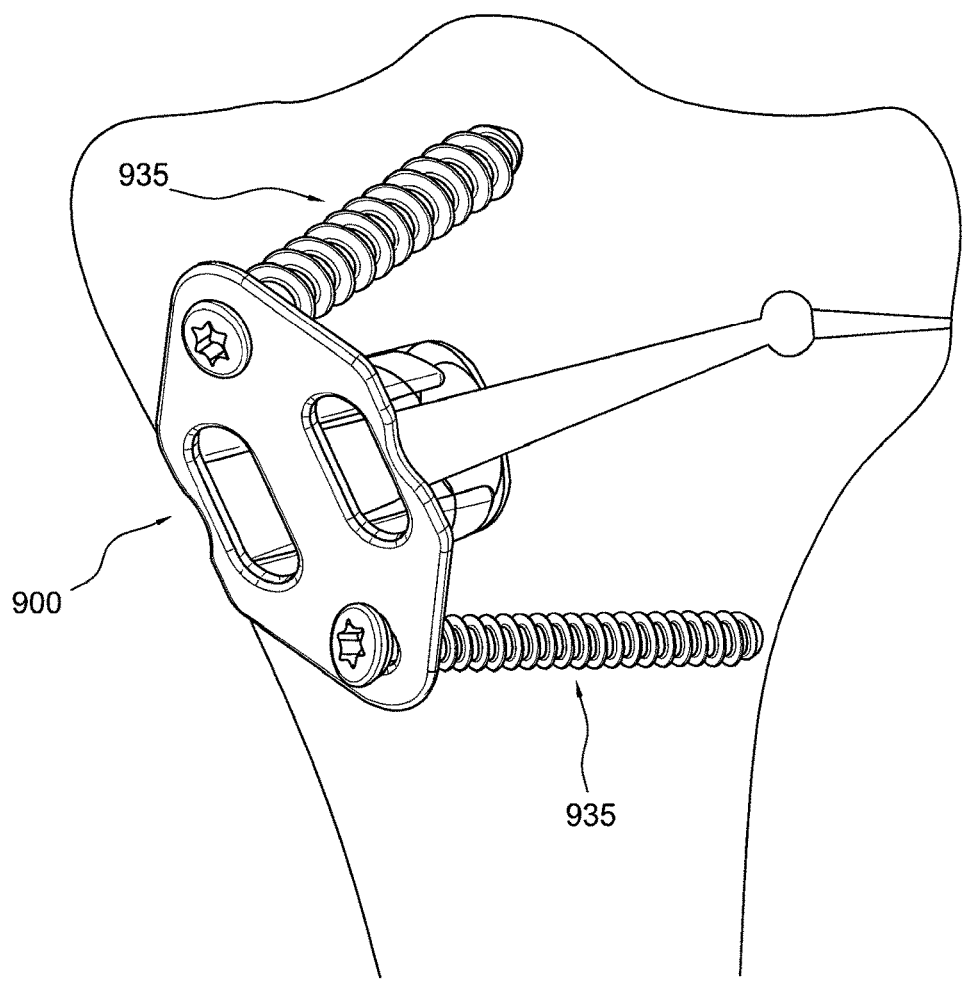

In use, and looking now at FIGS. 53-55, once the tibia has been prepared (i.e., by forming the keyholes 85, 90 in the tibia, forming the osteotomy cut 20 in the tibia, and opening the tibia so as to form the wedge-like opening 25), osteotomy plate 900 is positioned against tibia 10 so that (i) keys 920, 925 of the osteotomy plate are disposed in keyholes 85, 90 of tibia 10, and (ii) the back side 915 of osteotomy plate is positioned against the face of the tibia. Then, fixation screws 935 are passed through the osteotomy plate's mounting holes 930 and into the tibia, so as to secure the osteotomy plate to the tibia. At this point, the upper arcs UA of keys 920, 925, and the lower arcs LA of keys 920, 925, engage the upper and lower portions of the tibia, respectively, whereby to maintain the desired configuration of the tibia.

If desired, windows W may be used to insert bone graft material, cement, etc., into the interior of wedge-like opening 25. In addition, windows W may be used to pass surgical instruments into the interior of wedge-like opening 25.

Osteotomy Plate with Two Keys and a Pair of Bosses

Figure 56:
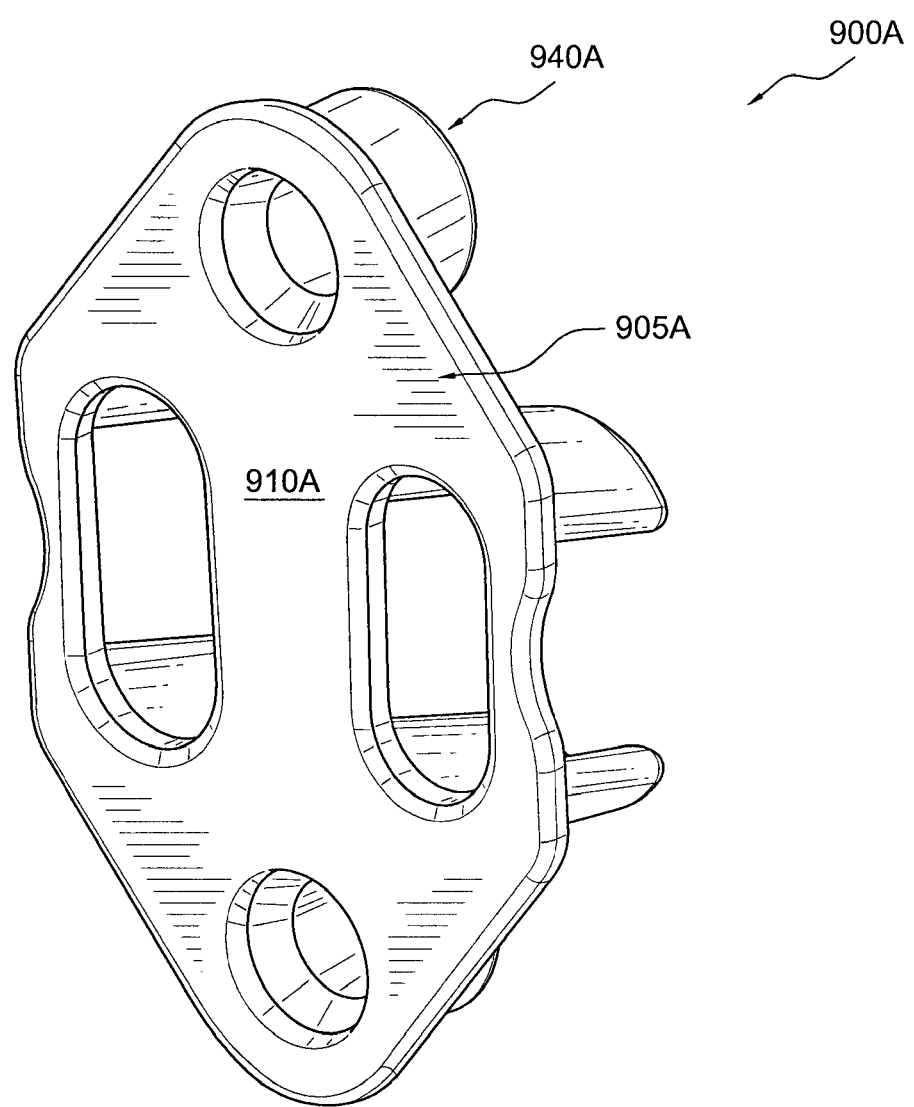
FIGS. 56-58 are schematic views showing another novel osteotomy plate formed in accordance with the present invention.
Figure 57:
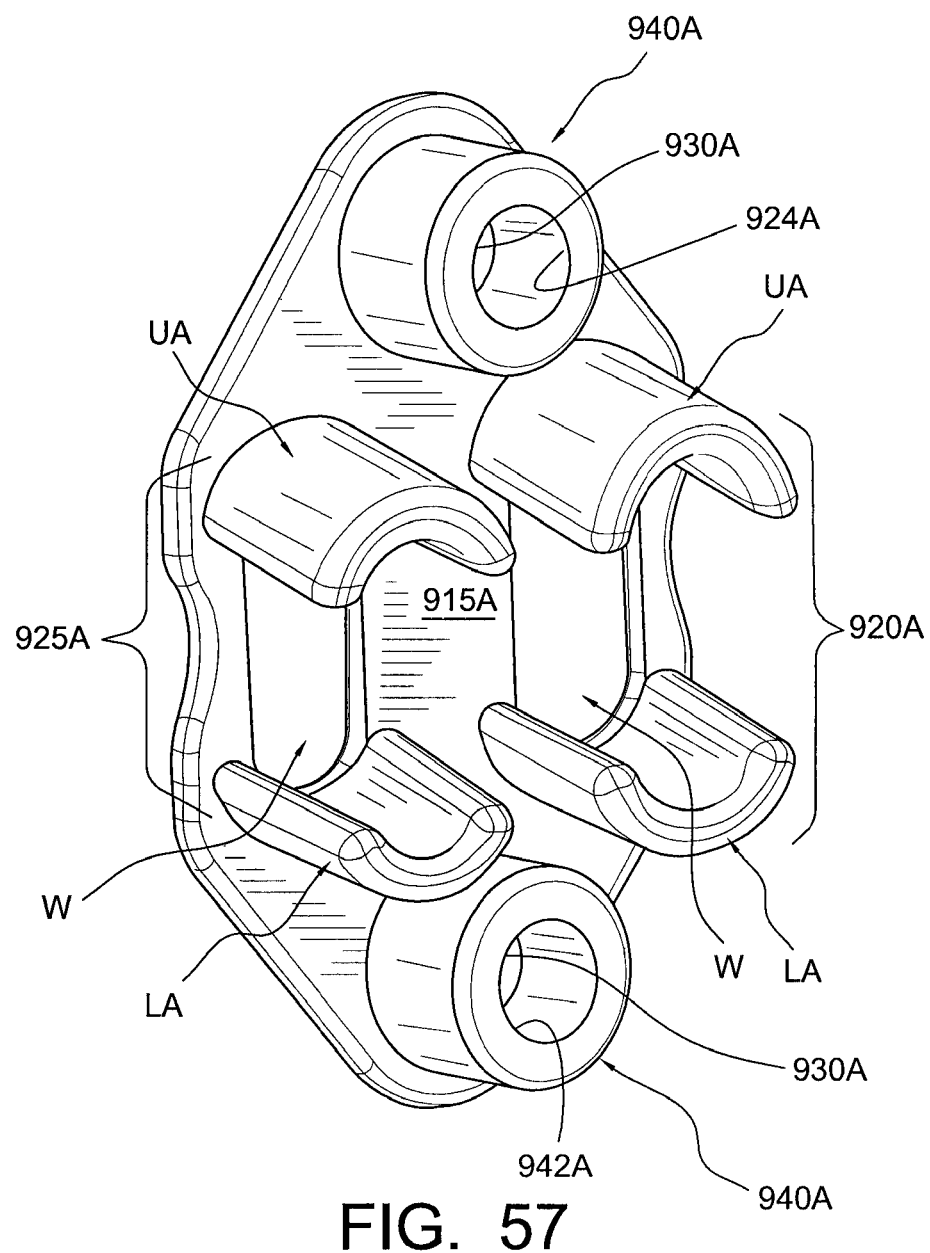
Figure 58:
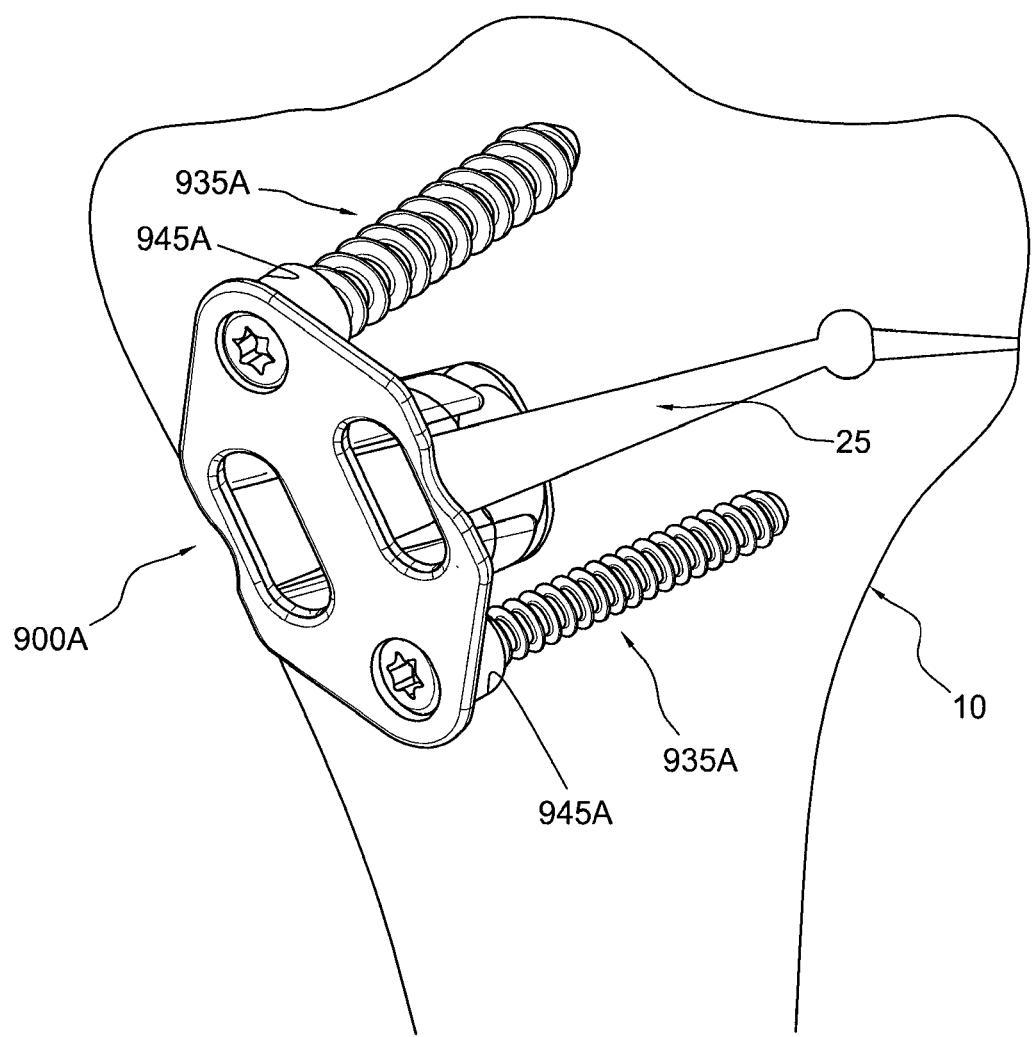

Looking next at FIGS. 56-58, there is shown another osteotomy plate 900A also formed in accordance with the present invention. Osteotomy plate 900A is substantially identical to the osteotomy plate 900 discussed above, except that osteotomy plate 900A includes a pair of bosses 940A, wherein each boss projects out of back side 915A of osteotomy plate 900A (FIG. 57). Preferably, but not necessarily, each boss 940A is aligned with a mounting hole 930A and includes a bore 942A which is co-axial with mounting hole 930A.

In use, and looking now at FIG. 58, the tibia is prepared in the usual fashion (i.e., by forming the keyholes 85, 90 in the tibia, forming the osteotomy cut 20 in the tibia, and opening the tibia so as to form the wedge-like opening 25), except that boss holes 945A are formed in the tibia as well. Preferably boss holes 945A are formed at substantially the same time as the keyholes 85, 90, although they may also be formed before or after keyholes 85, 90. After tibia 10 has been prepared, an appropriately-sized osteotomy plate 900A is positioned against tibia 10 so that (i) keys 920A, 925A are disposed in keyholes 85, 90 of tibia 10, (ii) bosses 940A are disposed in boss holes 945A of tibia 10, and (iii) the back side 915A of osteotomy plate 900A is positioned against the face of the tibia. Then fixation screws 935A are passed through the osteotomy plate's mounting holes 930A, boss bores 942A and into the tibia, so as to secure the osteotomy plate to the tibia. At this point, the upper arcs UA of keys 920A, 925A, and the lower arcs LA of keys 920A, 925A, engage the upper and lower portions of the tibia, respectively, whereby to maintain the desired configuration of the tibia.

It will be appreciated that the provision of bosses 940A provides additional stability to the osteotomy plate 900A, since the bosses 940A are disposed in the boss holes 945A in the tibia, thereby providing resistance to any undesired migration of the osteotomy plate vis-a-vis the tibia.

Again, windows W may be used to insert bone graft material, cement, etc., into the interior of wedge-like opening 25. In addition, windows W may be used to pass surgical instruments into the interior of wedge-like opening 25.

Osteotomy Plate with Two Keys and Two Pairs of Bosses

Figure 59:
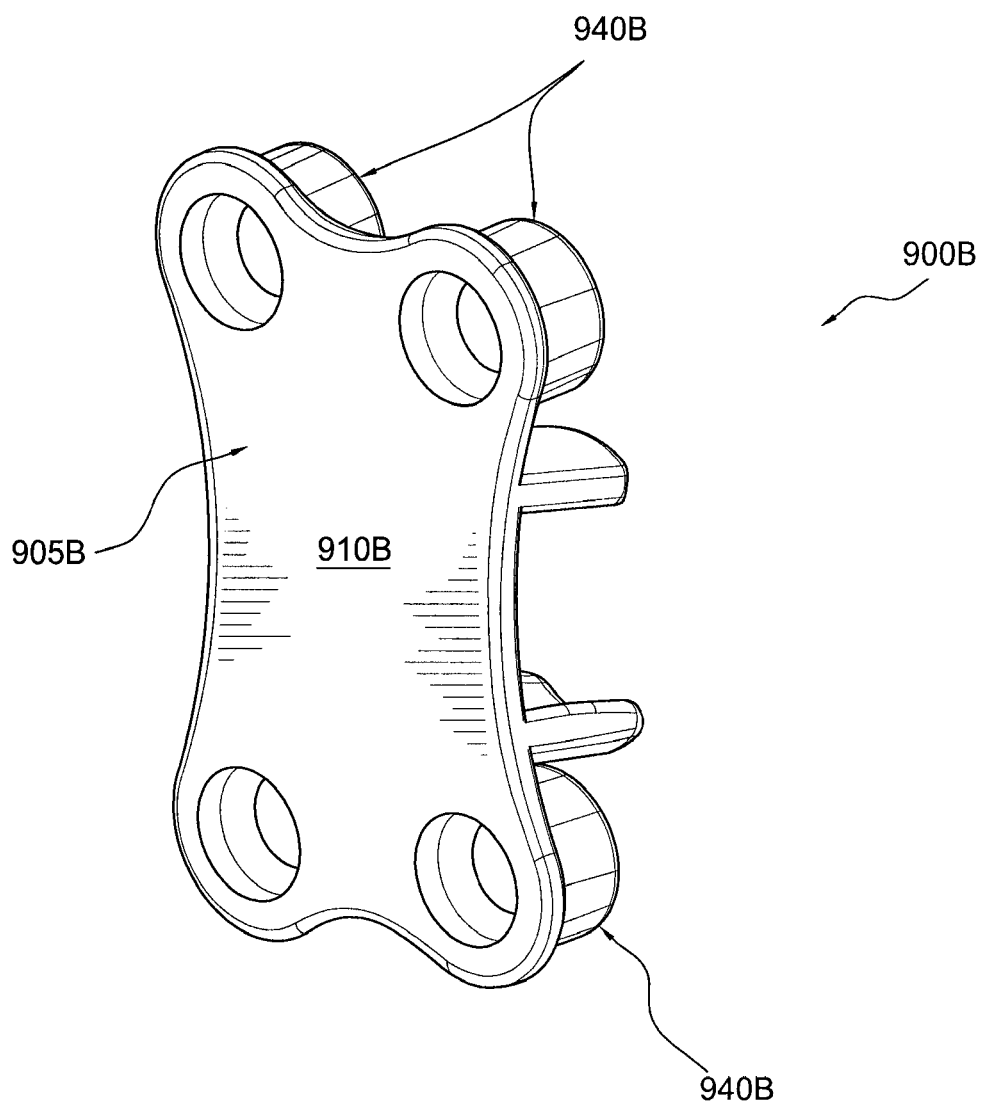
FIGS. 59-61 are schematic views showing still another novel osteotomy plate formed in accordance with the present invention.
Figure 60:
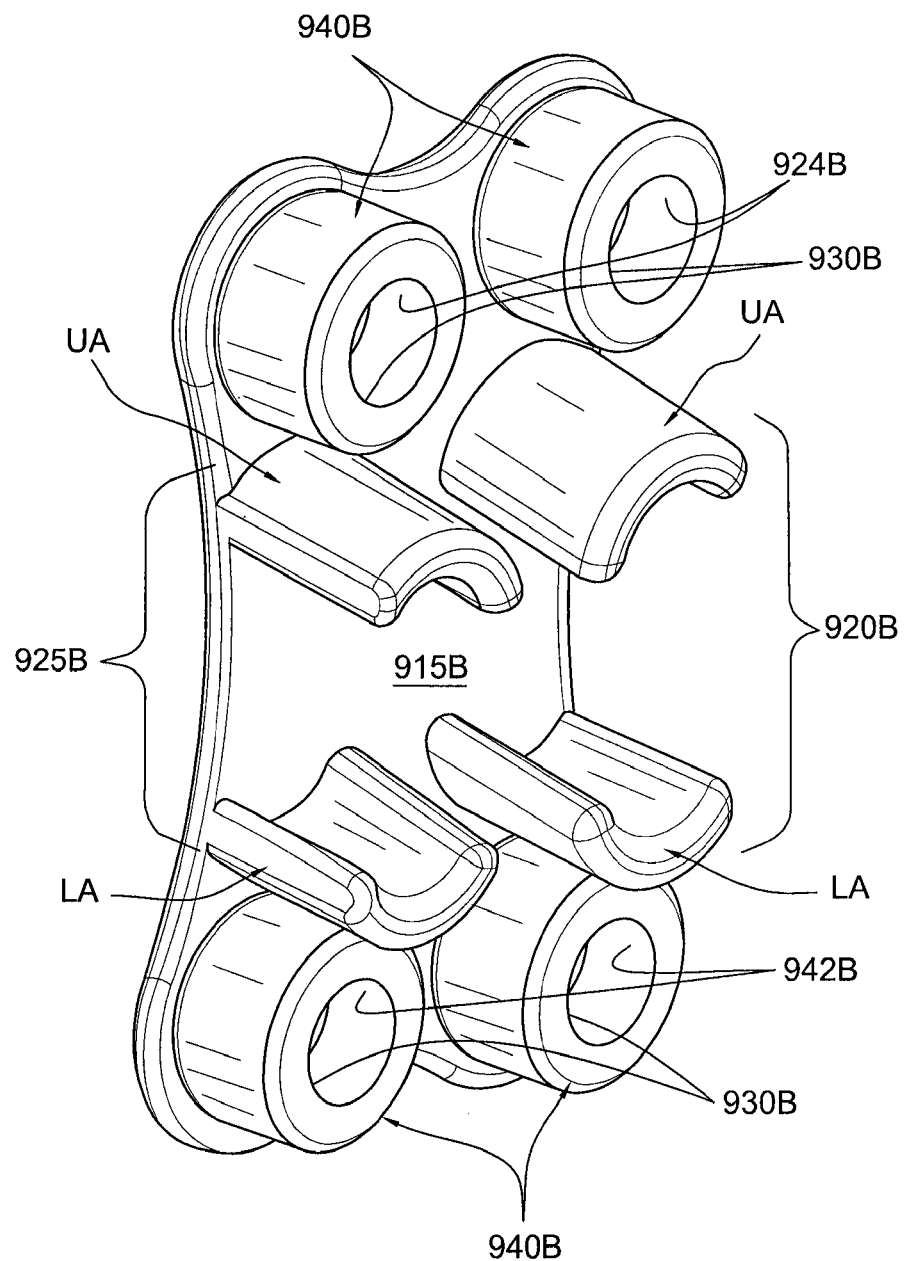
Figure 61:
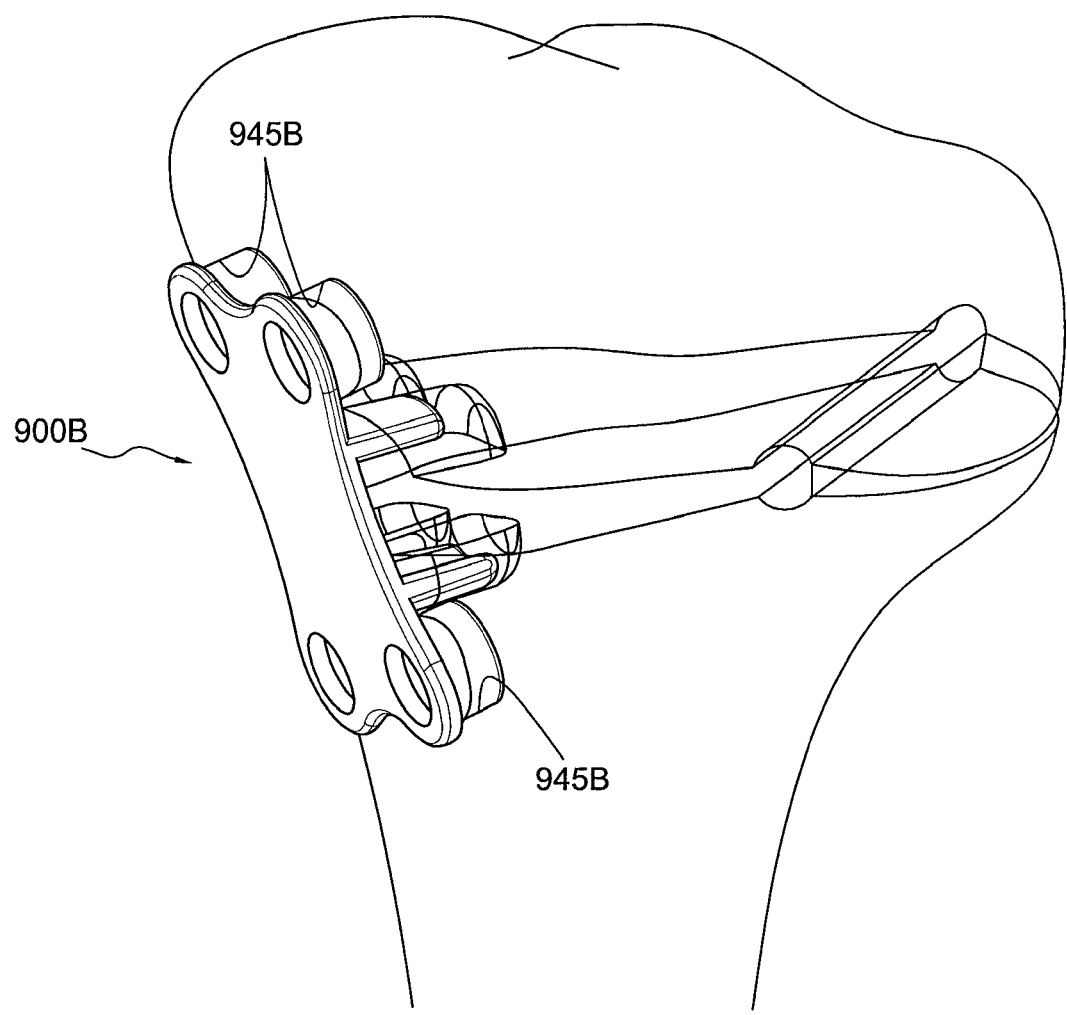

Looking next at FIGS. 59-61, there is shown an osteotomy plate 900B which is substantially identical to the osteotomy plate 900A discussed above, except that osteotomy plate 900B includes two pairs of bosses 940B, wherein each boss projects out of back side 915B of osteotomy plate 900B (FIG. 60). Preferably, but not necessarily, each boss 940B is aligned with a mounting hole 930B and includes a bore 942B which is co-axial with mounting hole 930B. Osteotomy plate 900B also omits the provisions of windows W.

In use, and looking now at FIG. 61, the tibia is prepared in the usual fashion (i.e., by forming the keyholes 85, 90 in the tibia, forming the osteotomy cut 20 in the tibia, and opening the tibia so as to form the wedge-like opening 25), except that boss holes 945B are formed in the tibia as well. Preferably boss holes 945B are formed at substantially the same time as the keyholes 85, 90, although they may also be formed before or after keyholes 85, 90. After tibia 10 has been prepared, an appropriately-sized osteotomy plate 900B is positioned against tibia 10 so that (i) keys 920B, 925B are disposed in keyholes 85, 90 of tibia 10, (ii) bosses 940B are disposed in boss holes 945B of tibia 10, and (iii) the back side 915B of osteotomy plate 900B is positioned against the face of the tibia. Then fixation screws (not shown) are passed through the osteotomy plate's mounting holes 930B, boss bores 942B and into the tibia, so as to secure the osteotomy plate to the tibia. At this point, the upper arcs UA of keys 920B, 925B, and the lower arcs LA of keys 920B, 925B, engage the upper and lower portions of the tibia, respectively, whereby to maintain the desired configuration of the tibia.

It will be appreciated that the provision of bosses 940B provide additional stability to the osteotomy plate 900B, since the bosses 940B are disposed in the boss holes 945B in the tibia, thereby providing resistance to any undesired migration of the osteotomy plate vis-a-vis the tibia.

It will also be appreciated that the omission of windows W from osteotomy plate 900B may enhance the torsional strength of osteotomy plate 900B. To the extent that it is desired to insert bone graft material, cement, etc. into the interior of the wedge-like opening 25, this may be done before osteotomy plate 900B is placed in position.

Osteotomy Plate with Two Pair of Back Side Bosses

Figure 62:
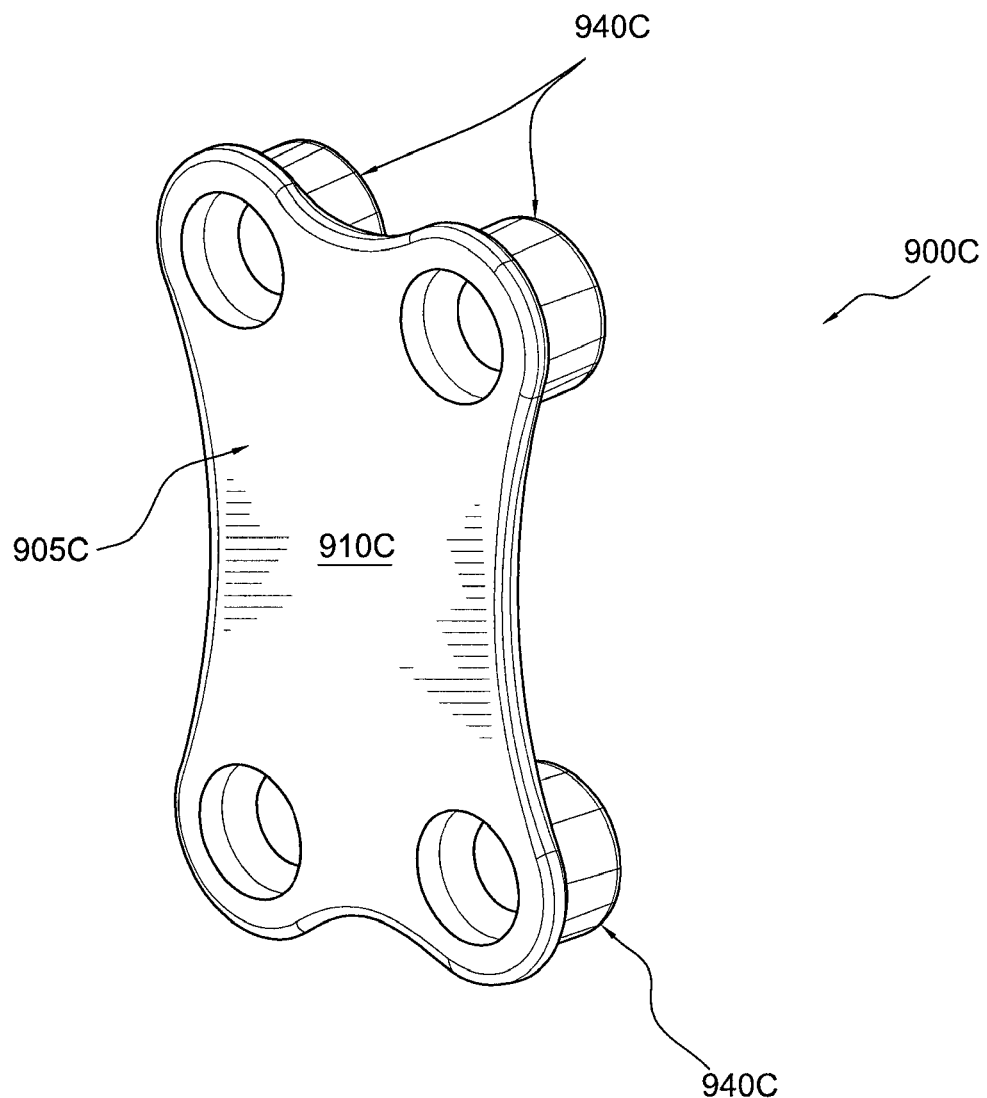
FIGS. 62-64 are schematic views showing still another novel osteotomy plate formed in accordance with the present invention.
Figure 63:
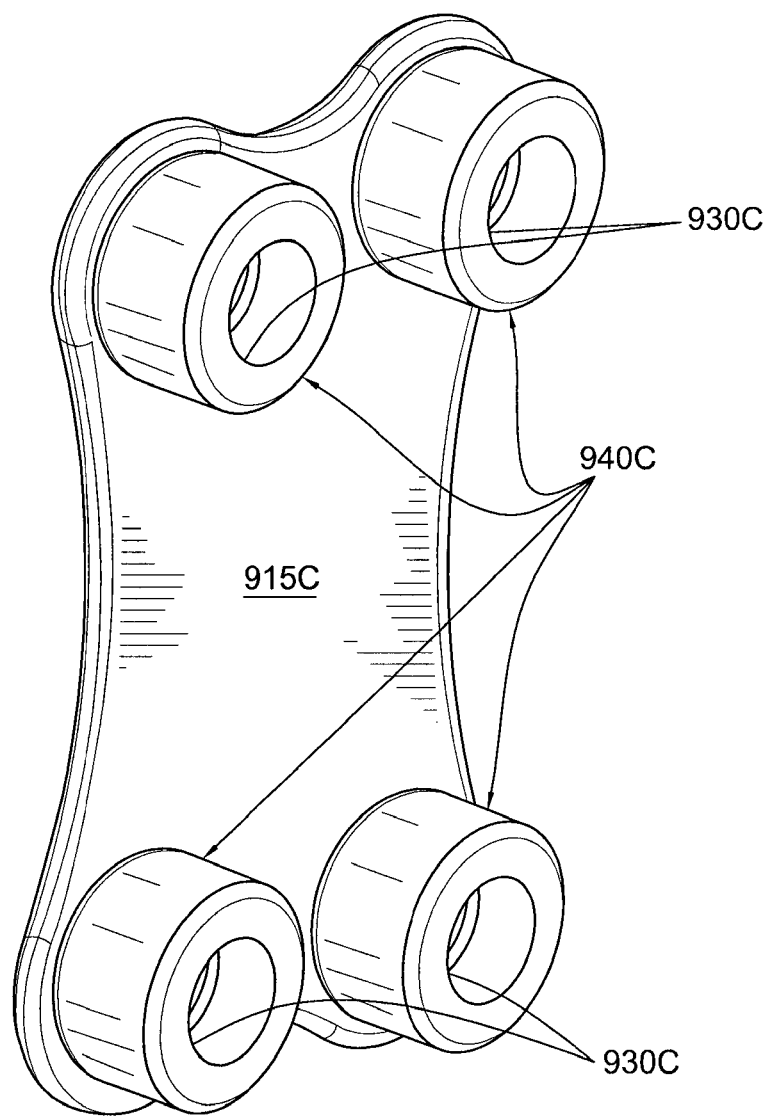
Figure 64:
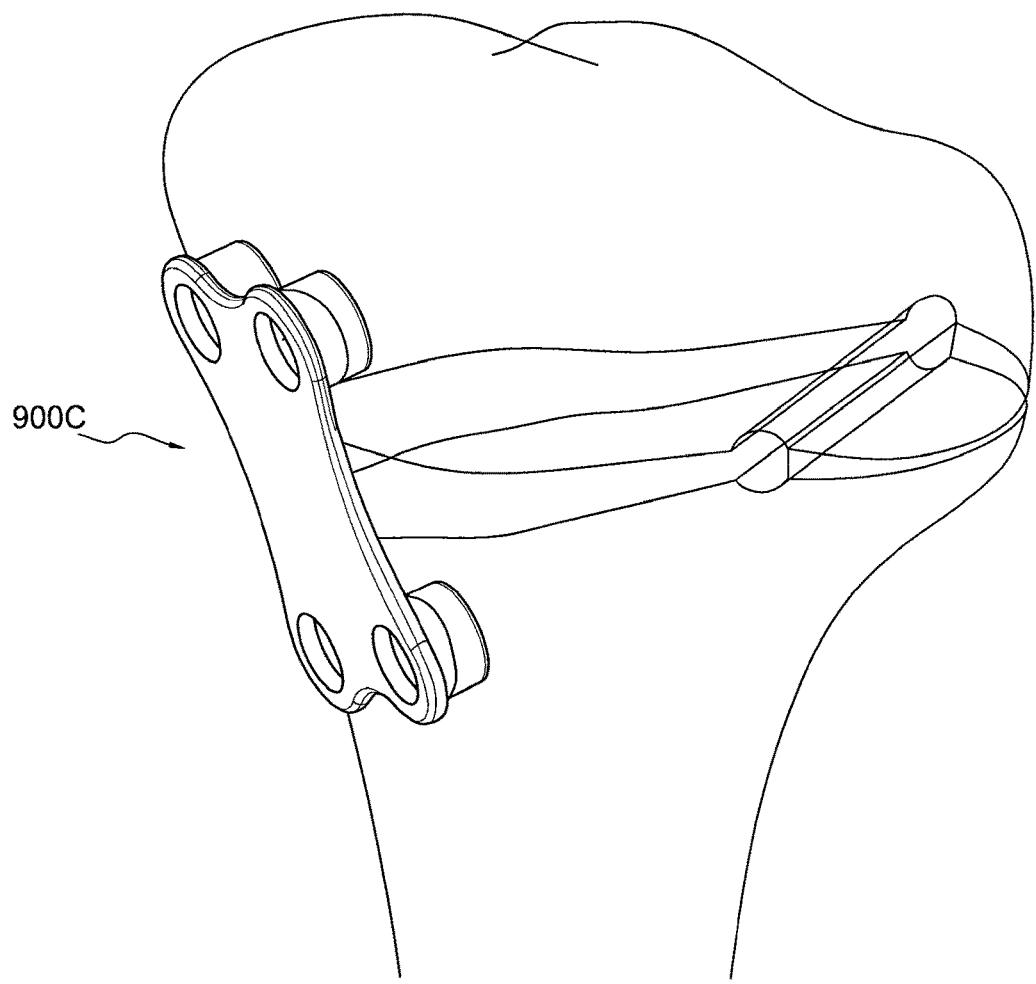

Looking next at FIGS. 62-64, there is shown an osteotomy plate 900C which is also formed in accordance with the present invention. Osteotomy plate 900C is substantially identical to osteotomy plate 900B discussed above, except that it omits the provisions of keys 920B, 925B.

It will be appreciated that the design of osteotomy plate 900C may be advantageous, inasmuch as the omission of the keys simplifies tibial preparation (i.e., formation of the keyholes may be omitted) while still providing substantial lateral and torsional strength due to the provision of bosses 940C.

Anterio-Lateral Osteotomies

In the foregoing description, the present invention is discussed in the context of performing an open wedge osteotomy using an antero-medial approach so as to effect a medial opening wedge osteotomy. Of course, it should be appreciated that the present invention may also be used in antero-lateral approaches so as to effect a lateral opening wedge osteotomy, or in other approaches which will be well known to those skilled in the art.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. An osteotomy plate for maintaining the spacing of a wedge-like opening in bone, the osteotomy plate comprising:
 a body having a front side configured to face away from the wedge-like opening and a back side configured to face toward the wedge-like opening;
 at least two integral key elements extending out of the back side of the body and in a direction substantially perpendicular to the back side of the body for disposition in one or more keyholes formed into the bone within upper and lower wedge side surfaces of the wedge-like opening, wherein the at least two key elements are configured to conform and contact the one or more keyholes, wherein each of the key elements partially surround a window formed within the body of the osteotomy plate; and
 a plurality of mounting holes extending through the body for receiving fasteners therein, the mounting holes extending from the front side to the back side of the body, the mounting holes being formed in the body such that when the key elements are disposed in the one or more keyholes, the mounting holes direct the fasteners into bone on either side of the wedge-like opening,
 wherein the osteotomy plate is configured to extend into the wedge-like opening no further than a depth of the one or more keyholes; and wherein a first key element of the at least two key elements is formed by an upper arc, wherein the upper arc is formed such that an upper convex surface of the upper arc is configured to contact a corresponding keyhole, and a second key element of the at least two key elements is formed by a lower arc, wherein the lower arc is formed such that a lower convex surface of the lower arc is configured to contact a corresponding keyhole, and further wherein the first key element is spaced from the second key element.

2. An osteotomy plate according to claim 1, wherein the body further comprises a plurality of bosses extending out of the back side of the body.

3. An osteotomy plate according to claim 2, wherein each boss is aligned with a mounting hole.

4. An osteotomy plate according to claim 1, wherein the body further comprises an opening to provide access to the interior of the wedge-like opening.

5. An osteotomy plate according to claim 4, wherein the opening is co-axial with at least one of the key elements.

6. An osteotomy plate according to claim 1, wherein the key elements are disposed in an "over-under" configuration.

* * * * *